(12) United States Patent
Bischoff et al.

(10) Patent No.: US 7,074,780 B2
(45) Date of Patent: Jul. 11, 2006

(54) SUBSTITUTED PHENYLCYCLOHEXANECARBOXAMIDES AND THEIR USE

(75) Inventors: Erwin Bischoff, Wuppertal (DE); Thomas Krahn, Hagen (DE); Stephan-Nicholas Müller, Wuppertal (DE); Holger Paulsen, Wuppertal (DE); Joachim Schuhmacher, Wuppertal (DE); Henning Steinhagen, Wuppertal (DE); Wolfgang Thielemann, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 212 days.

(21) Appl. No.: 10/715,283

(22) Filed: Nov. 17, 2003

(65) Prior Publication Data

US 2004/0122004 A1 Jun. 24, 2004

Related U.S. Application Data

(62) Division of application No. 09/943,325, filed on Aug. 30, 2001, now Pat. No. 6,649,616.

(30) Foreign Application Priority Data

Sep. 11, 2000 (DE) ......................... 100 44 792

(51) Int. Cl.
*A61K 31/33* (2006.01)
*A61K 31/38* (2006.01)
*A61K 31/16* (2006.01)
*C07D 331/02* (2006.01)
*C07D 333/02* (2006.01)

(52) U.S. Cl. ..................... 514/183; 514/430; 514/438; 514/613; 514/588; 549/129

(58) Field of Classification Search ............... 514/183, 514/430, 438, 613, 588; 549/1, 29
See application file for complete search history.

(56) References Cited

U.S. PATENT DOCUMENTS 5,607,962 A * 3/1997 Müller-Gliemann et al. ... 514/415

FOREIGN PATENT DOCUMENTS

| EP | 0582164 | | 2/1994 |
|---|---|---|---|
| EP | 0611767 | | 8/1994 |
| EP | 611767 | * | 8/1994 |

OTHER PUBLICATIONS

Becker, L. C., "Conditions for Vasodilator-Induced Coronary Steal in Experimental Myocardial Ischemia", Circulation, 57 (6): 1103–1110 (1978).

DeNinno, M.P., "Annual Reports in Medicinal Chemistry", 33: 111–120 (1998).

Makarewicz, W., "Response of Purine Metabolism to Hypoxia and Ischemia, Purine and Pyrimidine Matabolism in Man", Plenum Press, New York, 11: 351–357 (1998).

Marangos, P.J et al., Potential Therapeutic Roles for Adenosine in Neurologic Disease, Adenosine in the Nervous System, Eds. Stone, T., Academic Press Ltd., p.p. 217–227 (1991).

Murray, T.F.et al., "Manipulation of Endogenous Adenosine Affects Seizure Susceptability", Drug Development Research, 28, 410–415 (1993).

Porkka-Heiskanen, T. et al., "Adenosine: A Mediator of the Sleep-Inducing Effects of Prolonged Wakefulness", Science, 276: 1265–1268 (1997).

Rudolphi, K. A. et al., "Adenosine and Brain Ischema", Cerebrovascular and Brain Metabolism Review, 4: 346–369 (1992).

Strasser, R et al., Zeitschrift fur Kardologle, 85(2): 79–89 (1996).

Sear, J.W. et al., "Issues In the perioperative management of the elderly patient with cardiovascular disease", Pub Med Abstract 12149050; Drugs Aging 19, 429–451 (2002).

Sawynok J. et al., Pharmacological rationale for the clinical use of caffeine, PubMed Abstract 7705215, Drugs, 49, 37–50 (1995).

Jurkowitz, M.S. et al., "Adenosine, inosine, and guanosine protect glial cells during glucose deprivation and mitochondrial inhibition: correlation between Protection and ATP preservation," PubMed Abstract 9681443; J. Neurochem, 71, 535–548 (1998).

* cited by examiner

*Primary Examiner*—Richard L. Raymond
*Assistant Examiner*—Sudhaker B. Patel

(57) ABSTRACT

The present invention relates to substituted phenylcyclohexanecarboxamides of the formula (I)

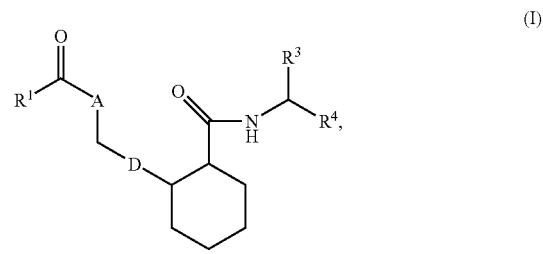

to processes for their preparation and to their use in medicaments, in particular for the prevention and/or treatment of cardiovascular disorders.

16 Claims, No Drawings

SUBSTITUTED PHENYLCYCLOHEXANECARBOXAMIDES AND THEIR USE

This is a divisional of Ser. No. 09/943,325, filed Aug. 30, 2001, now U.S. Pat. No. 6,649,616.

The present invention relates to substituted phenylcyclohexanecarboxamides, to a process for their preparation and to their use in medicaments, in particular for the prevention and/or treatment of cardiovascular disorders, for example for the acute and chronic treatment of ischaemic disorders.

Adenosine is an endogenic effector with cell-protective activity, in particular under cell-damaging conditions with limited oxygen supply, such as, for example, in the case of ischaemia. Adenosine is a highly effective vasodilator. It increases ischaemic "preconditioning" (R. Strasser, A. Vogt, W. Scharper, Z. Kardiologie 85, 1996, 79–89) and can promote the growth of collateral vessels. It is released under hypoxic conditions, for example in the case of cardiac or peripheral occlusive diseases (W. Makarewicz "Purine and Pyrimidine Metabolism in Man", Plenum Press New York, 11, 1998, 351–357). Accordingly, adenosine protects against the effects of disorders caused by ischaemia, for example by increasing the coronary or peripheral circulation by vasodilation, by inhibiting platelet aggregation and by stimulating angiogenesis. Compared to systemically administered adenosine, the adenosine-uptake inhibitors have the advantage of selectivity for ischaemia. Moreover, systemically administered adenosine has a very short half-life. Systemically administered adenosine causes a strong systemic lowering of the blood pressure, which is undesirable, since circulation into the ischaemic regions may be reduced even further ("steal phenomenon", L. C. Becker, Circulation 57, 1978, 1103–1110). The adenosine-uptake inhibitor increases the effect of the adenosine which is formed locally owing to the ischaemia and thus only dilates the vessels in the ischaemic regions. Accordingly, orally or intravenously administered adenosine-uptake inhibitors can be used for preventing and/or treating ischaemic disorders.

Furthermore, there have been various indications of a neuroprotective, anticonvulsive, analgesic and sleep-inducing potential of adenosine-uptake inhibitors, since they increase the intrinsic effects of adenosine by inhibiting its cellulare re-uptake (K. A. Rudolphi et al., Cerebrovascular and Brain Metabolism Reviews 4, 1992, 364–369; T. F. Murray et al., Drug Dev. Res. 28, 1993, 410–415; T. Porkka-Heiskanen et al., Science 276, 1997, 1265–1268; 'Adenosine in the Nervous System', Ed.: Trevor Stone, Academic Press Ltd. 1991, 217–227; M. P. DeNinno, Annual Reports in Medicinal Chemistry 33, 1998, 111–120).

It is an object of the present invention to provide novel substances for preventing and/or treating cardiovascular disorders, the substances having improved administration properties.

The present invention relates to compounds of the formula

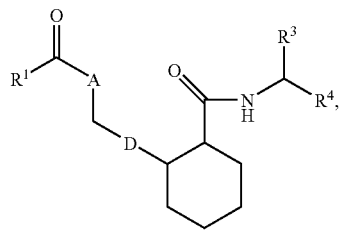

(I)

in which

D represents a radical

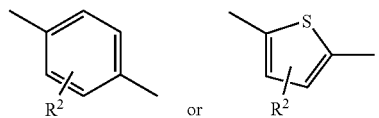

in which

R² represents hydrogen, halogen, hydroxyl, carboxyl, cyano, nitro, trifluoromethyl, trifluoromethoxy, ($C_1$–$C_6$)-alkyl, ($C_1$–$C_6$)-alkoxy or ($C_1$–$C_6$)-alkoxycarbonyl, A represents an oxygen atom or a group of the formula N—R⁵ or CH—R⁶, in which R⁵ represents hydrogen, ($C_1$–$C_6$)-alkyl, ($C_3$–$C_7$)-cycloalkyl, where alkyl and cycloalkyl for their part may be substituted up to three times independently of one another by hydroxyl or mono- or di-($C_1$–$C_6$)-alkylamino, represents ($C_6$–$C_{10}$)-aryl, 5- to 10-membered heteroaryl having up to three heteroatoms from the group consisting of N, O and S or 5- or 6-membered heterocyclyl having up to three heteroatoms from the group consisting of N, O and S, where aryl, heteroaryl and heterocyclyl for their part may be substituted up to three times independently of one another by halogen, hydroxyl, cyano, nitro, trifluoromethyl, trifluoromethoxy, ($C_1$–$C_6$)-alkyl, ($C_1$–$C_6$)-alkoxy, ($C_1$–$C_6$)-alkoxycarbonyl or mono- or di-($C_1$–$C_6$)-alkylamino, R⁶ represents hydrogen, ($C_1$–$C_6$)-alkoxycarbonyl or carboxyl, R¹ represents hydrogen, ($C_1$–$C_6$)-alkyl, which for its part may be substituted by hydroxyl or ($C_1$–$C_4$)-alkoxy, represents ($C_3$–$C_7$)-cycloalkyl, ($C_6$–$C_{10}$)-aryl, 5- to 10-membered heteroaryl having up to two heteroatoms from the group consisting of N, O and S, where aryl and heteroaryl for their part may be substituted independently of one another by halogen, or represents a radical of the formula —NR⁷R⁸ or —OR⁹, in which R⁷ and R⁸ independently of one another represent hydrogen, ($C_6$–$C_{10}$)-aryl, adamantyl, ($C_1$–$C_8$)-alkyl, whose chain may be interrupted by one or two oxygen atoms and which may be substituted up to three times independently of one another by hydroxyl, phenyl, trifluoromethyl, ($C_3$–$C_8$)-cycloalkyl, ($C_1$–$C_6$)-alkoxy, mono- or di-($C_1$–$C_6$)-alkylamino, 5- or 6-membered heterocyclyl having up to three heteroatoms from the group consisting of N, O and S or by 5- to 10-membered heteroaryl having up to three heteroatoms from the group consisting of N, O and S, represent ($C_3$–$C_8$)-cycloalkyl, which may be substituted up to three times independently of one another by ($C_1$–$C_4$)-alkyl, hydroxyl or oxo, or represent 5- or 6-membered heterocyclyl having up to two heteroatoms from the group consisting of N, O and S, where N is substituted by hydrogen or ($C_1$–$C_4$)-alkyl, or R⁷ and R⁸ together with the nitrogen atom to which they are attached form a 4- to 7-membered saturated heterocycle which may contain up to two further heteroatoms from the group consisting of N, O and S and which is optionally substituted by hydroxyl, oxo or ($C_1$–$C_6$)-alkyl, which for its part may be substituted by hydroxyl, and
- $R^9$ represents $(C_6–C_{10})$-aryl, adamantyl, $(C_1–C_8)$-alkyl, whose chain may be interrupted by one or two oxygen atoms and which may be substituted up to three times independently of one another by hydroxyl, phenyl, trifluoromethyl, $(C_3–C_8)$-cycloalkyl, $(C_1–C_6)$-alkoxy, mono- or di-$(C_1–C_6)$-alkylamino, 5- or 6-membered heterocyclyl having up to three heteroatoms from the group consisting of N, O and S or by 5- to 10-membered heteroaryl having up to three heteroatoms from the group consisting of N, O and S, represents $(C_3–C_8)$-cycloalkyl, which may be substituted up to three times independently of one another by $(C_1–C_4)$-alkyl, hydroxyl or oxo, or represents 5- or 6-membered heterocyclyl having up to two heteroatoms from the group consisting of N, O and S, where N is substituted by hydrogen or $(C_1–C_4)$-alkyl,
- $R^3$ represents $(C_1–C_8)$-alkyl, whose chain may be interrupted by a sulphur or oxygen atom or an S(O) or $SO_2$ group, represents phenyl, benzyl or 5- or 6-membered heteroaryl having up to two heteroatoms from the group consisting of N, O and S, where phenyl, benzyl and heteroaryl may be substituted up to three times independently of one another by halogen, trifluoromethyl, cyano, nitro, hydroxyl, $(C_1–C_6)$-alkyl or $(C_1–C_6)$-alkoxy, and
- $R^4$ represents a radical of the formula —C(O)—$NR^{10}R^{11}$, in which
   $R^{10}$ and $R^{11}$ independently of one another represent hydrogen or $(C_1–C_6)$-alkyl, and their salts, hydrates, hydrates of the salts and solvates.

Salts of the compounds according to the invention are physiologically acceptable salts of the substances according to the invention with mineral acids, carboxylic acids or sulphonic acids. Particular preference is given, for example, to salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acids, acetic acid, propionic acid, lactic acid, tartaric acid, citric acid, fumaric acid, maleic acid or benzoic acid.

Salts can also be physiologically acceptable metal or ammonium salts of the compounds according to the invention. Particularly preferred are alkali metal salts (for example sodium salts or potassium salts), alkaline earth metal salts (for example magnesium salts or calcium salts), and also ammonium salts, which are derived from ammoia or organic amines, such as, for example, ethylamine, di- or triethylamine, di- or triethanolamine, dicyclohexylamine, dimethylaminoethanol, arginine, lysine, ethylenediamine or 2-phenylethylamine.

Depending on the substitution pattern, the compounds according to the invention can exist in stereoisomeric forms which are either like image and mirror image (enantiomers) or which are not like image and mirror image (diastereomers). The invention relates both to the enantiomers or diastereomers and to their respective mixtures. The racemic forms, like the diastereomers, can be separated in a known manner into the stereoisomerically uniform components.

Moreover, the invention also includes prodrugs of the compounds according to the invention. According to the invention, prodrugs are those forms of the compounds of the above formula (I) which for their part may be biologically active or inactive, but which are converted under physiological conditions (for example metabolically or solvolytically) into the corresponding biologically active form.

According to the invention, "hydrates" or "solvates" are those forms of the compounds of the above formula (I) which, in solid or liquid state, form a molecular compound or a complex by hydration with water or coordination with solvent molecules. Examples of hydrates are sesquihydrates, monohydrates, dihydrates and trihydrates. Equally suitable are the hydrates or solvates of salts of the compounds according to the invention.

Halogen represents fluorine, chlorine, bromine and iodine. Preference is given to chlorine or fluorine.

$(C_1–C_8)$-alkyl represents a straight-chain or branched alkyl radical having 1 to 8 carbon atoms. Examples which may be mentioned are: methyl, ethyl, n-propyl, isopropyl, n-butyl, isobutyl, tert-butyl, n-pentyl, n-hexyl and n-octyl. The corresponding alkyl groups having fewer carbon atoms, such as, for example $(C_1–C_6)$-alkyl, $(C_1–C_4)$-alkyl and $(C_1–C_3)$-alkyl, are derived analogously from this definition. In general, $(C_1–C_3)$-alkyl is preferred.

The meaning of the corresponding component of other, more complex substituents, such as, for example, di-alkylamino, mono- or di-alkylamino is also derived from this definition.

Mono- or di-$(C_1–C_4)$-alkylamino represents an amino group having one or two identical or different straight-chain or branched alkyl substituents of in each case 1 to 4 carbon atoms. Examples which may be mentioned are: methylamino, ethylamino, n-propylamino, isopropyl amino, tert-butyl amino, N,N-dimethylamino, N,N-diethylamino, N-ethyl-N-methylamino, N-methyl-N-n-propylamino, N-isopropyl-N-n-propyl amino and N-t-butyl-N-methylamino.

$C_3–C_8$)-Cycloalkyl represents a cyclic alkyl radical having 3 to 8 carbon atoms. Examples which may be mentioned are: cyclopropyl, cyclobutyl, cyclopentyl, cyclohexyl, cycloheptyl and cyclooctyl. The corresponding cycloalkyl groups having fewer carbon atoms, such as, for example, $(C_3–C_7)$-cycloalkyl or $(C_3–C_6)$-cycloalky, are derived analogously from this definition. Preference is given to cyclopropyl, cyclopentyl and cyclohexyl.

$(C_1–C_6)$-Alkoxy represents a straight-chain or branched alkoxy radical having 1 to 6 carbon atoms. Examples which may be mentioned: methoxy, ethoxy, n-propoxy, isopropoxy, n-butoxy, isobutoxy, tert-butoxy, n-pentoxy and n-hexoxy. The corresponding alkoxy groups having fewer carbon atoms, such as, for example, $(C_1–C_4)$-alkoxy or $(C_1–C_3)$-alkoxy, are derived analogously from this definition. In general, $(C_1–C_3)$-alkoxy is preferred.

The meaning of the corresponding component of other, more complex substituents, such as, for example, alkoxycarbonyl, which represents an alkoxy radical which is attached via a carbonyl group, is also derived from this definition.

$(C_6–C_{10})$-Aryl represents an aromatic radical having 6 to 10 carbon atoms. Examples which may be mentioned are: phenyl and naphthyl.

5- to 10-membered heteroaryl having up to 3 heteroatoms from the group consisting of N, O and S represents a mono- or bicyclic heteroaromatic which is attached via a ring carbon atom of the heteroaromatic, if appropriate also via a ring nitrogen atom of the heteroaromatic. Examples which may be mentioned are: pyridyl, pyrimidyl, pyridazinyl, pyrazinyl, thienyl, furyl, pyrrolyl, pyrazolyl, imidazolyl, triazolyl, thiazolyl, oxazolyl, oxdiazolyl, isoxazolyl, benzofuranyl, benzothienyl or benzimidazolyl. The corresponding heterocycles having fewer heteroatoms, such as, for example, those having up to 2 heteroatoms from the group consisting of N, O and S are derived analogously from this definition. In general, preference is given to 5- or 6-membered aromatic heterocycles having up to 2 heteroatoms from the group consisting of N, O and S, such as, for example, pyridyl, pyrimidyl, pyridazinyl, furyl, imidazolyl and thienyl.

5- or 6-membered heterocyclyl having up to 3 heteroatoms from the group consisting of N, O and S represents a saturated or partially unsaturated heterocycle which is attached via a ring carbon atom or a ring nitrogen atom. Examples which may be mentioned are: tetrahydrofuryl, pyrrolidinyl, pyrrolinyl, dihydropyridinyl, piperidinyl, piperazinyl, morpholinyl, thiomorpholinyl. Preference is given to saturated heterocycles, in particular to piperidinyl, piperazinyl, morpholinyl and pyrrolidinyl.

The compounds of the formula (I) according to the invention can be present in at least eight different configurations, the four different configurations (Ia) to (Id) below being preferred:

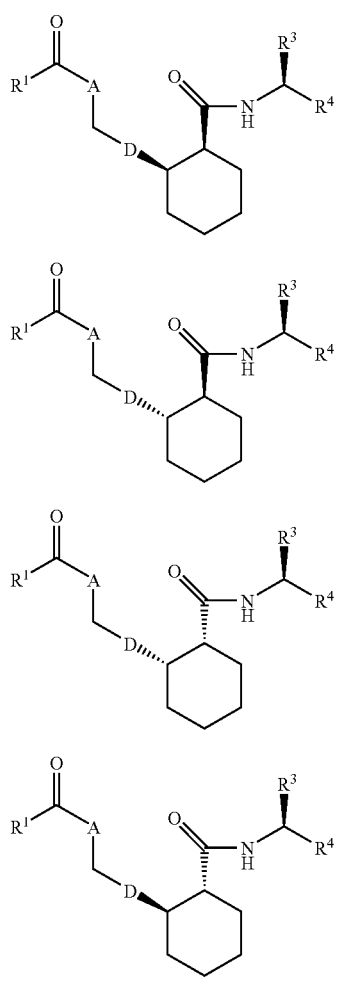

Particular preference is given to the configuration (Id).

Preference is furthermore given to compounds of the formula (I) according to the invention in which D represents a radical

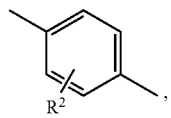

in which $R^2$ represents hydrogen, halogen, hydroxyl, carboxyl, cyano, nitro, trifluoromethyl, trifluoromethoxy, $(C_1-C_6)$-alkyl, $(C_1-C_6)$-alkoxy or $(C_1-C_6)$-alkoxycarbonyl, A represents an oxygen atom or a group of the formula N—$R^5$ or CH—$R^6$, in which $R^5$ represents hydrogen, $(C_1-C_6)$-alkyl, $(C_3-C_7)$-cycloalkyl, where alkyl and cycloalkyl for their part may be substituted up to three times independently of one another by hydroxyl or mono- or di-$(C_1-C_6)$-alkylamino, represents $(C_6-C_{10})$-aryl, 5- to 10-membered heteroaryl having up to three heteroatoms from the group consisting of N, O and S or 5- or 6-membered heterocyclyl having up to three heteroatoms from the group consisting of N, O and S, where aryl, heteroaryl and heterocyclyl for their part may be substituted up to three times independently of one another by halogen, hydroxyl, cyano, nitro, trifluoromethyl, trifluoromethoxy, $(C_1-C_6)$-alkyl, $(C_1-C_6)$-alkoxy, $(C_1-C_6)$-alkoxycarbonyl or mono- or di-$(C_1-C_6)$-alkylamino, $R^6$ represents hydrogen, $(C_1-C_6)$-alkoxycarbonyl or carboxyl, $R^1$ represents hydrogen, $(C_1-C_6)$-alkyl, which for its part may be substituted by hydroxyl or $(C_1-C_4)$-alkoxy, represents $(C_3-C_7)$-cycloalkyl, $(C_6-C_{10})$-aryl, 5- to 10-membered heteroaryl having up to two heteroatoms from the group consisting of N, O and S, where aryl and heteroaryl for their part may be substituted independently of one another by halogen, or represents a radical of the formula —$NR^7R^8$ or —$OR^9$, in which $R^7$ and $R^8$ independently of one another represent hydrogen, $(C_6-C_{10})$-aryl, adamantyl, $(C_1-C_8)$-alkyl, whose chain may be interrupted by one or two oxygen atoms and which may be substituted up to three times independently of one another by hydroxyl, phenyl, trifluoromethyl, $(C_3-C_8)$-cycloalkyl, $(C_1-C_6)$-alkoxy, mono- or di-$(C_1-C_6)$-alkylamino, 5- or 6-membered heterocyclyl having up to three heteroatoms from the group consisting of N, O and S or by 5- to 10-membered heteroaryl having up to three heteroatoms from the group consisting of N, O and S, represent $(C_3-C_8)$-cycloalkyl, which may be substituted up to three times independently of one another by $(C_1-C_4)$-alkyl, hydroxyl or oxo, or represent 5- or 6-membered heterocyclyl having up to two heteroatoms from the group consisting of N, O and S, where N is substituted by hydrogen or $(C_1-C_4)$-alkyl, or $R^7$ and $R^8$ together with the nitrogen atom to which they are attached form a 4- to 7-membered saturated heterocycle which may contain up to two further heteroatoms from the group consisting of N, O and S and which is optionally substituted by hydroxyl, oxo or $(C_1-C_6)$-alkyl, which for its part may be substituted by hydroxyl, and R⁹ represents $(C_6–C_{10})$-aryl, adamantyl, $(C_1–C_8)$-alkyl, whose chain may be interrupted by one or two oxygen atoms and which may be substituted up to three times independently of one another by hydroxyl, phenyl, trifluoromethyl, $(C_3–C_8)$-cycloalkyl, $(C_1–C_6)$-alkoxy, mono- or di-$(C_1–C_6)$-alkylamino, 5- or 6-membered heterocyclyl having up to three heteroatoms from the group consisting of N, O and S or by 5- to 10-membered heteroaryl having up to three heteroatoms from the group consisting of N, O and S, represents $(C_3–C_8)$-cycloalkyl, which may be substituted up to three times independently of one another by $(C_1–C_4)$-alkyl, hydroxyl or oxo, or represents 5- or 6-membered heterocyclyl having up to two heteroatoms from the group consisting of N, O and S, where N is substituted by hydrogen or $(C_1–C_4)$-alkyl, R³ represents $(C_1–C_8)$-alkyl, whose chain may be interrupted by a sulphur atom or an S(O) or SO₂ group, represents phenyl, benzyl or 5- or 6-membered heteroaryl having up to two heteroatoms from the group consisting of N, O and S, where phenyl, benzyl and heteroaryl may be substituted up to three times independently of one another by halogen, trifluoromethyl, cyano, nitro, hydroxyl, $(C_1–C_6)$-alkyl or $(C_1–C_6)$-alkoxy, and R⁴ represents a radical of the formula —C(O)—NR¹⁰R¹¹, in which R¹⁰ and R¹¹ independently of one another represent hydrogen or $(C_1–C_6)$-alkyl, and their salts, hydrates, hydrates of the salts and solvates.

Particular preference is given to compounds of the formula (I) according to the invention, in which D represents a radical

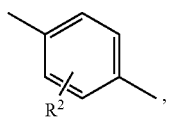

in which

R² represents hydrogen, chlorine or fluorine,

A represents an oxygen atom or a group of the formula N—R⁵, in which

R⁵ represents hydrogen, $(C_1–C_6)$-alkyl, which for its part may be substituted up to two times by hydroxyl, represents $(C_3–C_7)$-cycloalkyl, phenyl or 5- or 6-membered heteroaryl having up to three heteroatoms from the group consisting of N, O and S, where phenyl and heteroaryl for their part may be substituted up to two times independently of one another by halogen, cyano, trifluoromethyl, trifluoromethoxy, $(C_1–C_4)$-alkyl, $(C_1–C_4)$-alkoxy or di-$(C_1–C_4)$-alkylamino, R¹ represents hydrogen, $(C_1–C_6)$-alkyl, which for its part may be substituted by hydroxyl or $(C_1–C_4)$-alkoxy, represents $(C_3–C_7)$-cycloalkyl, phenyl, 5- or 6-membered heteroaryl having up to two heteroatoms from the group consisting of N, O and S, where phenyl and heteroaryl for their part independently of one another may be substituted by halogen, or represents a radical of the formula —NR⁷R⁸ or —OR⁹, in which R⁷ and R⁸ independently of one another represent hydrogen, phenyl, adamantyl, $(C_1–C_6)$-alkyl, whose chain may be interrupted by one or two oxygen atoms and which may be substituted up to two times independently of one another by hydroxyl, phenyl, trifluoromethyl, $(C_3–C_6)$-cycloalkyl, $(C_1–C_4)$-alkoxy, mono- or di-$(C_1–C_4)$-alkylamino, 5- or 6-membered heterocyclyl having up to two heteroatoms from the group consisting of N and O or by 5- or 6-membered heteroaryl having up to three heteroatoms from the group consisting of N, O and S, represents $(C_3–C_8)$-cycloalkyl, which may be substituted up to two times by hydroxyl, or represent 5- or 6-membered heterocyclyl having up to two heteroatoms from the group consisting of N, O and S, where N is substituted by hydrogen or $(C_1–C_4)$-alkyl, or R⁷ and R⁸ together with the nitrogen atom to which they are attached form a 4- to 7-membered saturated heterocycle which may contain up to two further heteroatoms from the group consisting of N, O and S and which is optionally substituted by hydroxyl, oxo or $(C_1–C_6)$-alkyl, which for its part may be substituted by hydroxyl, and R⁹ represents phenyl, adamantyl, $(C_1–C_6)$-alkyl, whose chain may be interrupted by one or two oxygen atoms and which may be substituted up to two times independently of one another by hydroxyl, phenyl, trifluoromethyl, $(C_3–C_6)$-cycloalkyl, $(C_1–C_3)$-alkoxy, mono- or di-$(C_1–C_4)$-alkylamino, 5- or 6-membered heterocyclyl having up to two heteroatoms from the group consisting of N and O or by 5- or 6-membered heteroaryl having up to three heteroatoms from the group consisting of N, O and S, represents $(C_3–C_8)$-cycloalkyl, which may be substituted up to two times by hydroxyl, or represents 5- or 6-membered heterocyclyl having up to two heteroatoms from the group consisting of N, O and S, where N is substituted by hydrogen or $(C_1–C_4)$-alkyl, R³ represents $(C_1–C_8)$-alkyl, whose chain may be interrupted by a sulphur atom or an S(O) or SO₂ group, represents phenyl, benzyl or 5- or 6-membered heteroaryl having up to two heteroatoms from the group consisting of N, O and S, where phenyl, benzyl and heteroaryl may be substituted up to two times independently of one another by halogen, trifluoromethyl, cyano, $(C_1–C_3)$-alkyl, $(C_1–C_3)$-alkoxy or hydroxyl, and R⁴ represents a radical of the formula —C(O)—NR¹⁰R¹¹, in which R¹⁰ and R¹¹ independently of one another represent hydrogen or $(C_1–C_6)$-alkyl, and their salts, hydrates, hydrates of the salts and solvates.

Very particular preference is given to compounds of the formula (I) according to the invention in which D represents a radical

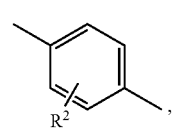

in which

R² represents hydrogen,

A represents an oxygen atom or a group of the formula N—R⁵, in which
R$^5$ represents hydrogen, (C$_1$–C$_6$)-alkyl, which for its part may be substituted up to two times by hydroxyl, represents (C$_3$–C$_7$)-cycloalkyl, phenyl or 5- or 6-membered heteroaryl having up to three heteroatoms from the group consisting of N, O and S, where phenyl and heteroaryl for their part may be substituted up to two times independently of one another by fluorine, chlorine, cyano, trifluoromethyl, trifluoromethoxy, (C$_1$–C$_3$)-alkyl, (C$_1$–C$_3$)-alkoxy or di-(C$_1$–C$_3$)-alkylamino, R$^1$ represents (C$_1$–C$_4$)-alkyl or a radical of the formula —NR$^7$R$^8$, in which
R$^7$ and R$^8$ independently of one another represent hydrogen, phenyl, adamantyl, (C$_1$–C$_4$)-alkyl, whose chain may be interrupted by one or two oxygen atoms and which may be substituted up to two times independently of one another by hydroxyl, phenyl, trifluoromethyl, (C$_3$–C$_6$)-cycloalkyl, (C$_1$–C$_3$)-alkoxy, mono- or di-(C$_1$–C$_3$)-alkylamino, 5- or 6-membered heterocyclyl having up to two heteroatoms from the group consisting of N and O or by 5- or 6-membered heteroaryl having up to three heteroatoms from the group consisting of N, O and S, represent (C$_3$–C$_8$)-cycloalkyl, which may be substituted up to two times by hydroxyl, or represents 5- or 6-membered heterocyclyl having up to two heteroatoms from the group consisting of N, O and S, where N is substituted by hydrogen or (C$_1$–C$_4$)-alkyl, or
R$^7$ and R$^8$ together with the nitrogen atom to which they are attached form a 4- to 7-membered saturated heterocycle which may contain up to two further heteroatoms from the group consisting of N, O and S and which is optionally substituted by by hydroxyl, oxo or (C$_1$–C$_6$)-alkyl, which for its part may be substituted by hydroxyl, R$^3$ represents (C$_1$–C$_8$)-alkyl, whose chain may be interrupted by a sulphur atom or an S(O) or SO$_2$ group, represents phenyl, benzyl or 5- or 6-membered heteroaryl having up to two heteroatoms from the group consisting of N, O and S, where phenyl, benzyl and heteroaryl may be substituted up to two times independently of one another by halogen, trifluoromethyl, cyano, (C$_1$–C$_3$)-alkyl, (C$_1$–C$_3$)-alkoxy or hydroxyl, and
R$^4$ represents a radical of the formula —C(O)—NR$^{10}$R$^{11}$,
in which
R$^{10}$ and R$^{11}$ independently of one another represent hydrogen, methyl or ethyl, and their salts, hydrates, hydrates of the salts and solvates.

Most particular preference is given to compounds of the formula (I),
in which
D is a radical

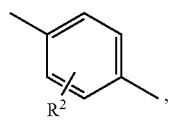, in which
R$^2$ represents hydrogen,
A represents an oxygen atom or a group of the formula N—R$^5$, in which
R$^5$ represents (C$_3$–C$_7$)-cycloalkyl, phenyl, which for its part may be substituted by fluorine, or represents pyridyl, R$^1$ represents methyl or a radical of the formula —NR$^7$R$^8$,
in which
R$^7$ and R$^8$ independently of one another represent (C$_1$–C$_4$)-alkyl, which may be mono- or disubstituted by hydroxyl, or
R$^7$ and R$^8$ together with the nitrogen atom to which they are attached form a 5- or 6-membered saturated heterocycle which may contain a further heteroatom O or N, where N is substituted by hydrogen or (C$_1$–C$_3$)-alkyl, which for its part may be substituted by hydroxyl, R$^3$ represents phenyl, which is optionally substituted in the para-position by fluorine, or represents pyridyl,
and
R$^4$ represents a radical of the formula —C(O)—NR$^{10}$R$^{11}$,
in which
R$^{10}$ and R$^{11}$ represent hydrogen, and their salts, hydrates, hydrates of the salts and solvates.

Most particular preference is also given to:

(1R,2R)-N-[(1S)-2-amino-1-(4-fluorophenyl)-2-oxoethyl]-2-(4-{[{[ethyl(2-hydroxyethyl)amino]carbonyl}(4-fluorophenyl)amino]methyl}phenyl)cyclohexanecarboxamide

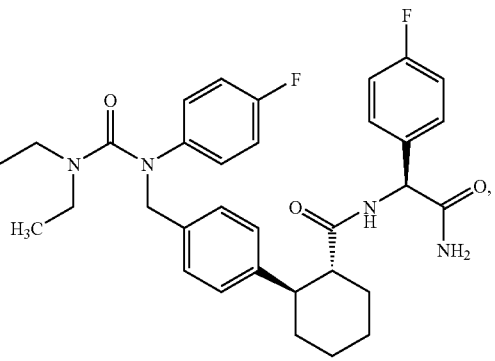

(1R,2R)-N-[(1S)-2-amino-2-oxo-1-phenylethyl]-2-(4-{[[(dimethylamino)carbonyl](phenyl)amino]methyl}phenyl)cyclohexanecarboxamide

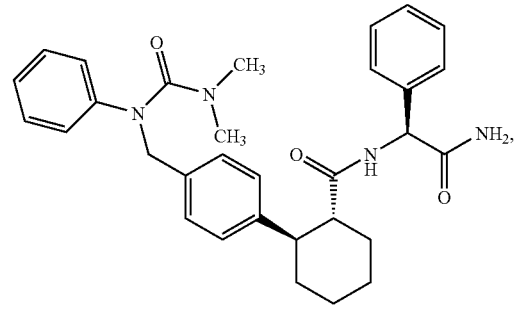

11

(1R,2R)-N-[(1S)-2-amino-2-oxo-1-phenylethyl]-2-[4-({cyclopropyl[(dimethylamino)carbonyl]amino}methyl)phenyl]cyclohexanecarboxamide

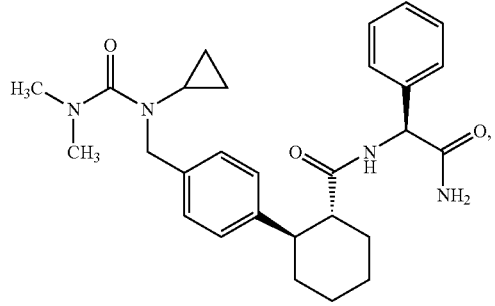

(1R,2R)-N-[(1S)-2-amino-2-oxo-1-phenylethyl]-2-(4-{[[(diethylamino)carbonyl](2-pyridinyl)amino]methyl}phenyl)cyclohexanecarboxamide

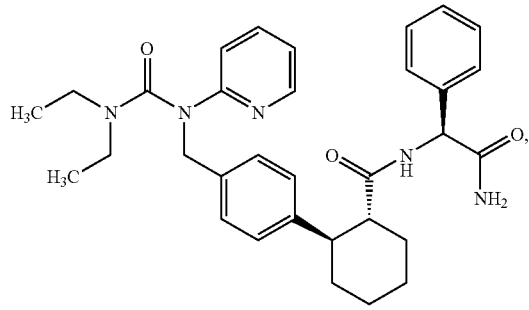

N-{4-[(1R,2R)-2-({[(1S)-2-amino-2-oxo-1-phenylethyl]amino}carbonyl)cyclohexyl]benzyl}-N-phenyl-4-morpholinecarboxamide

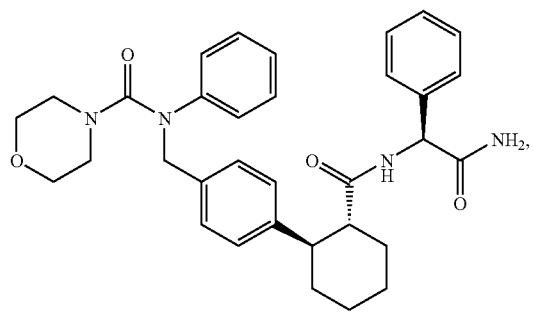

12

(S)-N-{{(1R,2R)-2-(4-{[{[2-hydroxyethylamino]carbonyl}(phenyl)amino]methyl}phenyl)cyclohex-1-yl}carbonyl}-phenylglycinamide

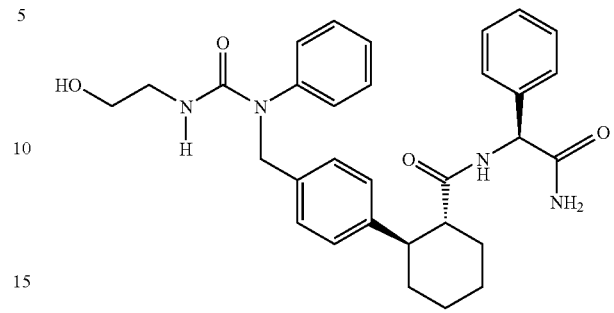

(1R,2R)-2-(4-{[acetyl(2-pyridinyl)amino]methyl}phenyl)-N-[(1S)-2-amino-2-oxo-1-phenylethyl]cyclohexancarboxamide

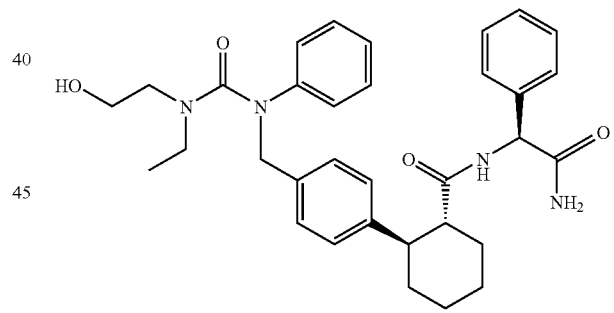

(1R,2R)-N-[(1S)-2-amino-1-phenyl-2-oxoethyl]-2-(4-{[{[ethyl(2-hydroxyethyl)amino]carbonyl}(phenyl)amino]methyl}phenyl)cyclohexanecarboxamide 4-[(1R,2R)-2-({[(1S)-2-amino-1-(4-fluorophenyl)-2-oxoethyl]amino}carbonyl)cyclohexyl]benzyl 4-(2-hydroxyethyl)-1-piperazinecarbamate

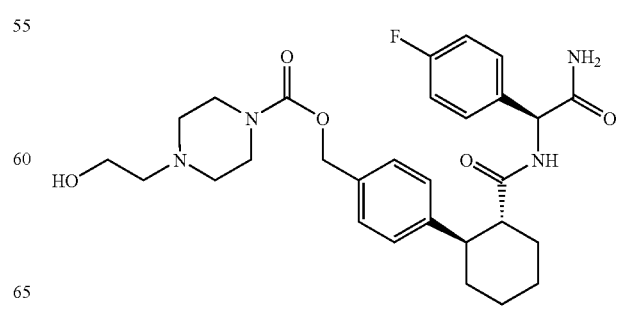

4-[(1R,2R)-2-({[(1S)-2-amino-1-phenyl-2-oxoethyl]amino}carbonyl)cyclohexyl]benzyl-4-(2-hydroxyethyl)-1-piperazinecarbamate

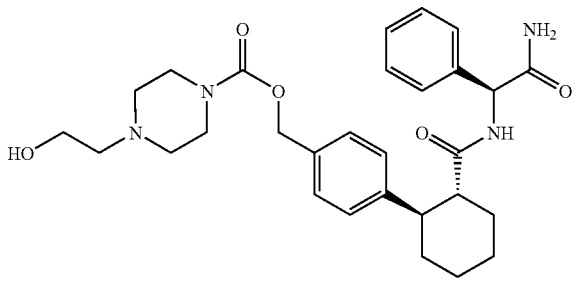

and their salts, hydrates, hydrates of the salts and solvates.

Moreover, we have found a process for preparing the compounds of the formula (I) according to the invention where

[A] compounds of the formula (II)

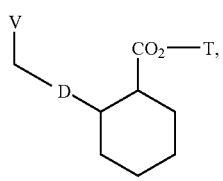

(II)

in which
D is as defined above,
T represents $(C_1–C_4)$-alkyl, preferably methyl or tert-butyl, and
V represents a suitable leaving group, such as, for example, halogen, mesylate or tosylate, preferably bromine,
are initially converted by reaction with compounds of the formula (III)

B—H (III), in which
B represents

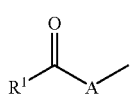

or
optionally, if $R^1$ reprsents $OR^9$,
represents

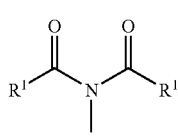

and
$R^1$ and A are each as defined above, where any amino and hydroxyl functions which may be present are optionally blocked by customary amino or hydroxyl protective groups, and to the compounds of the formula (IV)

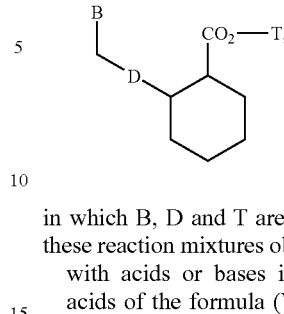

(IV)

in which B, D and T are each as defined above,
these reaction mixtures obtained are in a next step converted with acids or bases into the corresponding carboxylic acids of the formula (V)

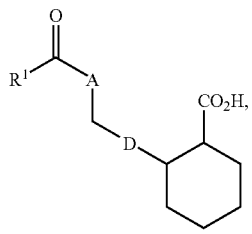

(V)

in which
$R^1$, A and D are as defined above,
which are, if appropriate, activated, in particular by conversion into a corresponding carboxylic acid derivative, such as a carbonyl halide, a carboxylic anhydride or a carboxylic acid,
and these compounds are finally reacted in inert solvents according to known methods with compounds of the formula (VI) or salts thereof

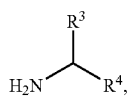

(VI)

in which
$R^3$ and $R^4$ are as defined above,
or
[B] if A represents an oxygen atom or $NR^5$,
compounds of the formula (VII)

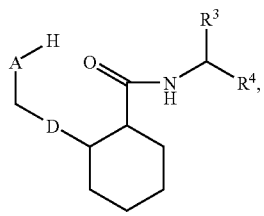

(VII)

in which
D, $R^3$ and $R^4$ are as defined above
and
A represents an oxygen atom or a group of the formula $N—R^5$,
where $R^5$ is as defined above,
if appropriate in the presence of a base, are reacted either with compounds of the formula (VIII)

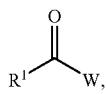
(VIII)

in which
R¹ is as defined above and W represents a suitable leaving group, such as, for example, the corresponding symmetric anhydride or a halogen, preferably chlorine,
or
with a phosgene equivalent, such as, for example, disuccinimidyl carbonate, and then with compounds of the formula (IX)

(IX), in which
R⁷ and R⁸ are as defined above,
or
with an isocyanate of the formula (X)

R⁷NCO  (X), in which
R⁷ is as defined above.

The compounds of the formula (I) obtained according to process variant [A] or [B] can, if appropriate, subsequently be converted into the corresponding salts, for example by reaction with an acid.

The compounds of the corresponding diastereomeric and enantiomeric forms are prepared correspondingly, either using enantiomerically or diastereomerically pure starting materials or by subsequent separation of the racemates formed by customary methods (for example racemate resolution, chromatography on chiral columns, etc.).

The process according to the invention is illustrated in an exemplary manner by the equation below:

[A]

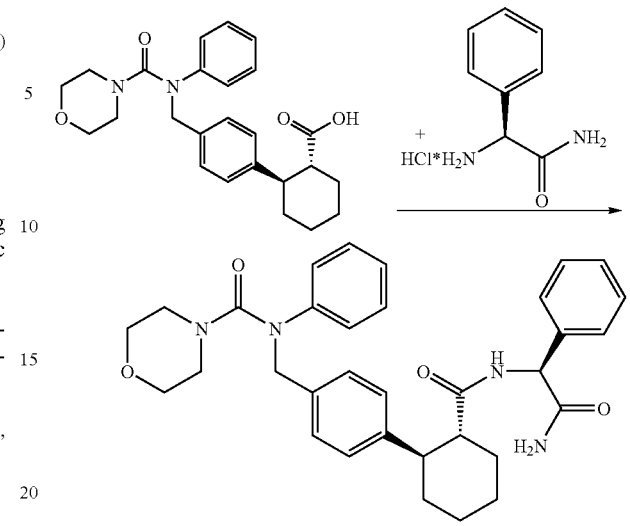

If R¹ represents OR⁹, the following synthesis sequence is likewise possible:

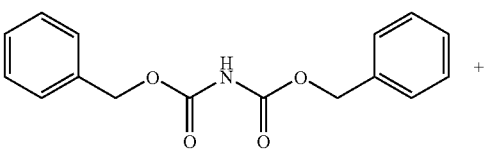

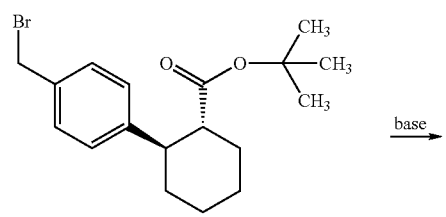

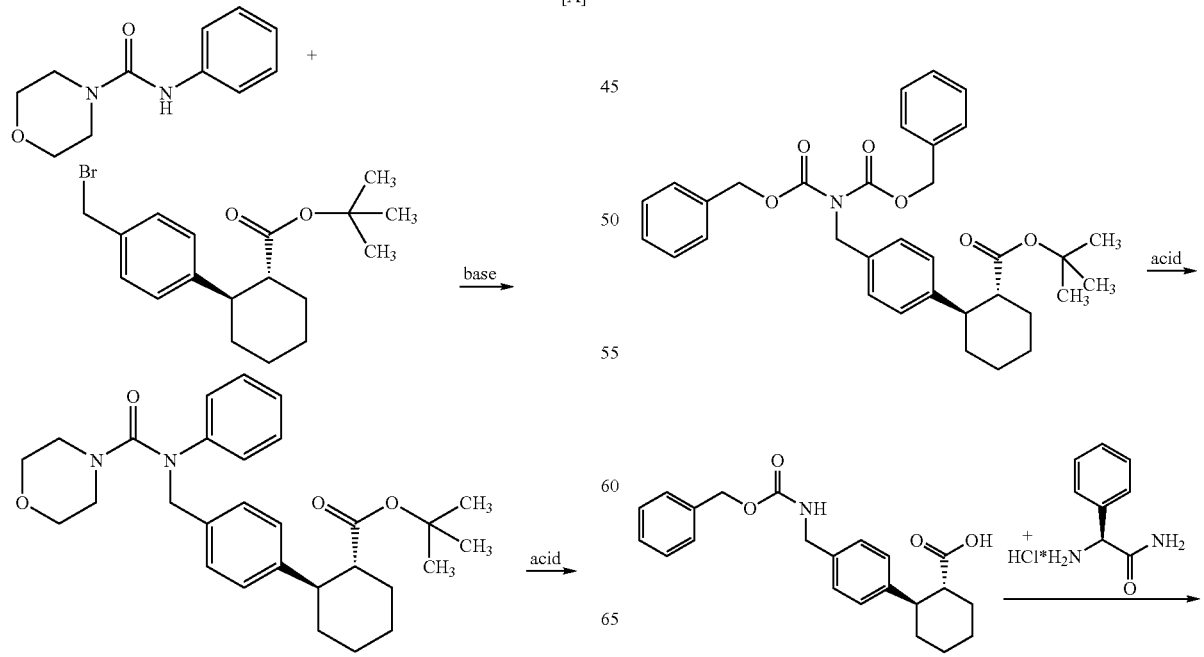

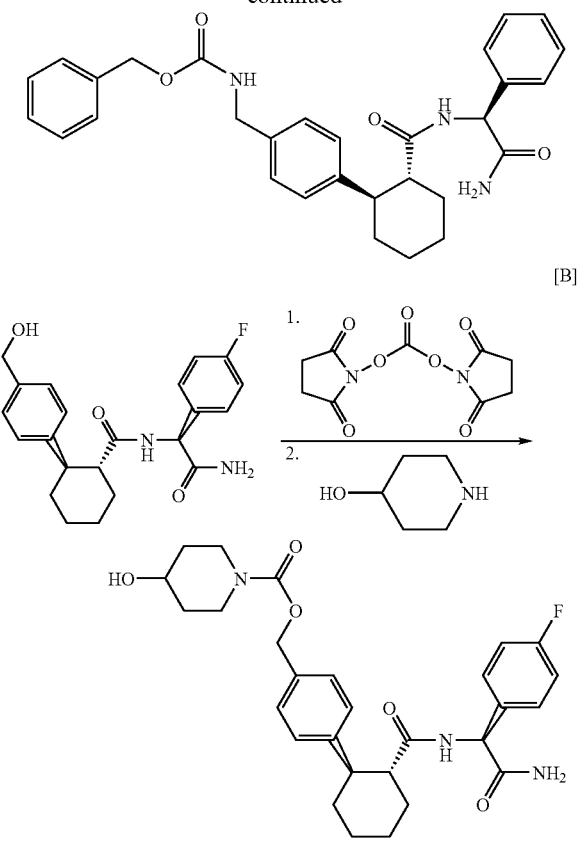

[B]

The process according to the invention is generally carried out under atmospheric pressure. However, it is also possible to carry out the process under elevated pressure or under reduced pressure (for example in a range from 0.5 to 5 bar).

In the context of the invention, customary amino protective groups are the amino protective groups used in peptide chemistry.

These preferably include: benzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 4-nitrobenzyloxycarbonyl, 2-nitro-4,5-dimethoxybenzyloxycarbonyl, methoxycarbonyl, ethoxycarbonyl, propoxycarbonyl, isopropoxycarbonyl, butoxycarbonyl, isobutoxycarbonyl, tert-butoxycarbonyl, allyloxycarbonyl, vinyloxycarbonyl, 2-nitrobenzyloxycarbonyl, 3,4,5-trimethoxybenzyloxycarbonyl, cyclohexoxycarbonyl, 1,1-dimethylethoxycarbonyl, adamantylcarbonyl, phthaloyl, 2,2,2-trichlorethoxycarbonyl, 2,2,2-trichloro-tert-butoxycarbonyl, Menthyloxycarbonyl, phenoxycarbonyl, 4-nitrophenoxycarbonyl, fluorenyl-9-methoxycarbonyl, formyl, acetyl, propionyl, pivaloyl, 2-chloroacetyl, 2-bromoacetyl, 2,2,2-trifluoroacetyl, 2,2,2-trichloroacetyl, benzoyl, 4-chlorobenzoyl, 4-bromobenzoyl, 4-nitrobenzoyl, phthalimido, isovaleroyl or benzyloxymethylene, 4-nitrobenzyl, 2,4-dinitrobenzyl or 4-nitrophenyl. A preferred protective group for primary amines is phthalimide. Preferred protective groups for secondary amines are benzyloxycarbonyl and tert-butoxycarbonyl.

The amino protective groups are removed in a manner known per se, using, for example, hydrogenolytic, acidic or basic conditions, preferably acids, such as, for example, hydrochloric acid or trifluoroacetic acid, in inert solvents, such as ether, dioxane and methylene chloride.

In the context of the definition given above, a customary hydroxyl protective group is generally a protective group from the group: trimethylsilyl, triethylsilyl, triisopropylsilyl tert-butyl-dimethylsilyl, tert-butyldiphenylsilyl, dimethylhexylsilyl, dimethylthexylsilyl, trimethylsilylethoxycarbonyl, benzyl, triphenylmethyl (trityl), monomethoxytrityl (MMTr), dimethyloxytrityl (DMTr), benzyloxycarbonyl, 2-nitrobenzyl, 4-nitrobenzyl, 2-nitrobenzyloxycarbonyl, 4-nitrobenzyloxycarbonyl, tert-butyloxycarbonyl, 4-methoxybenzyl, 4-methoxybenzyloxycarbonyl, formyl, acetyl, trichloroacetyl, 2,2,2-trichloroethoxycarbonyl, 2,4-dimethoxybenzyl, 2,4-dimethoxybenzyloxycarbonyl, methoxymethyl, methylthiomethyl, methoxyethoxymethyl, [2-(trimethylsilyl)ethoxy]-methyl, 2-(methylthiomethoxy) ethoxycarbonyl, tetrahydropyranyl, benzoyl, N-succinimide, 4-methylbenzoyl, 4-nitrobenzoyl, 4-fluorobenzoyl, 4-chlorobenzoyl or 4-methoxybenzoyl. Preference is given to tert-butyl-dimethylsilyl.

The hydroxyl protective group is removed in a manner known per se, for example using acid, base or by addition of tetrabutylammonium fluoride.

Solvents suitable for the process are customary organic solvents which do not change under the reaction conditions. These include ethers, such as diethyl ether, dioxane, tetrahydrofuran, glycol dimethyl ether, or hydrocarbons, such as benzene, toluene, xylene, hexane, cyclohexane or mineral oil fractions, or halogenated hydrocarbons, such as dichloromethane, trichloromethane, carbon tetrachloride, dichloroethylene, trichloroethylene or chlorbenzene, or ethyl acetate, pyridine, dimethyl sulphoxide, dimethylformamide, N,N'-dimethylpropyleneurea (DMPU), N-methylpyrrolidone (NMP), acetonitrile, acetone or nitromethane. It is also possible to use mixtures of the solvents mentioned.

Bases suitable for the process according to the invention are, in general, inorganic or organic bases. These preferably include alkali metal hydroxides, such as, for example, sodium hydroxide or potassium hydroxide, alkaline earth metal hydroxides, such as, for example, barium hydroxide, alkali metal carbonates, such as sodium carbonates, potassium carbonate or caesium carbonate, alkaline earth metal carbonate, such as calcium carbonate, or alkali metal or alkaline earth metal alkoxides, such as sodium methoxide or potassium methoxide, sodium ethoxide or potassium ethoxide or potassium tert-butoxide, or organic amines, such as triethylamine, or heterocycles, such as 1,4-diazabicyclo[2.2.2]octane (DABCO), 1,8-diazabicyclo[5.4.0]undec-7-ene (DBU), 1,5-diazabicyclo[4.3.0]non-5-ene (DBN), pyridine, diaminopyridine, N-methylpiperidine or N-methyl-morpholine. It is also possible to use alkali metals such as sodium or their hydrides, such as sodium hydride, as bases.

Preferred solvents for process step [A] (II)+(III)→(IV) are diethyl ether, tetrahydrofuran and dimethylformamide. Particular preference is given to dimethylformamide.

Preferred bases for process step [A] (II)+(III)→(IV) are sodium hydride and sodium hydroxide.

In general, the base is employed in an amount of from 0.05 mol to 10 mol, preferably from 1 mol to 2 mmol, based on 1 mol of the compound of the formula (II).

The process step [A] according to the invention, (II)+(III)→(IV), is generally carried out in a temperature range of from −20° C. to +100° C., in particular from −20° C. to +80° C., preferably from 0° C. to +80° C.

The hydrolysis of carboxylic esters in process step [A] (IV)→(V) is carried out by customary methods by treating the esters in inert solvents with bases, and converting the salts which are initially formed into the free carboxylic acids, by treatment with acid. In the case of the tert-butyl esters, the hydrolysis is preferably carried out using acids.

Solvents suitable for the hydrolysis of the carboxylic esters are water or the organic solvents which are customary for ester hydrolysis. These preferably include alcohols, such as methanol, ethanol, propanol, isopropanol or butanol, or ethers, such as tetrahydrofuran or dioxane, dimethylformamide, dichloromethane or dimethyl sulphoxide. It is also possible to use mixtures of the solvents mentioned. Preference is given to water/tetrahydrofuran and, in the case of the reaction with trifluoroacetic acid, dichlormethane and, in the case of hydrogen chloride, tetrahydrofuran, diethyl ether, dioxane or water.

Suitable bases are the inorganic bases customary for hydrolysis. These preferably include alkali metal hydroxides or alkaline earth metal hydroxides, such as, for example, sodium hydroxide, lithium hydroxide, potassium hydroxide or barium hydroxide, or alkali metal carbonates, such as sodium carbonate or potassium carbonate, or sodium bicarbonate. Particular preference is given to using sodium hydroxide or lithium hydroxide.

Suitable acids are, in general, trifluoroacetic acid, sulphuric acid, hydrogen chloride, hydrogen bromide and acetic acid, or mixtures thereof, if appropriate with addition of water. Preference is given to hydrogen chloride or trifluoroacetic acid in the case of the tert-butyl esters and to hydrochloric acid in the case of the methyl esters.

When carrying out the hydrolyses, the base or the acid is generally employed in an amount of from 1 to 100 mol, preferably from 1.5 to 40 mol, based on 1 mol of ester.

The hydrolysis is generally carried out in a temperature range of from 0° C. to +100° C.

The amide formation in process step [A] (V)+(VI)→(I) is preferably carried out in the solvent dimethylformamide or dichloromethane.

Preferred auxiliaries used for the amide formation are customary condensing agents, such as carbodiimides, for example N,N'-diethyl-, N,N,'-dipropyl-, N,N'-diisopropyl-, N,N'-dicyclohexylcarbodiimide, N-(3-dimethylaminopropyl)-N'-ethylcarbodiimide hydrochloride (EDC), or carbonyl compounds, such as carbonyldiimidazole, or 1,2-oxazolium compounds, such as 2-ethyl-5-phenyl-1,2-oxazolium 3-sulphate or 2-tert-butyl-5-methyl-isoxazolium perchlorate, or acylaminocompounds, such as 2-ethoxy-1-ethoxycarbonyl-1,2-dihydroquinoline, or propanephosphonic anhydride, or isobutyl chloroformate, or bis-(2-oxo-3-oxazolidinyl)-phosphoryl chloride or benzotriazolyloxy-tri(dimethylamino)phosphonium hexafluorophosphate, or O-(benzotriazol-1-yl)-N,N,N',N'-tetra-methyluronium hexafluorophosphate (HBTU), 2-(2-oxo-1-(2H)-pyridyl)-1,1,3,3-tetramethyluronium tetrafluoroborate (TPTU) or O-(7-azabenzotriazol-1-yl)-N,N,N',N'-tetramethyluronium hexafluorophosphate (HATU), if appropriate in combination with further auxiliaries, such as 1-hydroxybenzotriazole or N-hydroxysuccinimide, and the bases used are preferably alkali metal carbonates, for example sodium carbonate or potassium carbonate, or sodium bicarbonate or potassium bicarbonate, or organic bases, such as trialkylamines, for example triethylamine, N-methylmorpholine, N-methylpiperidine or diisopropylethylamine. Particular preference is given to the combination of EDC, N-methylmorpholine and 1-hydroxybenzotriazole.

The amide formation is generally carried out a temperature range of from 0° C. to +100° C.

Solvents suitable for the acylation in process step [B] (VII)→(I) are the customary solvents which are inert under the reaction conditions; preference is given here to dimethylformamide and dichloromethane.

Suitable bases used for the acylation, if appropriate, are the customary inorganic or organic bases, preferably triethylamine.

The acylation is generally carried out in a temperature range of from 0° C. to +100° C.

The compounds of the formulae (II), (III), (VI), (VIII), (IX) and (X) are known or can be prepared by customary methods (cf. EP-A-0 725 061, EP-A-0 725 064, EP-A-0 581 003, EP-A-0 611 767, WO-A-00/73274).

The compounds of the formula (VII) can be prepared by converting compounds of the formula (II) with compounds of the formula (XI)

in which

A represents an oxygen atom or a group of the formula N—$R^5$, where $R^5$ is as defined above, and Y represents a suitable amino or hydroxyl protective group, if appropriate in the presence of a base, into compounds of the formula (XII)

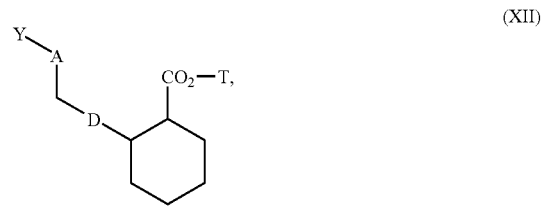

in which

A, D, T and Y are as defined above, in the next steps, analogously to the reaction steps described under [A], initially converting these by hydrolysis into compounds of the formula (XIII),

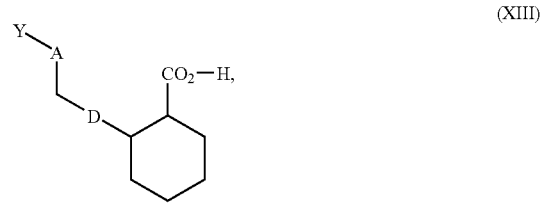

in which

A, D and Y are as defined above, then reacting with compounds of the formula (VI) to give compounds of the formula (XIV)

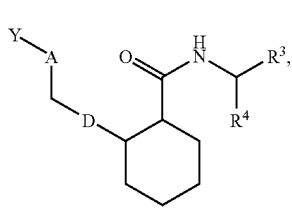

(XIV)

in which

A, D, Y, $R^3$ and $R^4$ are as defined above, and finally removing the protective group Y by customary methods.

The preparation of compounds of the formula (VII) can be illustrated in an exemplary manner by the equation below:

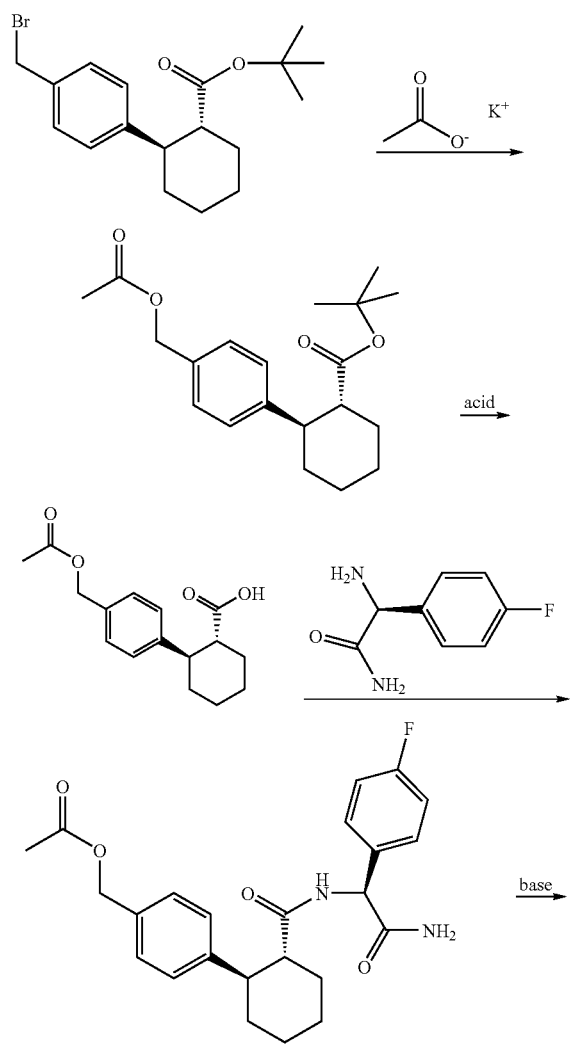

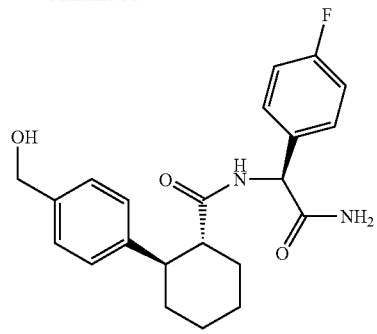

The conversion (II)+(XI)→(XII) is carried out in the customary solvents which are inert under the reaction conditions. Preference is given to acetonitrile.

Suitable bases, which are used for this reaction, if appropriate, are the customary inorganic or organic bases.

The reaction is generally carried out in a temperature range of from 0° C. to +100° C.

Surprisingly, the compounds of the formula (I) according to the invention have an unforeseeable useful pharmacological activity spectrum, combined with improved administration properties.

The compounds according to the invention act as adenosine-uptake inhibitors. They can be used for preparing medicaments for the prevention and/or treatment of peripheral and cardiovascular disorders caused by ischaemia, in particular for the acute and chronic treatment of ischaemic disorders of the cardiovascular system, such as, for example, coronary heart disease, stable and unstable angina pectoris, of peripheral and arterial occlusive diseases, of thrombotic vascular occlusions, of myocardial infarction and of reperfusion damage.

Moreover, owing to their potential to increase angiogenesis, they are particularly suitable for a permanent therapy of all occlusive diseases.

In addition, the compounds according to the invention, alone or in combination with other medicaments, can be used by oral or intravenous administration for preventing and/or treating cerebral ischaemia, stroke, reperfusion damage, brain trauma, oedema, spasms, epilepsy, respiratory arrest, cardiac arrest, Reye syndrome, cerebral thrombosis, embolism, tumours, haemorrhages, encephalomyelitis, hydroencephalitis, spinal injuries, post-operative brain damage, injuries of the retina or the optical nerve following glaucoma, ischaemia, hypoxia, oedema or trauma, and also in the treatment of schizophrenia, sleep disturbances and acute and/or chronic pain and also neurodegenerative disorders, in particular for the treatment of cancer-induced pain and chronic neuropathic pain, such as, for example, in cases of diabetic neuropathy, posttherpeutic neuralgia, peripheral nerve damage, central pain (for example as a result of cerebral ischaemia) and trigeminal neuralgia and other chronic pain, such as, for example, lumbago, lower back pain or rheumatic pain.

Adenosine-uptake inhibitors like the compounds according to the invention can furthermore also be used for treating hypertension and cardiac insufficiency, myocarditis, nephritis, pancreatitis, diabetic nephropathy, oedema and for potentiating the effect of nucleobase, nucleoside or nucleotide antimetabolites in cancer chemotherapy and antiviral (for example HIV) chemotherapy.

The compounds according to the invention have an increased solubility in water and an improved bioavailability, in particular when administered orally. These advantageous properties can, if appropriate, be improved even further with the aid of formulation auxiliaries and/or by adjusting a suitable pH. Good solubility in water and high bioavailability are, as is known, advantageous properties in medicinally active compounds and formulations; thus, the compounds according to the invention are, for example, particularly suitable for oral and intravenous administration.

A ASSESSMENT OF THE PHYSIOLOGICAL ACTIVITY

1. Determination of the Solubility

To determine the solubility, a precipitation method was used:

10 mg of the test substance are completely dissolved in 50 µl of DMSO (stock solution), 20 µl of this solution are added to 2000 µl of physiological saline. This solution, in turn, is shaken at 25° C. in a Thermomixer Comfort (from Eppendorf) at 1400 rpm for 24 hours for equilibration.

The precipitated fractions of the test substance are centrifuged off using a Biofuge 15 from Heraeus at 14,000 rpm for 5 min. 1300 µl of the supernatant are once more centrifuged using a Microfuge from Beckmann at 45,000 rpm=125,000 g.

10 µl of this centrifugation supernatant are then diluted with 1000 µl of DMSO, and this solution is measured by HPLC (Hewlett Packard 1090, method: gradient from 100% PBS buffer pH=4 to 10% buffer/90% acetonitrile over a period of 15 min, column: RP18).

Using a calibration curve, the measured peak area of the HPLC measurement is converted into the substance concentration. For the calibration curve, 20 µl of the stock solution are diluted successively with DMSO such that 5 concentrations of 2.5 mg/l to 2000 mg/l result. These solutions are likewise measured by HPLC (see method above), and the peak areas are plotted as a function of the concentrations.

2. Inhibition of the Adenosine Uptake in Rabbit Erythrocytes by the Compounds According to the Invention The capability of substances to influence the adenosine-uptake system is investigated by determining the inhibitory effect of the substances on functional adenosine uptake.

For the functional adenosine-uptake test, an erythrocyte preparation from rabbit blood is used. The blood is drawn intravenously using citrate (3 ml Monovette 9NC from Sarstedt) as anticoagulant. The blood is centrifuged at 3000 g for 5 min and the erythrocytes are suspended in 10 mM 3-(N-morpholino)propanesulphonic acid buffer (MOPS)/0.9% NaCL solution pH7.4. The suspension is diluted to one hundredth of the original blood volume. In each case, 990 µl of the suspension are admixed with 10 µl of a suitable concentration of the substance to be investigated, and the mixture is incubated at 30° C. for 5 min. 5 µl of a 4 mM adenosine solution are then added, and the mixture is incubated at 30° C. for another 15 min. The samples are then centrifuged at 3000 g for 5 min and in each case 700 µl of the supernatant are admixed with 28 µl of 70% strength $HClO_4$, allowed to stand in an ice bath for 30 min and centrifuged at 16,000 g for 3 min, and 350 µl of the sample are neutralized using 30 µl of 5N NaOH. 50 µl of the sample are applied to a column (Waters Symmetry C18 5 µm 3.9×150 mm). A Spherisorb ODS II 5 µm 4.6×10 mm column is used as precolumn. The mobile phase used is a gradient of 50 M $KH_2PO_4$/5 mM tributylamine pH7 (mobile phase A) and a mixture of mobile phase A/methanol 1/1 (mobile phase B). The gradient is from 10 to 40% B, at a flow rate of 0.5 ml/min. The adenosine which is present is quantified by its absorption at 260 nm, as are the hypoxanthine and inosine formed. The $IC_{50}$ is the concentration of active compound at which, 15 min after addition of adenosine, 50% of the adenosine concentration originally employed is still present.

Using this test, the $IC_{50}$ value determined for Example 1-1 was 30 nM, that for Example 1-3 was 20 nM, that for Example 1-14 was 30 nM, that for Example 1-33 was 40 nM, that for Example 2-1 was 20 nM and that for Example 2-18 was 20 nM.

3. In Vivo Test Model for Testing Adenosine-uptake Inhibitors

Adult FBI (Foxhound-Beagle-Irish-Setter) dogs (20–30 kg) are initially anaesthetized using a combination of trapanal 500 mg and alloferin 55 mg. Anaesthesia is maintained by infusion of a mixture of fentanyl 0.072 mg/kg, alloferin 0.02 mg/kg and dihydrobenzpyridyl 0.25 mg/kg×min. The animals are intubated and ventilated with a mixture of $O_2/N_2O$ 1/5 using an Engstrom ventilation pump at 16 breaths per min and a volume of 18–24 ml/kg. The body temperature is maintained at 38° C.±0.1° C. Arterial blood pressure is measured via a catheter in the femoral artery. Thoractomy is carried out on the left side at the fifth intercostal space. The lung is pushed back and fixed and a cut is made in the pericardium. A proximal section of the LAD distally to the first diagonal branch is exposed and a calibrated electromagnetic flow sensor (Gould Statham, model SP7515) is placed around the vessel and attached to a flow meter (Statham, model SP-2202). Distally to the flow sensor, a mechanical occluder is attached such that there are no branches in between flow sensor and occluder.

Using a catheter in the femoral vein, blood samples are taken and substances administered. A peripheral ECG is recorded using needles which are fixed subcutaneously. A microtip pressure manometer (Millar model PC-350) is pushed through the left atrium to measure the pressure in the left ventricle. Measurement of the heart frequency is triggered by the R wave of the ECG. During the entire experiment, the haemodynamic parameters and coronary flow are recorded using a multi-event recorder.

A four-minute occlusion causes reactive hyperaemia. The difference between the coronary flow under control conditions and the maximum flow during the reactive hyperaemia is measured. The time which is required to achieve half of this maximum flow in the drop is a suitable parameter to assess the reactive hyperaemia.

After a stabilization period of one hour, the experiment is started with a four-minute occlusion. Thirty minutes later, the substance is administered (i.v.) which is, after two minutes, followed by re-occlusion. The reactive hyperaemia after verum and placebo is compared.

4. Measurement of the Plasma Concentration of Adenosine-uptake Inhibitors Following Oral Administration to Mice Test principle: Following oral administration, blood samples are taken from the mice and the concentration of the active compound in the blood is measured by the functional inhibition of the adenosine uptake in rabbit erythrocytes.

The substances were administered in a dosage of 10 mg/kg and an administration volume of 10 ml/kg using a stomach tube. The solvent used was polyethylene glycol 400/ethanol 9:1. After one hour, the animals were anaesthetized and, by puncture of the heart, about 0.5 to 0.7 ml of blood were taken. The blood was precipitated in 5 times its volume of acetonitrile, kept in an ice bath for 30 minutes and then centrifuged at 16,000 g in an Eppendorf centrifuge for 5 minutes. At room temperature, the supernatant was evaporated to dryness in a Speedvac. The dried samples were initially wetted with 20 µl of DMSO and then admixed with 1 ml of 10 mM of 3-(N-morpholino)propanesulphonic acid buffer (MOPS)/0.9% aqueous sodium chloride solution pH7.4 and kept in an ultrasonic bath for 15 minutes. They were then centrifuged at 16,000 g for 5 minutes.

In each case, 500 µl of extract; 200 µl of extract and 300 µl of the above-mentioned buffer; 100 µl of extract and 400 µl of buffer; 50 µl of extract and 450 µl of buffer were mixed with a suspension of in each case 500 µl of rabbit erythrocytes. [The erythrocytes were isolated as described under Experiment 2 ("Inhibition of the adenosine uptake in rabbit erythrocytes") and diluted to fifty times the original blood volume]. As described under Experiment 2, adenosine was added after 5 minutes and the adenosine uptake was measured. The inhibition of adenosine uptake can be used to calculate the concentration of the inhibitor in the sample, since the inhibitory effect of the adenosine-uptake inhibitor was determined beforehand by a concentration curve using the method described in Experiment 2.

5. Mouse Angiogenesis Model

To test the effect of the adenosine-uptake inhibitors on collateralization and neovascularization, a mouse model for angiogenesis was developed. To this end, a femoral artery of the mouse is ligated at the upper end of the thigh. This induces chronic ischaemia of the hind leg in question. The other hind leg serves as individual control. To exclude residual flow through the ligated vessel, two ligatures are applied, and the vessel is cut in between. A few days after this operation, the treatment is started.

As a measurement parameter during the ongoing experiment, the temperatures of the paws of the two hind legs are measured. Owing to poorer circulation, the ischaemic hind leg has a lower absolute temperature. In each case, the temperature difference between the paws of the hind legs is calculated. This individual temperature difference is determined in various treatment groups as a function of the dose and in comparison with an untreated control. In this model, adenosine-uptake inhibitors significantly improve the circulation of the ischaemic hind leg in comparison with the corresponding controls.

The novel active compounds can be converted in a known manner into the customary formulations, such as tablets, sugar-coated tablets, pills, granules, aerosols, syrups, emulsions, suspensions and solutions. In this connection, the therapeutically active compound should in each case be present in a concentration of approximately 0.5 to 90% by weight of the total mixture, i.e. in amounts which are sufficient in order to achieve the dosage range indicated. In addition to the active compounds of the formula (I), the formulations may also comprise other pharmaceutically active compounds.

The formulations are prepared, for example, by extending the active compounds with inert non-toxic pharmaceutically suitable auxiliaries. Auxiliaries which may be mentioned are, for example: water, non-toxic organic solvents, such as, for example, paraffins, vegetable oils (for example sesame oil), alcohols (for example ethanol, glycerol), glycols (for example polyethylene glycol), solid carriers, such as natural or synthetic ground minerals (for example talc or silicates), sugar (for example lactose), emulsifiers, dispersants (for example polyvinylpyrrolidone) and glidants (for example magnesium sulphate).

Administration is carried out in a customary manner, preferably orally, transdermally, parenterally, perlingually, intravenously; particularly preferably orally or intravenously.

In general, it has proven advantageous in the case of intravenous administration to administer amounts of approximately 0.0001 to 10 mg/kg, preferably approximately 0.003 to 1 mg/kg, of body weight, to achieve effective results. In the case of oral administration, 0.1 to 20 mg/kg, preferably 0.3 to 10 mg/kg, of body weight are employed.

In spite of this, if appropriate, it may be necessary to depart from the amounts mentioned, namely depending on the body weight or on the type of administration route, on the individual response towards the medicament, the manner of its formulation and the time or interval at which administration takes place. Thus, in some cases it may be adequate to manage with less than the above-mentioned minimum amount, while in other cases the upper limit mentioned has to be exceeded. It may be advisable to divide this amount into a number of individual doses over the course of the day or to have a delayed release of active compound from the formulation over a relatively long period of time.

Below, the present invention is illustrated using the following preferred examples; however, these examples do not limit the invention in any way.

Unless indicated otherwise, all amounts are in percent by weight; in the case of solvent mixtures, ratios by volume are given.

B PREPARATION EXAMPLES

In the examples, the following abbreviations are used:
DMF=N,N-dimethylformamide
DMSO=dimethyl sulphoxide
TFA=trifluoroacetic acid
THF=tetrahydrofuran
EDC=N-(3-dimethylaminopropyl)-N'-ethylcarbodiimide hydrochloride
HOBT=1-hydroxybenzotriazole
DMAP=4-dimethylaminopyridine
TBDMS=tert-butyl-dimethylsilyl
BOC=tert-butyloxycarbonyl Starting Materials Example I tert-Butyl(1R,2R)-2-(4-bromomethyl-phenyl)-cyclohexane-1-carboxylate

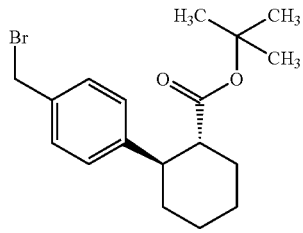

The intermediate is prepared analogously to the procedure for the racemate (U.S. Pat. No. 5,395,840, column 17). For purification, the resulting mixture is stirred with diethyl ether or diisopropyl ether.

Example II (2S)-2-Amino-4-(methylsulphonyl)butanamide hydrochloride

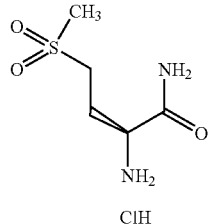

a) $N^2$-(tert-Butoxycarbonyl)-L-methionineamide

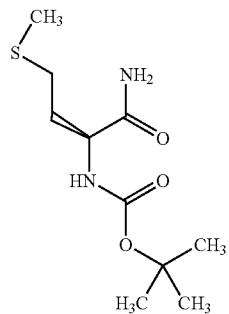

Under argon, 8.12 g (80.2 mmol) of triethylamine are added at −15° C. to 20 g (80.2 mmol) of N-Boc-L-methionine in 200 ml of THF. Over a period of 5 min, 10.4 ml (80,2 mmol) of isobutyl chloroformate are added dropwise, and the reaction mixture is stirred at −15° C. for 30 min. 40 ml of 2N ammonia solution in methanol are then added and the mixture is stirred in the cold for 30 min. The reaction mixture is filtered, the filtrate is concentrated under reduced pressure and the residue is stirred with 200 ml of water for 1 hour. The solid is filtered off with suction, dissolved in 250 ml of dichloromethane and washed twice with sat. sodium bicarbonate solution, and the solvent is again removed under reduced pressure. The residue is stirred with 0.7 l of petroleum ether, filtered off with suction and dried under high vacuum. This gives 12.86 g (64.6% of theory) of product as a crystalline substance.

$R_f$ (dichloromethane/methanol 10:1)=0.52.

MS (DCI, $NH_3$)=249 [(M+H)$^+$; 68%]; 266 [(M+NH$_4$)$^+$; 100%].

$^1$H-NMR (200 MHz, DMSO-$d_6$) δ [ppm]=1.38 (s, 9H); 1.65–1.95 (m, 2H); 2.04 (s, 3H); 2.44 (br. t, 2H); 3.93 (dt, 1H); 6.88 (d, 1H); 6.99 (br. s, 1H); 7.25 (br. s, 1H).

b) tert-Butyl(1S)-1-(aminocarbonyl)-3-(methylsulphonyl) propylcarbamate

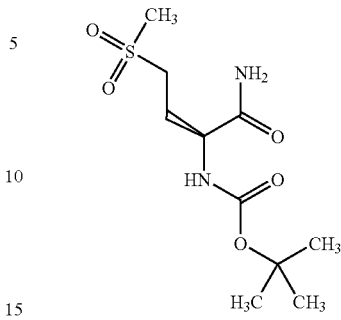

At 0° C., 29.9 g (98.7 mmol) of 3-chloroperbenzoic acid are added a little at a time to 12.25 g (49.3 mmol) of the compound from Example II-a in 50 ml of dichloromethane and 15 ml of methanol. After 2 hours, saturated sodium hydrogen sulphite solution is added and the mixture is stirred at room temperature for one hour. The phases are separated, the aqueous phase is extracted twice with dichloromethane and the combined organic phases are washed with saturated sodium bicarbonate solution. After drying over sodium sulphate and removal of the solvent under reduced pressure, 2.36 g (9.4%) of product are isolated. The sodium bicarbonate solution is then extracted twice with ethyl acetate, the combined organic phases are dried over sodium sulphate and the solvent is removed under reduced pressure, giving 7.38 g (46.6%) of product which still contains small amounts of benzoic acid. Concentration of the sodium bicarbonate solution and extraction of the residue with water and ethyl acetate, two extractions of the aqueous phase with ethyl acetate and drying of the extract over sodium sulphate give further 0.65 g (4.4%) of product. The combined product fractions are reacted further without further purification.

$R_f$ (dichloromethane/methanol 10:1)=0.49.

MS (ESI-pos.)=281 [(M+H)$^+$; 18%]; 303 [(M+Na)$^+$; 100%]; 583 [(2M+Na)$^+$; 50%].

$^1$H-NMR (200 MHz, DMSO-$d_6$) δ [ppm]=1.38 (s, 9H); 1.72–2.14 (m, 2H); 2.97 (s, 3H); 3.08 (m, 2H); 3.97 (m, 1H); 6.96 (d, 1H); 7.17 (br. s, 1H); 7.34 (br. s, 1H).

c) (2S)-2-Amino-4-(methylsulphonyl)butanamide hydrochloride

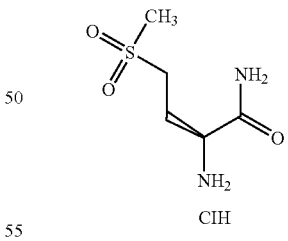

10.25 g (36.56 mmol) of the compound from Example II-b are dissolved in 20 ml of dioxane and stirred at room temperature with 50 ml 4N HCl in dioxane for 1 hour. A further 50 ml of 4 N HCl in dioxane are added, and the mixture is then stirred at room temperature overnight until the reaction has gone to completion. The precipitated solid is filtered off with suction and washed with petroleum ether. 6.96 g (62.5% of theory) of product are isolated as a colourless solid.

MS (ESI-pos.)=181 [(M+H)$^+$; 100%]; 203 [(M+Na)$^+$; 18%].

¹H-NMR (200 MHz, DMSO-d₆) δ [ppm]=2.19 (m, 2H); 3.04 (s, 3H); 3.22 (m, 2H); 3.89 (t, 1H); 7.67 (br.s, 1H); 8.08 (br. s, 1H); 8.38 (br. s, 3H).

General Alkylation Procedure [A]:

In a typical reaction, a solution of the compound of the formula (III) (4.12 mmol) in dry DMF (6 ml) is added to a suspension of sodium hydride (4.33 mmol) in dry DMF (6 ml). The mixture is stirred at room temperature for 30 min and at 40° C. for 30 min, and a suspension of the compound of the formula (II) (4.12 mmol) in dry DMF (15 ml) is then added. The mixture is stirred at room temperature for 24 hours and the crude mixture is then added to distilled water (200 ml). The milky emulsion is admixed with 2 g of sodium chloride and extracted four times with in each case 40 ml of diethyl ether. The combined organic phases are washed three times with in each case 30 ml of saturated sodium chloride solution and dried over sodium sulphate. Following chromatography (silica gel, cyclohexane:ethyl acetate), the product is obtained in a yield of from 60 to 96%.

General Procedure for Ester Hydrolysis [B]:

In a typical reaction, a solution of the ester of the formula (IV) (T=tert-Bu; 24.5 mmol) in 46 ml of dichloromethane is treated at room temperature with 23 ml of trifluoroacetic acid, and the mixture is stirred at room temperature for 16 hours. The solvent is removed under reduced pressure and the residue is taken up in 150 ml of diethyl ether, admixed with 200 ml of water and adjusted to pH12 using 1 N aqeuous sodium hydroxide solution (about 70 ml). The phases are separated and the aqueous phase washed twice with in each case 100 ml of diethyl ether. Using 5N hydrochloric acid, the mixture is acidified to pH3 and extracted three times with in each case 150 ml of dichloromethane. The combined organic phases are dried over sodium sulphate and concentrated under reduced pressure, giving the product in a yield of from 90 to 98%.

General Procedure for the Amide Formation [C]:

In a typical reaction, a mixture of the acid of the formula (V) (3.96 mmol), 1-hydroxybenzotriazole (3.96 mmol), EDC hydrochloride (4.75 mmol) and 4-dimethylaminopyridine (0.33 mmol) is admixed with dry DMF (10 ml). The mixture is stirred at room temperature for 5 minutes, and N-methylmorpholine (11.9 mmol) and (S)-phenylglycinamide hydrochloride (4.75 mmol) are then added. The mixture is stirred at room temperature for three days and chromatographed by reversed-phase HPLC, and the resulting product fraction is then lyophilized. The desired product is obtained in a yield of from 60 to 90%.

SYNTHESIS EXAMPLES

Example 1-1

N-{4-[(1R,2R)-2-({[(1S)-2-Amino-2-oxo-1-phenylethyl]amino}carbonyl)cyclohexyl]benzyl}-N-phenyl-4-morpholinecarboxamide

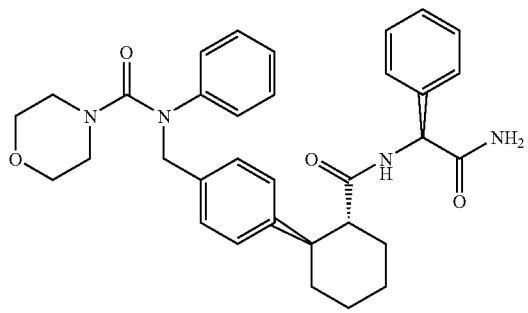

a) N-Phenyl-4-morpholinecarboxamide:

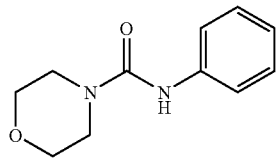

A solution of 7.44 g (85.4 mmol) of morpholine in 35 ml of abs. dichloromethane is cooled to 0° C. A solution of 9.25 g (77.7 mmol) of phenyl isocyanate in 15 ml of abs. dichloromethane is added dropwise (over a period of 5 min). The mixture is stirred at 0° C. for 30 min and at room temperature overnight. The product precipitates in the form of white crystals. The crystals are filtered off, washed twice with in each case 20 ml of diethyl ether and dried under high vacuum: 11.1 g of white crystals (69% of theory).
R$_f$ (dichloromethane/methanol 20:1)=0.38.
MS (DCI, NH₃)=224 (M+NH₄)⁺.
¹H-NMR (300 MHz, CDCl₃) δ [ppm]: 3.46 (4H, t), 3.72 (4H, t), 6.39 (1H, br. s), 7.05 (1H, tt), 7.23–7.38 (4H, m).
b) tert-Butyl(1R,2R)-2-(4-{[(4-morpholinylcarbonyl)(phenyl)amino]methyl}phenyl)cyclohexanecarboxylate:

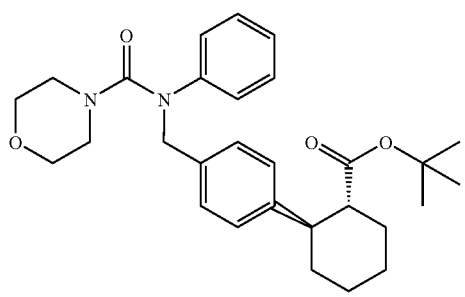

A solution of 850 mg (4.12 mmol) of the compound from Example 1-1a in 6 ml of DMF is added dropwise to a suspension of 173 mg (60% in mineral oil, 4.33 mmol) of sodium hydride in 4 ml of DMF. The mixture is stirred at room temperature for 30 min, and a suspension of 1.62 g (90%, 4.12 mmol) of tert-butyl(1R,2R)-2-(4-bromomethyl-phenyl)-cyclohexane-1-carboxylate from Example I in 15 ml of DMF is then added dropwise. The mixture is stirred at room temperature for 24 hours and the crude mixture is then added to 200 ml of dist. water. The milky emulsion is admixed with 2 g of sodium chloride and extracted four times with in each case 40 ml of diethyl ether. The combined organic phases are washed three times with in each case 30 ml of saturated sodium chloride solution and dried over sodium sulphate. The yellow oily crude product is purified by column chromatography (silica gel (70–230 mesh), gradient from cyclohexane to cyclohexane/ethyl acetate=2:1). This gives 1.89 g (96% of theory) of a colourless oil which solidifies under high vacuum.

$R_f$ (cyclohexane/acetic acid 2:1)=0.17.

MS (ESI)=479 (M+H)$^+$.

$^1$H-NMR (200 MHz, DMSO-d$_6$) δ [ppm]: 1.00 (9H, s), 1.20–1.53 (4H, m), 1.58–1.92 (4H, m), 2.30–2.60 (2H, m), 3.04–3.16 (4H, m), 3.33–3.43 (4H, m), 4.78 (2H, s), 6.98–7.32 (9H, m).

c) (1R,2R)-2-(4-{[(4-Morpholinylcarbonyl)(phenyl)amino]methyl}phenyl)cyclohexanecarboxylic acid:

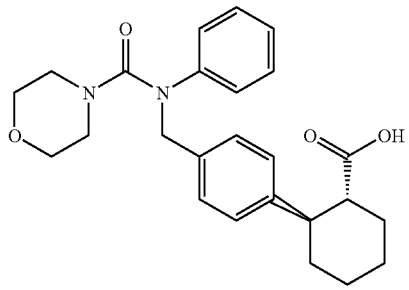

A solution of 11.75 g (24.5 mmol) of the compound from Example 1-1b in 46 ml of dichloromethane is treated with 23 ml of trifluoroacetic acid and stirred at room temperature for 16 hours. The solvent is distilled off under reduced pressure and the residue is, in each case twice, dissolved in 10 ml of dichloromethane, admixed with 30 ml of cyclohexane and concentrated under reduced pressure.

The residue is dissolved in 150 ml of diethyl ether, admixed with 200 ml of water and adjusted to pH12 using 70 ml of 1N NaOH. The phases are separated and the aqueous phase is washed twice with in each case 100 ml of diethyl ether. Using 5N hydrochloric acid, the mixture is acidified to pH=3 and extracted three times with in each case 150 ml of dichloromethane. The extracts are dried using sodium sulphate and the solvent is removed under reduced pressure. The residue is dissolved in 20 ml of diethyl ether and re-concentrated. This gives 10.1 g (95% of theory) of the product in the form of a white solid foam.

$R_f$ (dichloromethane/methanol 10:1)=0.39.

MS (ESI)=423 (M+H)$^+$.

$^1$H-NMR (200 MHz, DMSO-d$_6$) δ [ppm]: 1.20–1.54 (4H, m), 1.58–1.83 (3H, m), 1.85–2.03 (1H, m), 2.40–2.50 (2H, m), 3.05–3.18 (4H, m), 3.30–3.44 (4H, m), 4.77 (2H, s), 7.00–7.34 (9H, m), 11.74 (1H, br. s).

d) N-{4-[(1R,2R)-2-({[(1S)-2-Amino-2-oxo-1-phenylethyl]amino}carbonyl)cyclohexyl]benzyl}-N-phenyl-4-morpholinecarboxamide:

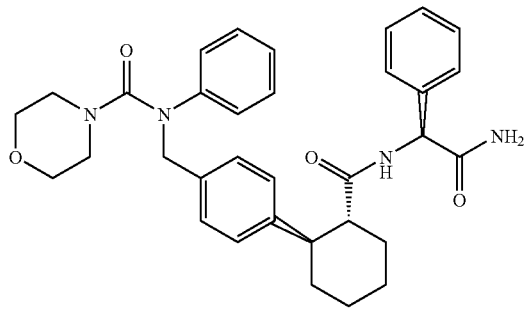

10 ml of abs. DMF are added to a mixture of 1.67 g (3.96 mmol) of the compound from Example 1-1c, 535 mg (3.96 mmol) of HOBT, 910 mg (4.75 mmol) of EDC and 40 mg of DMAP. The mixture is stirred at room temperature for 5 min until a clear solution is formed. 1.31 ml (1.20 g, 11.88 mmol) of N-methylmorpholine and 0.886 g (4.75 mmol) of L-phenylglycinamide hydrochloride are then added. The mixture is stirred at room temperature for 3 days and then separated directly by RP-HPLC (C18 Gromsil, 250 mm×30 mm, 50 ml/min, gradient water/acetonitrile 90:10→wasser/acetonitrile 10:90 in 30 min, 4.5 ml solution of the crude mixture per separation). The acetonitrile is removed under reduced pressure and the product separates out as a slightly pink sticky solid. It is frozen and lyophilized overnight. This gives 1.80 g (82% of theory) of the product as a white solid.

$R_f$ (dichloromethane/methanol 20:1)=0.20.

MS (ESI)=555 (M+H)$^+$.

$^1$H-NMR (300 MHz, DMSO-d$_6$) δ [ppm]: 1.20–1.54 (4H, m), 1.61–1.87 (4H, m), 2.59–2.70 (1H, m), 2.75–2.86 (1H, m), 3.12 (4H, t), 3.38 (4H, t), 4.79 (2H, s), 5.17 (1H, d), 6.80–6.89 (2H, m), 7.02–7.15 (1H, m), 7.28 (2H, t), 7.58 (1H, br. s), 7.96 (1H, d).

Example 1-34

(1R,2R)-2-(4-{[Acetyl(2-pyridinyl)amino]methyl}phenyl)-N-[(1S)-2-amino-2-oxo-1-phenylethyl]cyclohexanecarboxamide

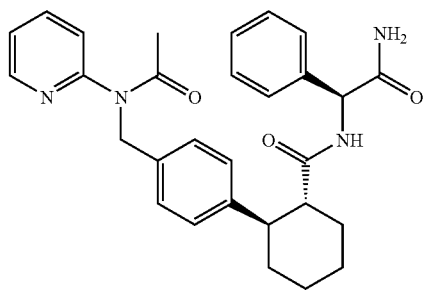

a) tert-Butyl(1R,2R)-2-(4-{[acetyl(2-pyridinyl)amino]methyl}phenyl)cyclohexanecarboxylate:

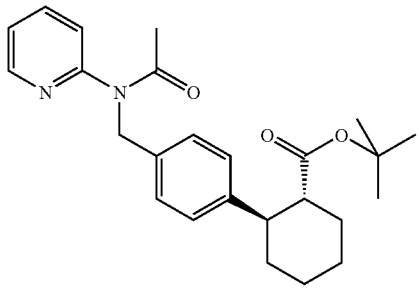

N-(2-Pyridinyl)acetamide (500 mg) is initially charged in dry DMF (25 ml), sodium hydride (116 mg, 80% in oil) is added at 0° C., and the mixture is stirred at room temperature for 30 min and at 40° C. for 30 min, cooled to 0° C. and treated a little at a time with the compound from Example I (1.36 g). The mixture is stirred at room temperature overnight and then hydrolyzed at 0° C. using water and extracted with diethyl ether. The organic phases are dried with magnesium sulphate and then concentrated. Subsequent chromatography (silica gel, cyclohexane:ethyl acetate 1:1 to 0:1) gives tert-butyl(1R,2R)-2-(4-{[acetyl(2-pyridinyl)amino]methyl}phenyl)cyclohexanecarboxylate as a colourless solid.

MS (ESI)=409 (M+H)$^+$.

$^1$H-NMR (300 MHz, DMSO-d$_6$): δ [ppm]: 1.0 (s, 9H), 1.2–1.49 (m, 5H), 1.62–1.77 (m, 3H), 1.81–1.9 (m, 1H), 2.02 (s, 3H), 2.35–2.45 (m, 1H), 5.02 (s, 2H), 7.05–7.13 (m, 4H), 7.2–7.27 (m, 1H), 7.37 (d, 1H), 7.48 (td, 1H), 8.43 (dd, 1H).

b) (1R,2R)-2-(4-{[Acetyl(2-pyridinyl)amino]methyl}phenyl)cyclohexanecarboxylic acid

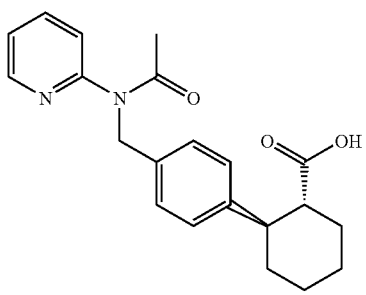

tert-Butyl(1R,2R)-2-(4-{[acetyl(2-pyridinyl)amino]methyl}phenyl)cyclohexanecarboxylate (0.44 g) is dissolved in dichloromethane (3.4 ml) and trifluoroacetic acid (3.4 ml), stirred at room temperature for 2 hours and then, at 0° C., made alkaline using aqueous sodium hydroxide solution. The aqueous phase is washed with dichloromethane, acidified with hydrochloric acid and extracted with dichloromethane. The organic extracts are dried over sodium sulphate and concentrated. This gives (1R,2R)-2-(4-{[acetyl(2-pyridinyl)amino]methyl}phenyl)cyclohexanecarboxylic acid (445 mg) as a viscous yellow oil.

MS (ESI)=353 (M+H)$^+$; 375 (M+Na)$^+$.

$^1$H-NMR (300 MHz, DMSO-d$_6$): δ [ppm]: 1.21–1.5 (m, 4H), 1.62–1.8 (m, 3H), 1.89–1.98 (m, 1H), 2.0 (s, 3H), 2.4–2.5 (m, 1H), 2.55–2.7 (m, 1H), 5.0 (s, 2H), 7.05–7.13 (m, 4H), 7.24–7.3 (1H), 7.43 (d, 1H), 7.84 (td, 1H), 8.47 (dd, 1H), 11.6 (broad s, 1H).

c) (1R,2R)-2-(4-{[Acetyl(2-pyridinyl)amino]methyl}phenyl)-N-[(1S)-2-amino-2-oxo-1-phenylethyl]cyclohexanecarboxamide

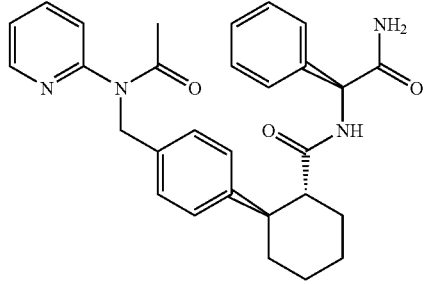

(1R,2R)-2-(4-{[Acetyl(2-pyridinyl)amino]methyl}phenyl)cyclohexanecarboxylic acid (0.44 g) is suspended in DMF (15 ml), (2S)-2-amino-2-phenylethanamide (0.37 g), triethylamine (0.68 ml), 1-hydroxybenzotriazole (0.18 g) and EDC hydrochloride (0.27 g) are admixed and the mixture is stirred at room temperature for 2 days. The suspension is diluted with water and extracted with dichloromethane and the organic phases are washed with saturated sodium chloride solution, dried over sodium sulphate and concentrated. Chromatography (silica gel, dichloromethane:methanol:saturated aqueous ammonia solution=50:1:0.05 to 20:1:0.05 gives (1R,2R)-2-(4-{[acetyl(2-pyridinyl)amino]methyl}phenyl)-N-[(1S)-2-amino-2-oxo-1-phenylethyl]cyclohexanecarboxamide (0.39 g) as a colourless solid.

R$_f$ (dichloromethane/methanol/saturated aqueous ammonia solution 40:2:0.1)=0.43.

MS (ESI)=485 (M+H)$^+$; 507 (M+Na)$^+$.

$^1$H-NMR (300 MHz, DMSO-d$_6$): δ [ppm]: 1.23–1.52 (m, 4H), 1.65–1.86 (m, 4H), 2.01 (s, 3H), 2.59–2.84 (m, 2H), 5.04 (s, 2H), 5.15 (d, 1H), 6.78 (d, 2H), 6.97–7.11 (m, 8H), 7.24–7.29 (m, 1H), 7.43 (d, 1H), 7.57 (s, 1H), 7.80 (td, 1H), 7.93 (d, 1H), 8.45–8.48 (m, 1H).

The compounds listed in Table 1 below are prepared in an analogous manner:

TABLE 1
| Example | Structure | | Retention time (method) |
|---|---|---|---|
| 1-2 | 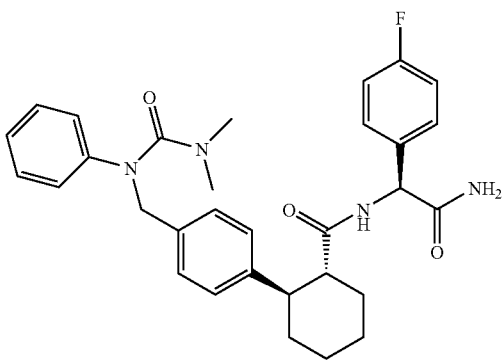 | chiral | 7.49 (D) |
| 1-3 | 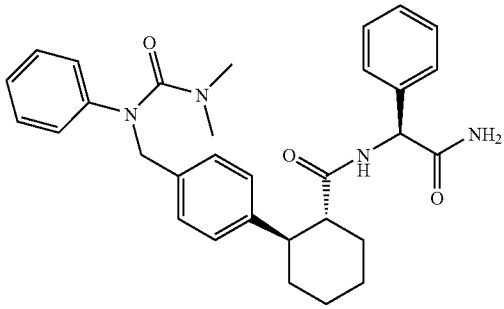 | chiral | 7.17 (D) |
| 1-4 | 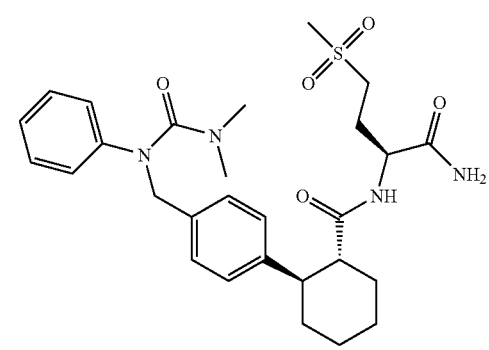 | chiral | 4.15 (A) |
| 1-5 | 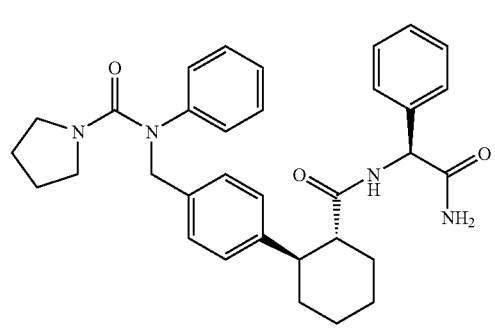 | chiral | 4.63 (A) |

TABLE 1-continued

| Example | Structure | | Retention time (method) |
|---|---|---|---|
| 1-6 | 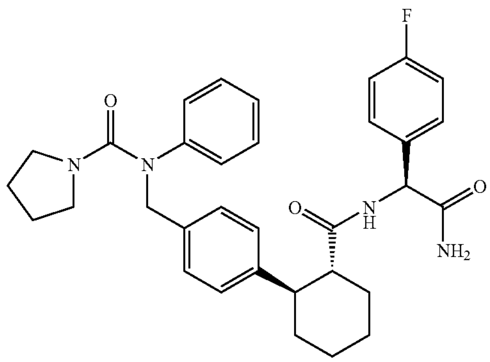 | chiral | 4.69 (A) |
| 1-7 | 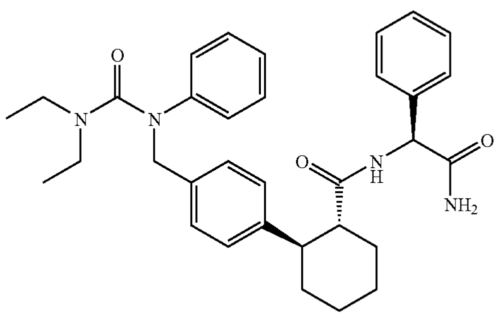 | chiral | 4.80 (A) |
| 1-8 | 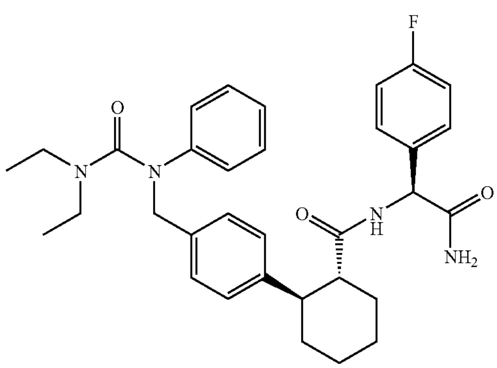 | chiral | 4.86 (A) |
| 1-9 | 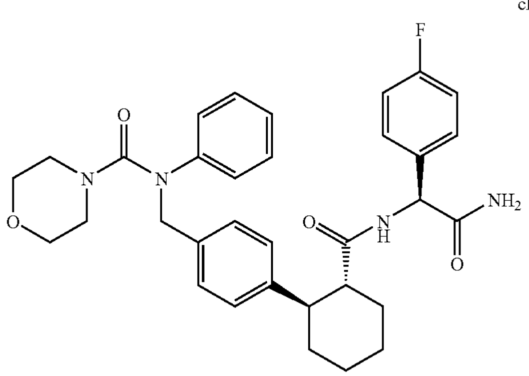 | chiral | 4.44 (A) |

TABLE 1-continued

| Example | Structure | | Retention time (method) |
|---------|-----------|---|-------------------------|
| 1-10 | 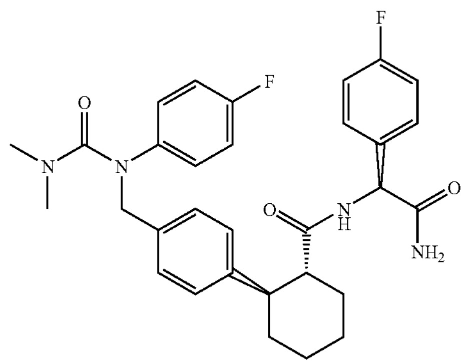 | chiral | 4.57 (A) |
| 1-11 | 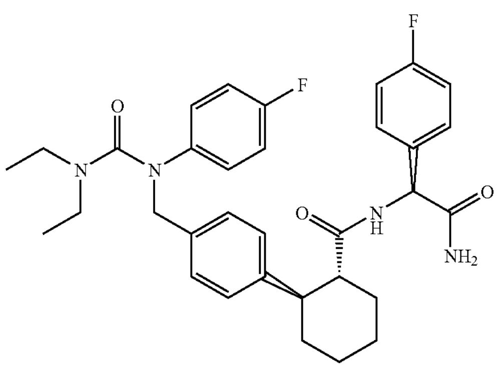 | chiral | 4.87 (A) |
| 1-12 | 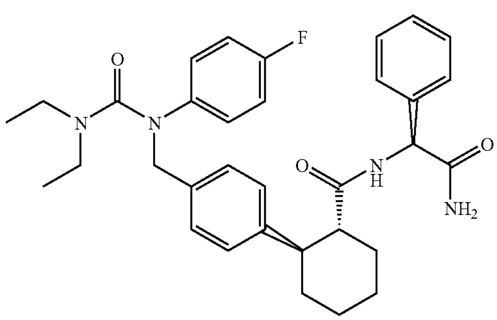 | chiral | 4.82 (A) |
| 1-13 | 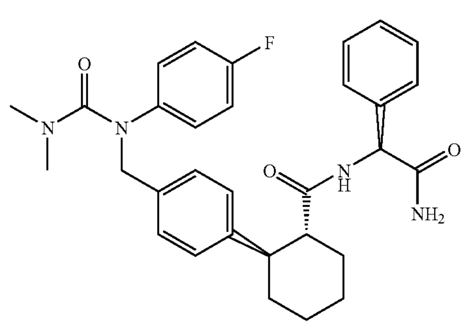 | chiral | 4.52 (A) |

TABLE 1-continued
| Example | Structure | | Retention time (method) |
|---|---|---|---|
| 1-14 | 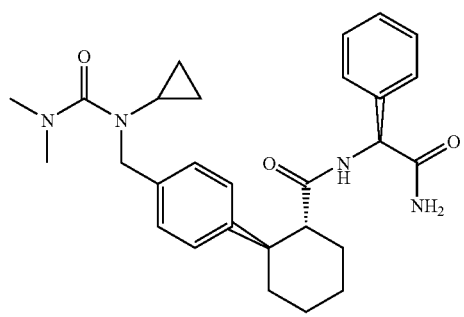 | chiral | 4.15 (A) |
| 1-15 | 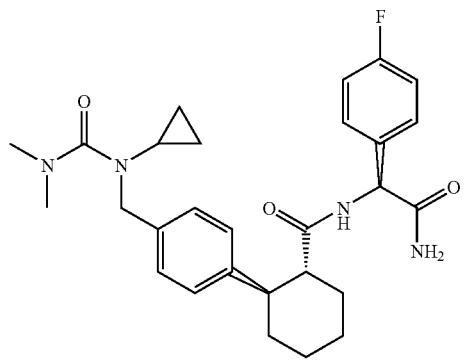 | chiral | 4.21 (A) |
| 1-16 | 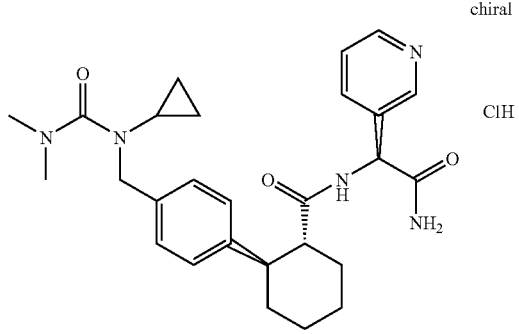 | chiral ClH | 4.01 (A) |
| 1-17 | 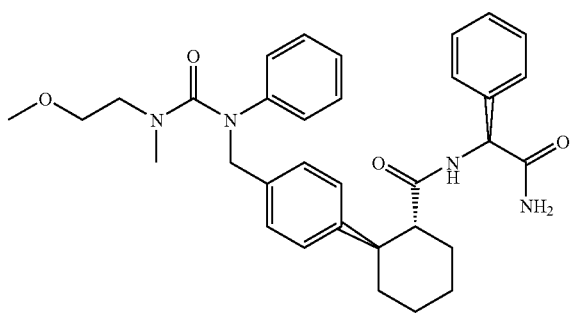 | chiral | 4.52 (A) |

TABLE 1-continued
| Example | Structure | | Retention time (method) |
|---|---|---|---|
| 1-18 | 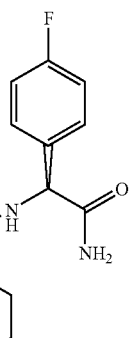 | chiral | 4.58 (A) |
| 1-19 | 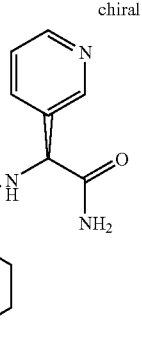 | chiral | 4.33 (A) |
| 1-20 | 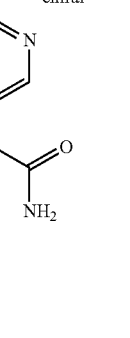 | chiral | 4.30 (A) |
| 1-21 | 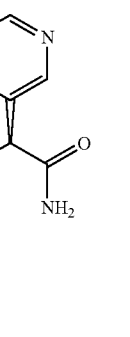 | chiral | 4.53 (A) |

TABLE 1-continued
| Example | Structure | | Retention time (method) |
|---|---|---|---|
| 1-22 | 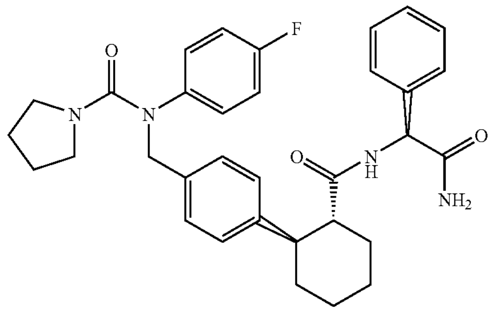 | chiral | 4.64 (A) |
| | 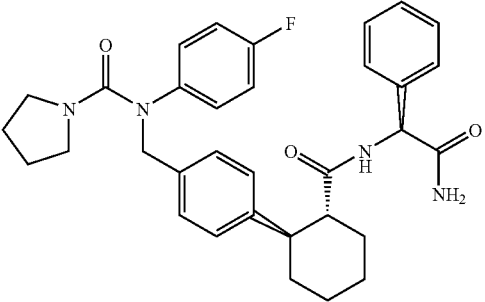 | | |
| 1-23 | 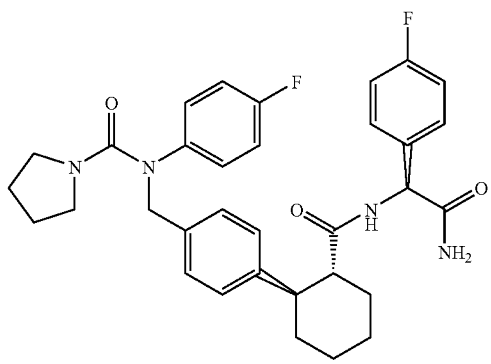 | chiral | 4.69 (A) |
| | 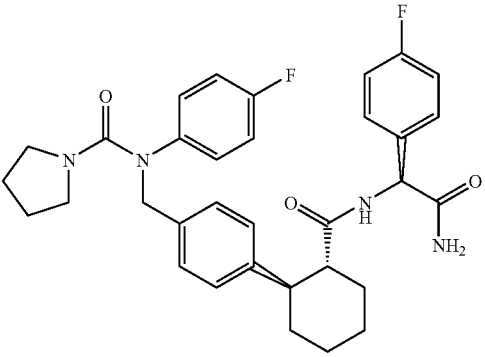 | | |
| 1-24 | 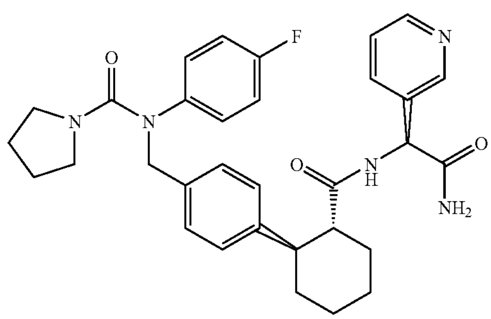 | chiral | 4.43 (B) |
| | 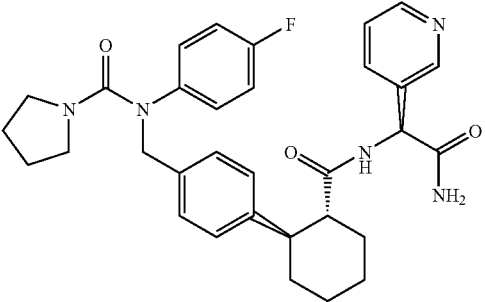 | | |
| 1-25 | 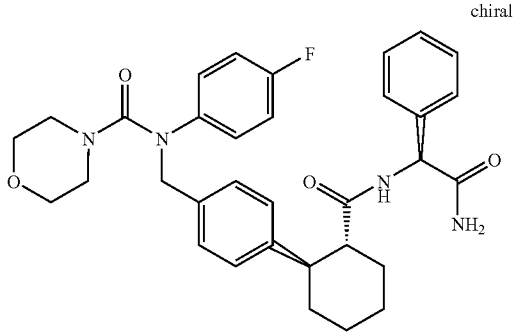 | chiral | 4.41 (A) |
| | 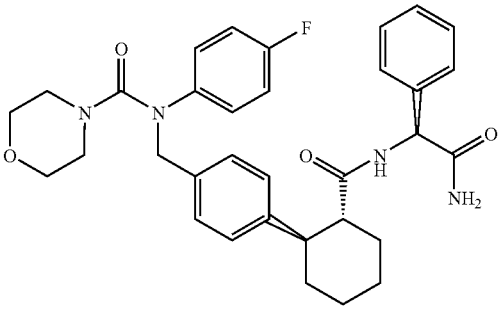 | | |

TABLE 1-continued
| Example | Structure | | Retention time (method) |
|---|---|---|---|
| 1-26 | 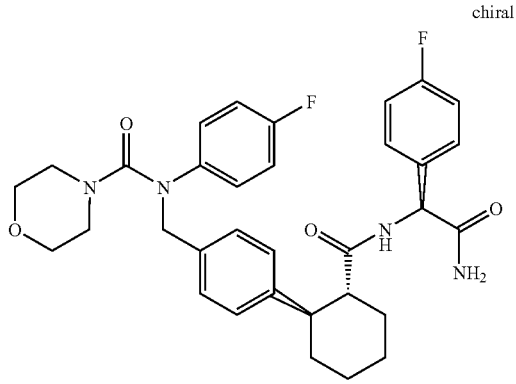 | chiral | 4.46 (A) |
| 1-27 | 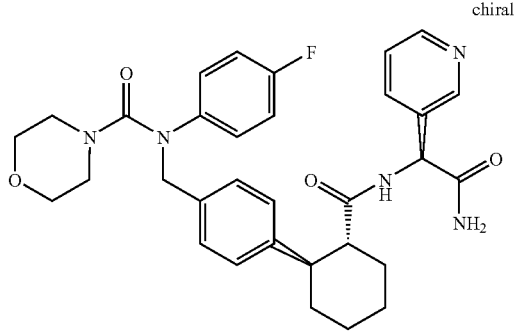 | chiral | 4.17 (B) |
| 1-28 | 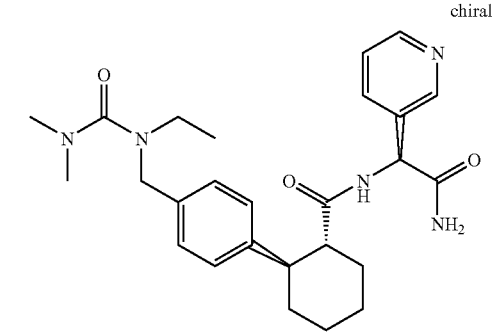 | chiral | 3.96 (A) |
| 1-29 | 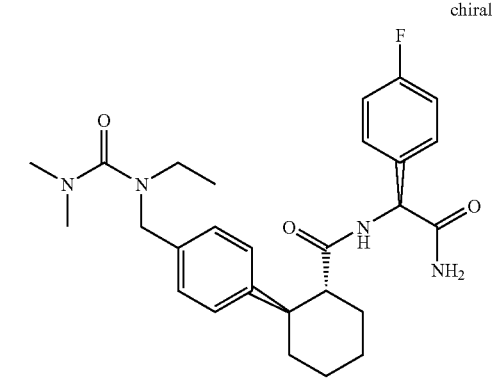 | chiral | 4.18 (A) |

TABLE 1-continued
| Example | Structure | Retention time (method) |
|---|---|---|
| 1-30 | 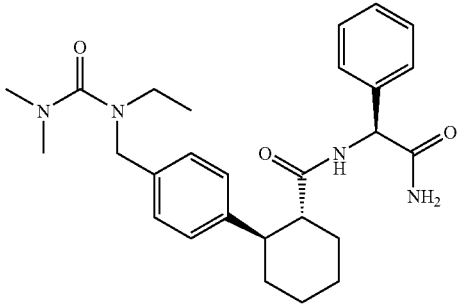 chiral | 4.12 (A) |
| 1-31 | 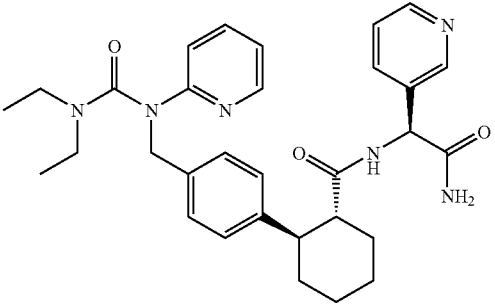 chiral | 3.67 (A) |
| 1-32 | 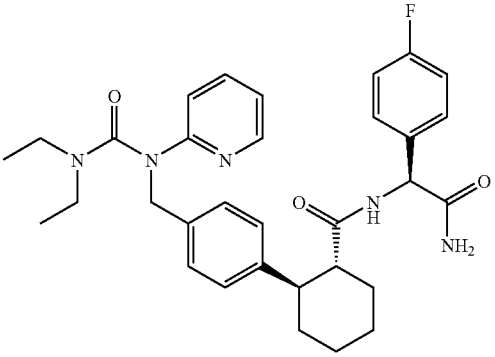 chiral | 3.91 (A) |
| 1-33 | 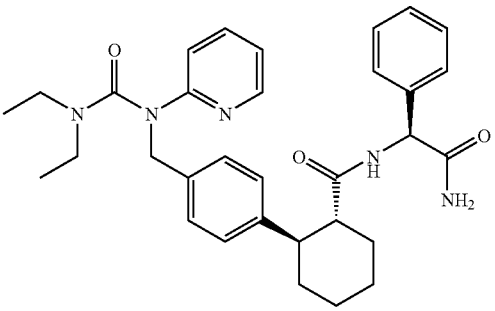 chiral | 3.87 (A) |

Example 2-1

(1R,2R)-N-[(1S)-2-Amino-1-(4-fluorophenyl)-2-oxoethyl]-2-(4-{[{[ethyl(2-hydroxyethyl)amino]carbonyl}(4-fluorophenyl)amino]methyl}phenyl)cyclohexanecarboxamide

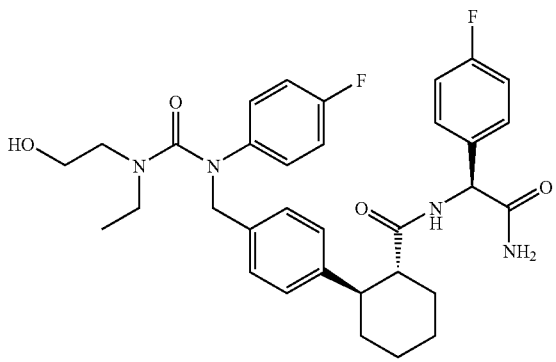

a) N-Ethyl-N'-(4-fluorophenyl)-N-(2-hydroxyethyl)urea:

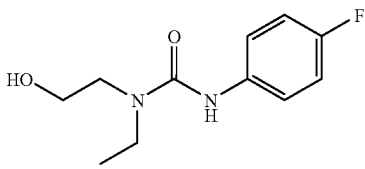

At 0° C., 1.00 g (7.29 mmol) of 4-fluorophenyl isocyanate are added dropwise to a solution of 720 mg (8.02 mmol) of N-ethylethanolamine in 4 ml of dichloromethane. After 10 min at 0° C., the mixture is stirred at room temperature for 2 hours. The solution is concentrated under reduced pressure and the residue is dissolved in 20 ml of dichloromethane and treated with 400 mg of Amberlyst® 15. The mixture is stirred at room temperature for 15 min, filtered and concentrated under reduced pressure. This gives 1.50 g (91% of theory) of the product as a yellow oil.

$R_f$ (dichloromethane/methanol 40:1)=0.29.
MS (ESI)=227 (M+H)$^+$.
$^1$H-NMR (400 MHz, DMSO-d$_6$) δ [ppm]: 1.07 (3H, t), 3.28–3.39 (4H, m), 3.56 (2H, t), 5.16 (1H, t), 7.0–7.09 (2H, m), 7.37–7.43 (2H, m), 8.44 (1H, br. s).

b) N-(2-{[tert-Butyl(dimethyl)silyl]oxy}ethyl)-N-ethyl-N'-(4-fluorophenyl)-urea:

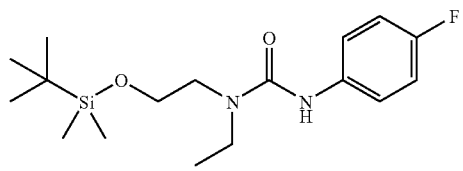

1.30 ml (9.35 mmol) of triethylamine and a solution of 1.03 g (6.86 mmol) of TBDMS chloride in 5 ml of dichloromethane are added to a solution of 1.41 g (6.23 mmol) of the compound from Example 2-1a in a mixture of 10 ml of dichloromethane and 1.5 ml of abs. DMF. The mixture is stirred at room temperature for 18 hours and diluted with 30 ml of dichloromethane. The mixture is washed three times with in each case 30 ml of water, dried with sodium sulphate and concentrated under reduced pressure. This gives 2.00 g (94% of theory) of a colourless oil.

$R_f$ (dichloromethane/methanol 40:1)=0.74.
MS (ESI)=341 (M+H)$^+$.
$^1$H-NMR (200 MHz, DMSO-d$_6$) δ [ppm]: 0.00 (6H, s), 0.81 (9H, s), 1.04 (3H, t), 3.27–3.41 (4H, m), 3.67 (2H, t), 6.94–7.09 (2H, m), 7.34–7.46 (2H, m), 8.15 (1H, br. s).

c) tert-Butyl(1R,2R)-2-{4-[4-ethyl-2-(4-fluorophenyl)-8,8,9,9-tetramethyl-3-oxo-7-oxa-2,4-diaza-8-siladec-1-yl]phenyl}cyclohexanecarboxylate:

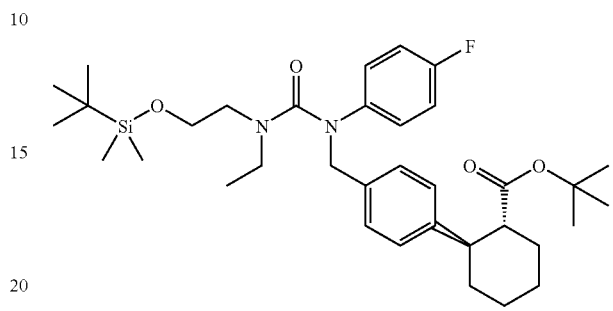

A solution of 443 mg (1.30 mmol) of the compound from Example 2-1b in 3 ml of DMF is added dropwise to a suspension of 54.6 mg (60% in mineral oil, 1.37 mmol) of sodium hydride in 1 ml of DMF. The mixture is stirred at room temperature for 45 min, and a suspension of 510 mg (90%, 1.30 mmol) of tert-butyl(1R,2R)-2-(4-bromomethyl-phenyl)-cyclohexane-1-carboxylate from Example I in 3 ml of DMF is then added dropwise. The mixture is stirred at room temperature for 4 hours and then diluted with 50 ml of water and extracted three times with in each case 30 ml of diethyl ether. The combined organic phases are washed with 100 ml of saturated sodium chloride solution and dried over sodium sulphate. The crude product is purified by column chromatography (silica gel (70–230 mesh), gradient: from cyclohexane to cyclohexane/ethyl acetate 5:1). This gives 621 mg (78% of theory) of the product as a colourless oil.

$R_f$ (dichloromethane/methanol 40:1)=0.78.
MS (ESI)=613 (M+H)$^+$.
$^1$H-NMR (200 MHz, DMSO-d$_6$) δ [ppm]: 0.06 (6H, s), 0.83 (3H, t), 0.84 (9H, s), 0.99 (9H, s), 1.20–1.52 (4H, m), 1.59–1.92 (4H, m), 2.32–2.61 (2H, m), 3.06 (2H, q), 3.15 (3H, t), 3.51 (2H, t), 4.67 (2H, s), 7.00–7.22 (8H, m).

d) tert-Butyl(1R,2R)-2-(4-{[{[ethyl(2-hydroxyethyl)amino]carbonyl}(4-fluorophenyl)amino]methyl}phenyl)cyclohexancarboxylate:

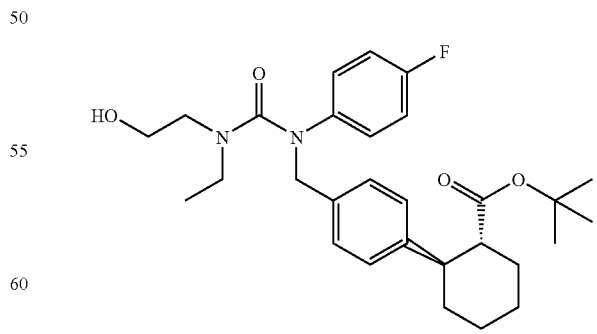

345 μl (1.20 mmol) of a 1.1 M solution of tetra-n-butylammonium fluoride in THF are added to a solution of 246 mg (0.40 mmol) of the compound from Example 2-1c in 20 ml of THF. The mixture is stirred at room temperature for 4 hours and then diluted with 100 ml of diethyl ether. The mixture is washed three times with in each case 25 ml of a semisaturated sodium chloride solution and once with 20 ml of a sat. sodium chloride solution. The combined wash solutions are extracted with 20 ml of diethyl ether and the combined organic phases are dried with sodium sulphate. The crude product is purified by column chromatography (silica gel (70–230 mesh), gradient: from cyclohexane to cyclohexane/ethyl acetate 1:1). Yield: 201 mg of a colourless oil (95% of theory).

$R_f$ (cyclohexane/acetic acid 1:1)=0.29.

MS (ESI)=499 (M+H)$^+$.

$^1$H-NMR (200 MHz, DMSO-$d_6$) δ [ppm]: 0.83 (3H, t), 1.00 (9H, s), 1.20–1.52 (4H, m), 1.60–1.92 (4H, m), 2.32–2.61 (2H, m), 2.91–3.17 (4H, m), 3.36 (2H, t), 4.61 (1H, t), 4.66 (2H, s), 7.00–7.22 (8H, m).

e) (1R,2R)-2-(4-{[{[Ethyl(2-hydroxyethyl)amino]carbonyl} (4-fluorophenyl)amino]methyl}phenyl) cyclohexanecarboxlic acid:

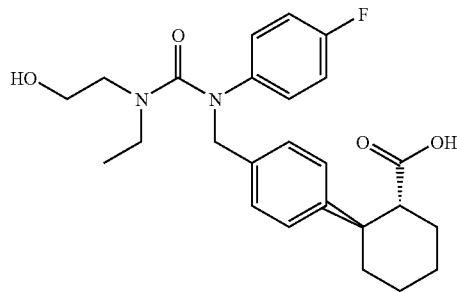

200 mg (0.40 mmol) of the compound from Example 2-1d are dissolved in 2 ml of dichloromethane and treated with 1 ml of trifluoracetic acid. The solution is stored at 6° C. for 16 hours, and 15 ml of 1N sodium hydroxide solution and 20 ml of water are then added. The mixture is washed twice with in each case 20 ml of diethyl ether and adjusted to pH3–4 using 1N hydrochloric acid. The mixture is extracted three times with in each case 30 ml of dichloromethane and the extracts are dried with sodium sulphate and concentrated. The residue is taken up in 4 ml of diethyl ether and re-concentrated. The oil that is initially obtained turns into a white solid foam. Yield: 146 mg (78% of theory, 94% purity according to HPLC).

$R_f$ (dichloromethane/methanol 40:1)=0.44.

MS (ESI)=443 (M+H)$^+$.

$^1$H-NMR (200 MHz, DMSO-$d_6$) δ [ppm]: 0.83 (3H, t), 1.20–1.52 (4H, m), 1.60–1.82 (3H, m), 1.88–2.02 (1H, m), 2.40–2.72 (2H, m), 2.99–3.20 (4H, m), 3.34 (2H, t), 4.64 (2H, s), 7.03–7.20 (8H, m), 11.70 (1H, br. s).

f) (1R,2R)-N-[(1S)-2-Amino-1-(4-fluorophenyl)-2-oxoethyl]-2-(4-{[{[ethyl(2-hydroxyethyl)amino]carbonyl} (4-fluorophenyl)amino]methyl}phenyl) cyclohexanecarboxamide:

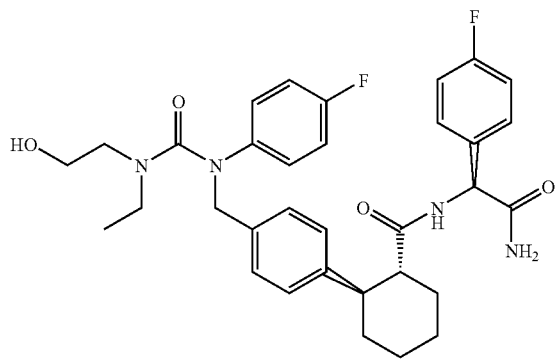

0.90 ml of abs. DMF is added to a mixture of 44.3 mg (0.100 mmol) of the compound from Example 2-1e, 13.5 mg (0.100 mmol) of HOBT, 23.0 mg (0.120 mmol) of EDC and 1 mg of DMAP. The mixture is stirred at room temperature for 5 min until a clear solution is formed. 22.0 μl (20.2 mg, 0.200 mmol) of N-methylmorpholine and 30.7 mg (0.150 mmol) of L-4-fluorophenylglycinamide hydrochloride are then added. The mixture is stirred at room temperature for 3 days and then separated directly by RP-HPLC (C18 Gromsil, 50×20 mm, 25 ml/min, gradient water/acetonitrile 90:10→water/acetonitrile 10:90 over 8 min). The acetonitrile is removed under reduced pressure and the product precipitates out in the form of white flakes. The product is frozen and lyophilized overnight. This gives 37.9 mg (64% of theory) of the product as a white solid.

$R_f$ (dichloromethane/methanol 10:1)=0.37.

MS (ESI)=593 (M+H)$^+$.

$^1$H-NMR (300 MHz, DMSO-$d_6$) δ [ppm]: 0.82 (3H, t), 1.20–1.53 (4H, m), 1.61–1.87 (4H, m), 2.56–2.69 (1H, m), 2.75–2.87 (1H, m), 3.05 (2H, q), 3.13 (2H, t), 4.68 (2H, dd), 5.13–5.20 (1H, m), 6.79–6.87 (2H, m), 6.92 (2H, t), 7.02–7.18 (9H, m), 7.63 (1H, br s), 8.05 (1H, d).

Example 2-18

(1R,2R)-N-[(1S)-2-Amino-1-phenyl-2-oxoethyl]-2-(4-{[{[ethyl(2-hydroxyethyl)-amino]carbonyl} (phenyl)amino]methyl}phenyl) cyclohexanecarboxamide

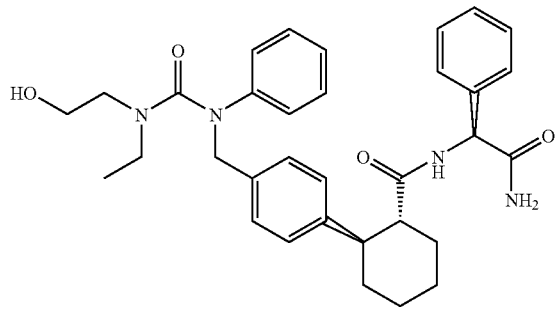

a) N-Ethyl-N'-phenyl-N-(2-hydroxyethyl)urea:

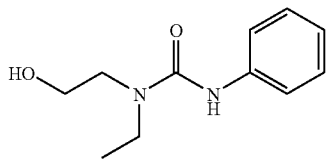

At 0° C., a solution of 1.00 g (8.39 mmol) of phenyl isocyanate in 2 ml of dichloromethane is added dropwise to a solution of 820 mg (9.23 mmol) of N-ethylethanolamine in 4 ml of dichloromethane. After 10 min at 0° C., the mixture is stirred at room temperature for 16 hours. The solution is concentrated under reduced pressure and the solid residue is washed three times with in each case 20 ml of diethyl ether. This gives 1.71 g (98% of theory) of the product as a white solid.

$R_f$ (dichloromethane/methanol 20:1)=0.17.
MS (ESI)=(208 M)$^+$.
$^1$H-NMR (300 MHz, DMSO-d$_6$) δ [ppm]: 1.08 (3H, t), 3.28–3.39 (4H, m), 3.57 (2H, q), 5.17 (1H, t), 6.91 (1H, t), 7.22 (2H, t), 7.39 (2H, d), 8.44 (1H, br. s).

b) N-(2-{[tert-Butyl(dimethyl)silyl]oxy}ethyl)-N-ethyl-N'-phenylurea:

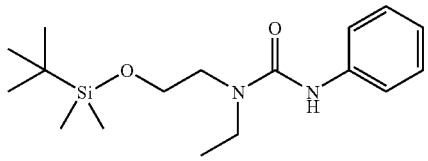

1.70 ml (12.2 mmol) of triethylamine and a solution of 1.35 g (8.93 mmol) of TBDMS chloride in 5 ml of dichloromethane are added to a solution of 1.69 g (8.12 mmol) of the compound from Example 2-18a in a mixture of 10 ml of dichloromethane and 3.0 ml abs. dimethylformamide. The mixture is stirred at room temperature for 18 hours and diluted with 100 ml of diethyl ether. The mixture is washed three times with in each case 30 ml of water, dried with sodium sulphate and concentrated under reduced pressure. This gives 2.62 g (95% of theory) as a colourless oil.

$R_f$ (dichloromethane/methanol 20:1)=0.67.
MS (ESI)=323 (M+H)$^+$.
$^1$H-NMR (200 MHz, DMSO-d$_6$) δ [ppm]: 0.04 (6H, s), 0.85 (9H, s), 1.08 (3H, t), 3.33–3.45 (4H, m), 3.72 (2H, t), 6.92 (1H, t), 7.22 (2H, t), 7.42 (2H, d), 8.13 (1H, br. s).

c) tert-Butyl(1R,2R)-2-{4-[4-ethyl-2-phenyl-8,8,9,9-tetramethyl-3-oxo-7-oxa-2,4-diaza-8-siladec-1-yl]phenyl}cyclohexanecarboxylate:

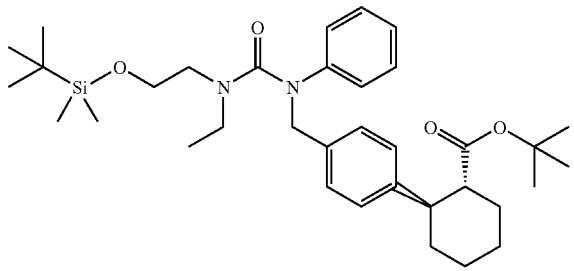

A solution of 419 mg (1.30 mmol) of the compound from Example 2-18b in 3 ml of DMF is added dropwise to a suspension of 54.6 mg (60% in mineral oil, 1.37 mmol) of sodium hydride in 1 ml of DMF. The mixture is stirred at room temperature for 15 min, and a suspension of 535 mg (85.8%, 1.30 mmol) of tert-butyl(1R,2R)-2-(4-bromomethyl-phenyl)cyclohexane-1-carboxylate from Example I in 4 ml of DMF is then added dropwise. The mixture is stirred at room temperature for 20 hours and then diluted with 50 ml of water and extracted three times with in each case 30 ml of diethyl ether. The combined organic phases are washed with 100 ml of saturated sodium chloride solution and dried over sodium sulphate. The crude product is purified by column chromatography (silica gel (70–230 mesh), dichloromethane/ethanol 40:1). This gives 757 mg (91% of theory) of the product as a colourless oil.

$R_f$ (petroleum ether/ethyl acetate 4:1)=0.57.

MS (ESI)=595 (M+H)$^+$.

$^1$H-NMR (200 MHz, DMSO-d$_6$) δ [ppm]: 0.00 (6H, s), 0.80–0.85 (12H, m), 0.99 (9H, s), 1.20–1.52 (4H, m), 1.59–1.92 (4H, m), 2.32–2.61 (2H, m), 3.06 (2H, q), 3.15 (3H, t), 3.51 (2H, t), 4.67 (2H, s), 7.00–7.27 (9H, m).

d) tert-Butyl(1R,2R)-2-(4-{[{[ethyl(2-hydroxyethyl)amino]carbonyl}(phenyl)amino]methyl}phenyl)cyclohexanecarboxylate:

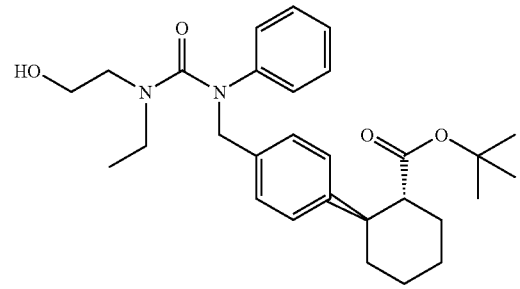

350 µl (1.22 mmol) of a 1.1 M solution of tetra-n-butylammonium fluoride in THF are added to a solution of 724 mg (1.22 mmol) of the compound from Example 2-18c in 20 ml of THF. The mixture is stirred at room temperature for 30 min and then diluted with 100 ml of diethyl ether. The mixture is washed three times with in each case 25 ml of a semisaturated sodium chloride solution and once with 20 ml of saturated sodium chloride solution. The combined wash solutions are extracted with 20 ml of diethyl ether and the combined organic phases are dried with sodium sulphate. Yield: 747 mg of a colourless oil (which still contains tert-butyl(dimethyl)silyl fluoride). For characterization, a small amount was purified by column chromatography (silica gel (70–230 mesh), gradient: from cyclohexane to cyclohexane/ethyl acetate 1:1).

$R_f$ (cyclohexane/acetic acid 1:1)=0.4.

MS (ESI)=481 (M+H)$^+$.

$^1$H-NMR (200 MHz, DMSO-d$_6$) δ [ppm]: 0.83 (3H, t), 1.00 (9H, s), 1.20–1.52 (4H, m), 1.60–1.92 (4H, m), 2.35–2, 61 (2H, m), 2.95–3.17 (4H, m), 3.29–3.43 (2H, m), 4.59 (1H, t), 4.68 (2H, s), 6.98–7.29 (9H, m).

e) (1R,2R)-2-(4-{[{[Ethyl(2-hydroxyethyl)amino]carbonyl}(phenyl)amino]methyl}phenyl)cyclohexanecarboxylic acid:

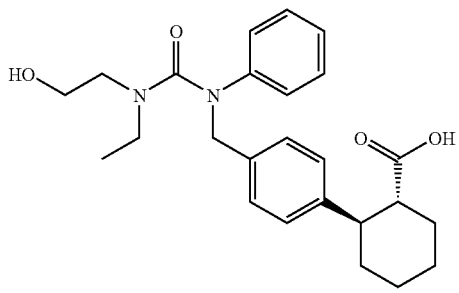

724 mg (1.51 mmol) of the compound from Example 2-18d are dissolved in 2 ml of dichloromethane, and 1 ml of trifluoroacetic acid is added. The solution is stored at room temperature for 5 hours and then treated with 15 ml of 1 N sodium hydroxide solution and 20 ml of water. The mixture is washed twice with in each case 20 ml of diethyl ether and adjusted to pH 3–4 using 1 N hydrochloric acid. The mixture is extractred three times with in each case 30 ml of dichloromethane and the extracts are dried with sodium sulphate and concentrated. The residue is taken up in 4 ml of diethyl ether and re-concentrated. The product, which is initially in oil, turns into a white solid foam. Yield: 276 mg (43% of theory, 99% purity according to HPLC).

$R_f$ (dichloromethane/methanol 10:1)=0.35.

MS (ESI)=425 (M+H)$^+$.

$^1$H-NMR (200 MHz, DMSO-d$_6$) δ [ppm]: 0.83 (3H, t), 1.20–1.55 (4H, m), 1.59–1.82 (3H, m), 1.88–2.02 (1H, m), 2.40–2.72 (2H, m), 2.99–3.20 (4H, m), 3.25–3.50 (2H, m), 4.68 (2H, s), 7.00–7.32 (9H, m), 11.74 (1H, br. s).

f) (1R,2R)-N-[(1S)-2-Amino-1-phenyl-2-oxoethyl]-2-(4-{[{[ethyl(2-hydroxyethyl)amino]carbonyl}(phenyl)amino]methyl}phenyl)cyclohexanecarboxamide:

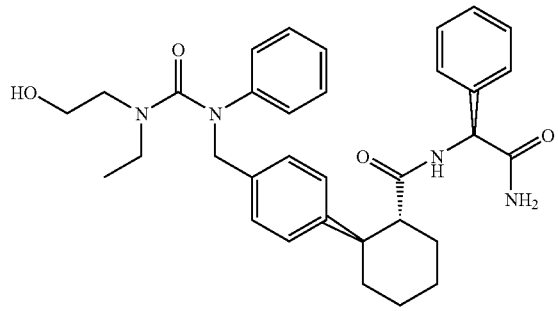

0.90 ml of abs. DMF is added to a mixture of 42.5 mg (0.100 mmol) of the compound from Example 2-18e, 13.5 mg (0.100 mmol) of HOBT, 23.0 mg (0.120 mmol) of EDC and 1 mg of DMAP. The mixture is stirred at room temperature for 5 min until a clear solution has formed. 22.0 μl (20.2 mg, 0.200 mmol) of N-methylmorpholine and 28 mg (0.150 mmol) of L-phenylglycinamide hydrochloride are then added. The mixture is stirred at room temperature for 3 days and then separated directly using RP-HPLC (C18 Gromsil, 50×20 mm, 25 m/min, gradient water/acetonitrile 90:10→water/acetonitrile 10:90 over 8 min). The acetonitrile is removed under reduced pressure and the product precipitates in the form of white flakes. The product is frozen and lyophilized overnight. This gives 37.6 mg (62% of theory) of the product as a white solid.

$R_f$ (dichloromethane/methanol 10:1)=0.44.

MS (ESI)=557 (M+H)$^+$.

$^1$H-NMR (200 MHz, DMSO-d$_6$) δ [ppm]: 0.84 (3H, t), 1.19–1.58 (4H, m), 1.61–1.88 (4H, m), 2.56–2.90 (2H, m), 3.00–3.23 (4H, m), 3.25–3.50 (2H, m), 4.65 (1H, t), 4.72 (2H, s), 5.17 (1H, d), 6.79–6.87 (2H, m), 6.95–7.30 (13H, m), 7.65 (1H, br s), 8.02 (1H, d).

The compounds listed in Table 2 below are prepared in an analogous manner; in addition to the data given in the table, further spectroscopic data of the individual compounds are listed below:

(S)-N-{{(1R,2R)-2-(4-{[{[Bis(2-hydroxyethyl)amino]carbonyl}(phenyl)amino]methyl}phenyl)cyclohex-1-yl}carbonyl}-phenylglycinamide (Example 2-3)

MS (ESI)=573 (M+H)$^+$.

$^1$H-NMR (200 MHz, DMSO-d$_6$) δ [ppm]: 1.21–1.60 (4H, m), 1.61–1.96 (4H, m), 2.60–2.93 (2H, m), 3.19 (4H, t), 3.39 (4H, t), 4.76 (2H, s), 5.15–5.25 (1H, m), 6.82–6.93 (2H, m), 6.90–7.35 (13H, m), 7.66 (1H, br. s), 8.04 (1H, d).

(S)-N-{{(1R,2R)-2-(4-{[{[2-Hydroxylethylamino]carbonyl}(phenyl)amino]methyl}phenyl)cyclohex-1-yl}carbonyl}-phenylglycinamide (Example 2-17)

MS (ESI)=551 (M+H)$^+$.

$^1$H-NMR (300 MHz, DMSO-d$_6$) δ [ppm]: 1.20–1.55 (4H, m), 1.62–1.89 (4H, m), 2.60–2.70 (1H, m), 2.77–2.86 (1H, m), 3.12 (2H, q) 3.32–3.40 (2H, m), 4.59 (1H, t), 4.80 (1H, s), 5.17 (1H, d), 5.66 (1H, t), 6.76–6.83 (2H, m), 6.97–7.23 (1H, m), 7.33 (2H, t), 7.65 (1H, br. s), 8.02 (1H, d).

TABLE 2

| Example | Structure | | Retention time (method) |
|---------|-----------|---|-------------------------|
| 2-2 | 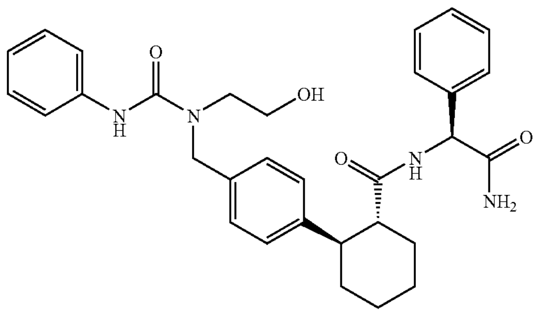 | chiral | 4.18 (A) |
| 2-3 | 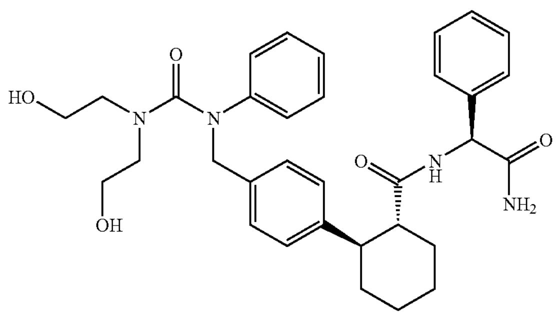 | chiral | 3.97 (A) |
| 2-4 | 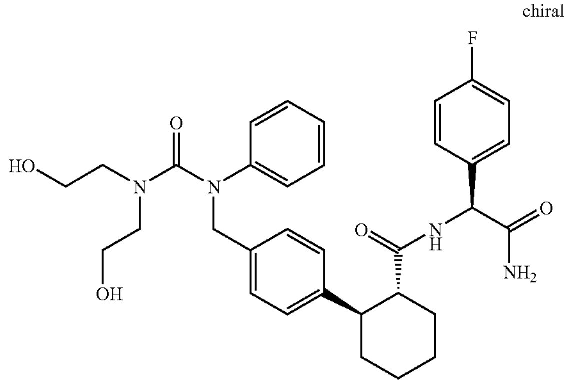 | chiral | 4.01 (A) |
| 2-5 | 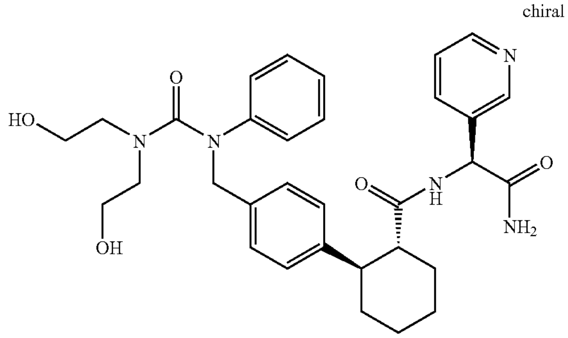 | chiral | 3.89 (A) |

TABLE 2-continued

| Example | Structure | | Retention time (method) |
|---|---|---|---|
| 2-6 | 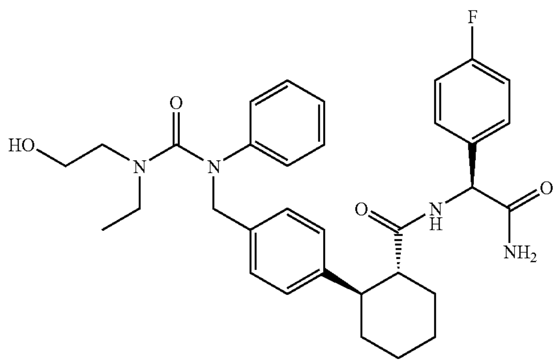 | chiral | 4.36 (A) |
| 2-7 | 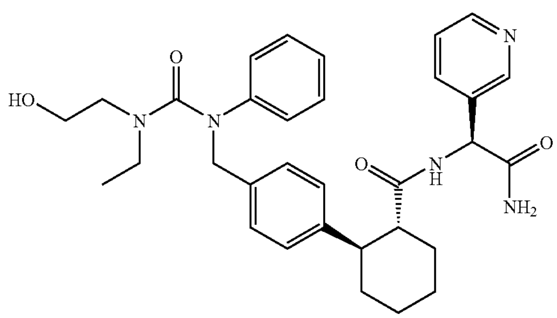 | chiral | 4.17 (A) |
| 2-8 | 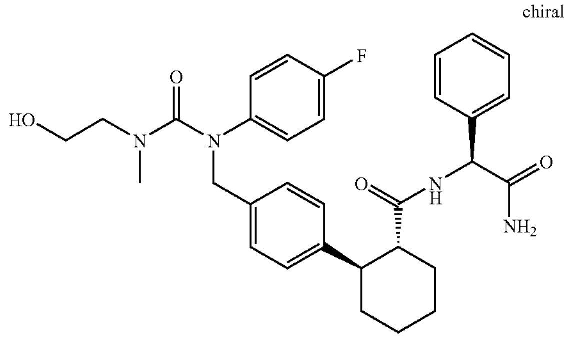 | chiral | 4.24 (A) |
| 2-9 | 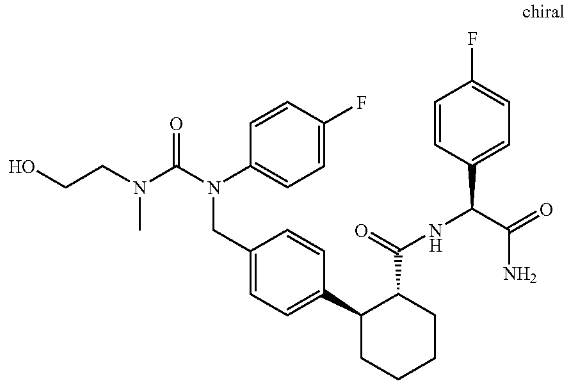 | chiral | 4.29 (A) |

TABLE 2-continued

| Example | Structure | | Retention time (method) |
|---|---|---|---|
| 2-10 | 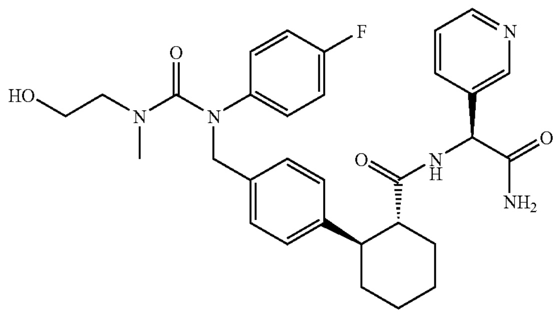 | chiral | 4.12 (B) |
| 2-11 | 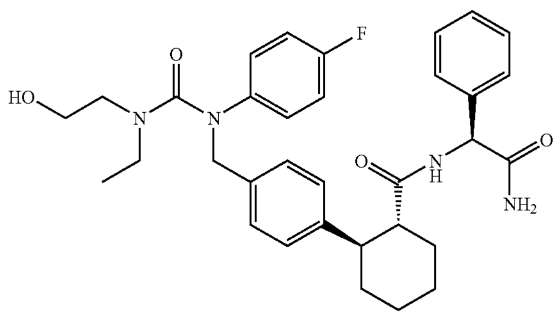 | chiral | 4.36 (A) |
| 2-12 | 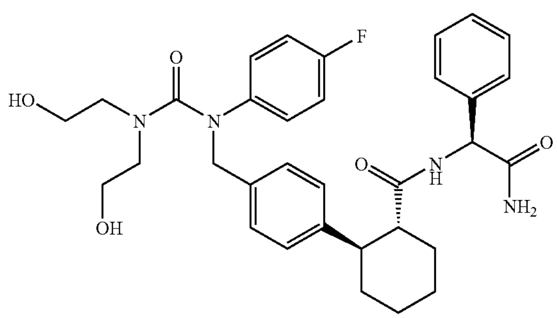 | chiral | 3.98 (A) |
| 2-13 | 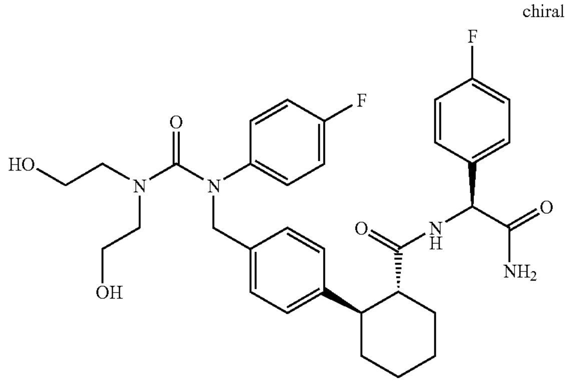 | chiral | 4.03 (A) |

TABLE 2-continued

| Example | Structure | Retention time (method) |
|---------|-----------|-------------------------|
| 2-14 | chiral | 3.90 (A) |
| 2-15 | chiral | 4.00 (A) |
| 2-16 | chiral | 3.90 (A) |
| 2-17 | 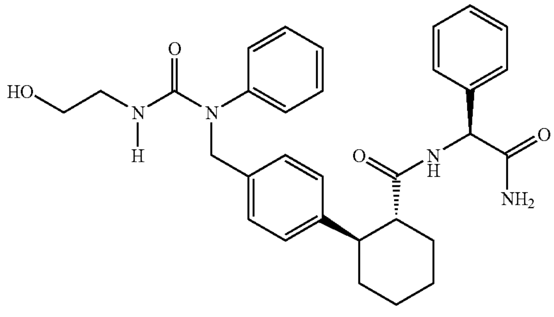 | 3.92 (A) |

Example 3-1

4-[(1R,2R)-2-({[(1S)-2-Amino-1-(4-fluorophenyl)-2-oxoethyl]amino}carbonyl)cyclohexyl]benzyl 4-hydroxy-1-piperidinecarbamate

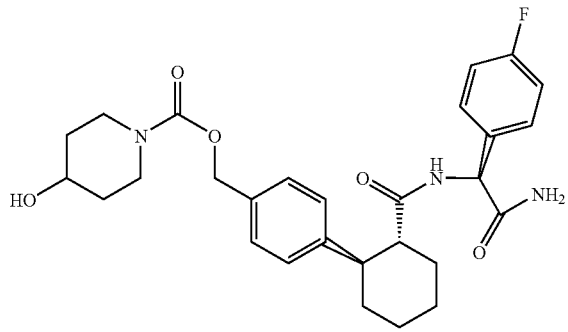

a) tert-Butyl(1R,2R)-2-{4-[(acetyloxy)methyl]phenyl}cyclohexanecarboxylate:

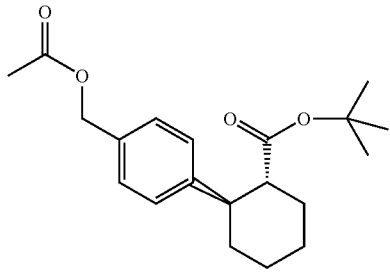

A suspension of tert-butyl(1R,2R)-2-(4-bromomethyl-phenyl)-cyclohexane-1-carboxylate from Example I (3 g, 8.49 mmol), potassium acetate (1.83 g, 18.68 mmol) and 18-crown-6 (134.7 mg, 0.51 mmol) in acetonitrile (15 ml) is stirred at 50° C. for 24 hours and at 60° C. for a further 16 hours. The reaction mixture is then concentrated under reduced pressure and extracted with water/methylene chloride. The organic phase is washed with saturated sodium chloride solution and dried over sodium sulphate. Concentration of the crude product under reduced pressure and silica gel chromatography (mobile phase: cyclohexane/ethyl acetate=30:1 to 8:1) gives 2.7 g (95.6%) of product as a colourless solid.

MS (ESI+): 350.4 (M+NH$_4$)$^+$ $^1$H-NMR (DMSO-d$_6$): 1.05 (9H, s); 1.30–1.55 (4H, m); 1.65–1.95 (4H, m); 2.02 (3H, s); 2.40–2.68 (2H, m); 5.02 (2H, s); 7.15–7.28 (4H, m).

b) (1R,2R)-2-{4-[(Acetyloxy)methyl]phenyl}cyclohexanecarboxylic acid:

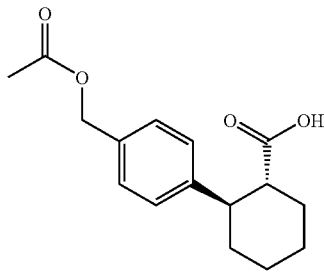

A solution of the compound from Example 3-1a (2.7 g, 8.12 mmol) in dichloromethane (15 ml) and trifluoroacetic acid (7.5 ml) is stirred at room temperature for 2 hours. The mixture is concentrated under reduced pressure and extracted with methylene chloride/water and then twice with saturated sodium chloride solution, giving, after concentration of the organic phase under reduced pressure, 2.2 g (94%) of product as a solidified oil.

MS (ESI+): 294.3 (M+NH$_4$)$^+$.

$^1$H-NMR (DMSO-d$_6$): 1.30–1.55 (4H, m); 1.65–2.02 (4H, m); 2.03 (3H, s); 2.40–2.75 (2H, m); 5.00 (2H, s); 7.15–7.28 (4H, m); 11.71 (1H, s).

c) 4-[(1R,2R)-2-({[(1S)-2-Amino-1-(4-fluorophenyl)-2-oxoethyl]amino}carbonyl)cyclohexyl]benzyl acetate:

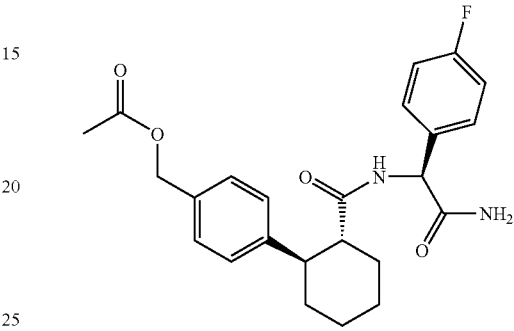

1-Hydroxylbenzotriazole (1.18 g, 8.76 mmol) and EDC (1.60 g, 8.36 mmol) are added to a solution of the compound from Example 3-1b (2.2 g, 7.96 mmol) in DMF (80 ml), and the mixture is stirred at room temperature for 10 min. N-Methylmorpholine (3.50 ml, 31.85 mmol), (+)-(S)-4-fluorophenylglycinamide (1.63 g, 7.96 mmol) and a spatula tip of DMAP are then added, and the mixture is stirred at room temperature overnight. Following addition of water (350 ml), the mixture is stirred at room temperature for 1 hour and then cooled with ice. The title compound is then filtered off, washed with water and diethyl ether and dried. Drying under reduced pressure (200 mbar, 50° C., 16 h) gives 2.70 g (74.8%) of the product as a colourless solid.

MS (ESI+): 427.0 (M+H)$^+$.

$^1$H-NMR (DMSO-d$_6$): 1.25–1.55 (4H, m); 1.65–1.90 (4H, m); 2.06 (3H, s); 2.64–2.71 (1H, m); 2.80–2.90 (1H, m); 5.02 (2H, s); 5.20 (1H, d); 6.75–6.94 (4H, m); 7.15–7.22 (5H, m); 7.67 (1H, s); 8.05 (1H, d).

d) (1R,2R)-N-[(1S)-2-Amino-1-(4-fluorophenyl)-2-oxoethyl]-2-[4-(hydroxymethyl)phenyl]cyclohexanecarboxamide:

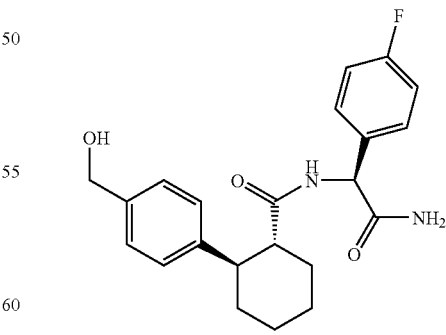

A suspension of the compound from Example 3-1c (2.70 g, 6.61 mmol) in ammonia solution (2M in methanol, 50 ml) is stirred at room temperature overnight. The mixture is concentrated under reduced pressure and the product is then stirred with diethyl ether (50 ml) for 1 hour and then cooled with ice and filtered off. Drying under reduced pressure (200 mbar, 50° C., 16 h) gives the product as a colourless solid (2.50 g, 98.4%).

MS (ESI+): 385.5 (M+H)+.

$^1$H-NMR (DMSO-$d_6$): 1.25–1.55 (4H, m); 1.65–1.88 (4H, m); 2.64–2.69 (1H, m); 2.77–2.85 (1H, m); 4.45 (2H, s); 5.17 (1H, d); 6.70–6.76 (2H, m); 6.87–6.94 (2H, m); 7.10–7.17 (5H, m); 7.65 (1H, s); 7.98 (1H, d).

e) 4-[(1R,2R)-2-({[(1S)-2-Amino-1-(4-fluorophenyl)-2-oxoethyl]amino}carbonyl)cyclohexyl]benzyl 4-hydroxy-1-piperidinecarbamate:

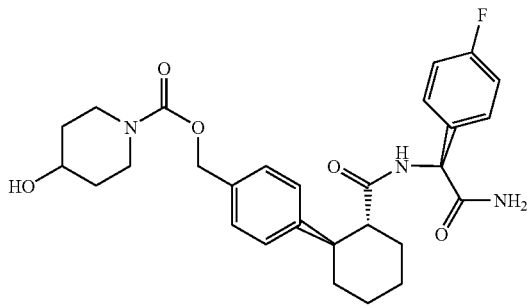

Triethylamine (0.16 ml, 1.17 mmol) and disuccinimidyl carbonate (149.9 mg, 0.59 mmol) are added to a solution of the compound from Example 3-1d (150.0 mg, 0.39 mmol) in DMF (5 ml), and the mixture is stirred at room temperature for 5 hours. 4-Hydroxylpiperidine (157.8 mg, 1.56 mmol) is then added, and the mixture is stirred at room temperature for 12 hours. After filtration, the solution is separated directly by preparative HPLC (column: Kroniasil 100 C 18.5 μm, 250×40 mm; mobile phase: methanol/water; flow rate: 25 ml/min; UV detection at 210 nm). Following concentration under reduced pressure, 93.7 mg (45.6%) of the product are obtained as a colourless solid.

MS (ESI+): 534.2 (M+Na)+.

$^1$H-NMR (DMSO-$d_6$): 1.15–1.95 (12H, m); 2.55–2.95 (2H, m); 2.95–3.16 (2H, m); 3.55–3.80 (3H, m); 4.72 (1H, d); 5.02 (2H, s); 5.19 (1H, d); 6.70–6.95 (4H, m); 7.10–7.25 (5H, m); 7.70 (1H, br.s); 8.09 (1H, d).

Example 3-23

4-[(1R,2R)-2-({[(1S)-2-Amino-1-(4-fluorophenyl)-2-oxoethyl]amino}carbonyl)cyclohexyl]benzyl 4-(2-hydroxyethyl)-1-piperazinecarbamate

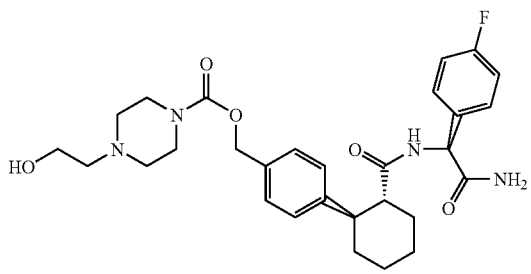

Triethylamine (0.06 ml, 0.43 mmol) and disuccinimidyl carbonate (73.3 mg, 0.29 mmol) are added to a solution of the compound from Example 3-1d (55 mg, 0.14 mmol) in DMF (2 ml), and the mixture is stirred at room temperature overnight. The reaction mixture is admixed with methylene chloride (about 10 ml) and washed 3× with a little saturated ammonium chloride solution. The organic phase is then dried over sodium sulphate and, after filtration, concentrated under reduced pressure. The resulting crude mixture is added to a mixture of N-(2-hydroxyethyl)piperazine (74.3 mg, 0.57 mmol) and a spatiila tip of DMAP and stirred at room temperature for 12 hours. Following filtration, the solution is separated directly by preparative HPLC (column: Kromasil 100 C 18.5 μm, 250×40 mm; mobile phase: acetonitrile/water; flow rate: 25 m/min; UV detection at 210 nm). Following concentration under reduced pressure, 25 mg (29.8%) of the product are obtained as a colourless solid.

MS (ESI+): 541.3 (M+H)+.

$^1$H-NMR (DMSO-$d_6$): 1.20–1.60 (4H, m); 1.65–1.90 (4H, m); 2.25–2.60 (8H, m); 2.60–2.90 (2H, m); 3.25–3.54 (4H, m); 4.38 (1H, t); 5.03 (2H, s); 5.19 (1H, d); 6.72–6.95 (4H, m); 7.08–7.24 (5H, m); 7.62 (1H, s); 8.02 (1H, d).

Example 3-36

4-[(1R,2R)-2-({[(1S)-2-Amino-1-phenyl-2-oxoethyl]amino}carbonyl)-cyclohexyl]benzyl 4-(2-hydroxyethyl)-1-piperazinecarbamate

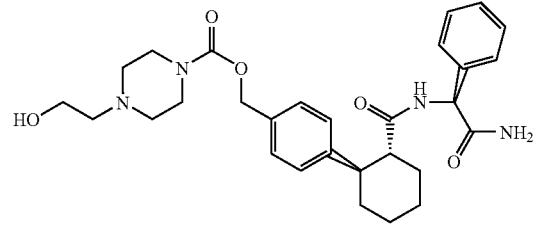

is prepared analogously to Example 3-23 using, instead of (+)-(S)-4-fluorophenylglycinamide, (+)-(S)-phenylglycinamide. Purification is carried out by preparation HPLC (column: Waters Symmetry C 18, 7 μm, 300×19 mm; mobile phase: acetonitrile/water/2% acetic acid, flow rate: 25 ml/min; UV detection at 230 nm). Following concentration under reduced pressure, the product is obtained in the form of the acetate, from which, by addition of methylene chloride and subsequent extraction with a 1:1 mixture of saturated sodium chloride solution and 2 molar sodium carbonate solution, the compound is obtained as a colourless solid.

MS (ESI+): 523 [M+H]+.

$^1$H-NMR (DMSO-$d_6$): 1.20–1.60 (4H, m); 1.65–1.92 (4H, m); 2.27–2.60 (8H, m); 2.60–2.95 (2H, m); 3.27–3.55 (4H, m); 4.41 (1H, t); 5.03 (2H, s); 5.19 (1H, d); 6.70–6.85 (2H, m); 7.0–7.26 (8H, m); 7.66 (1H, s); 8.02 (1H, d).

The compounds listed in Table 3 below are prepared in an analogous manner:

TABLE 3
| Example | Structure | Retention time (method) |
|---|---|---|
| 3-2 | 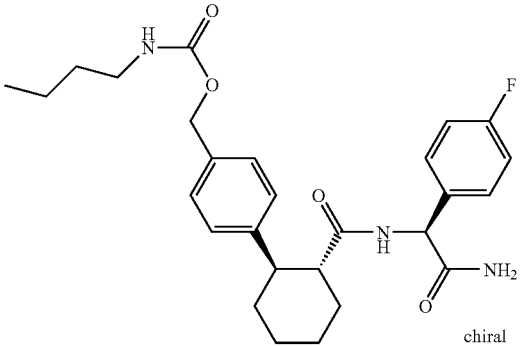 | 4.02 (C) |
| 3-3 | 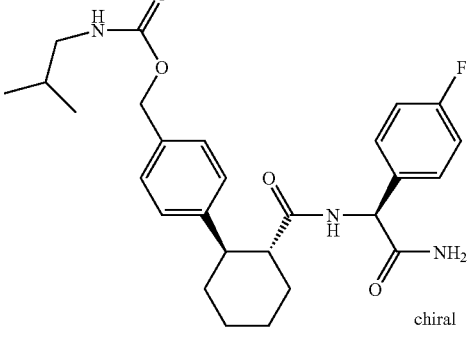 | 4.00 (C) |
| 3-4 | 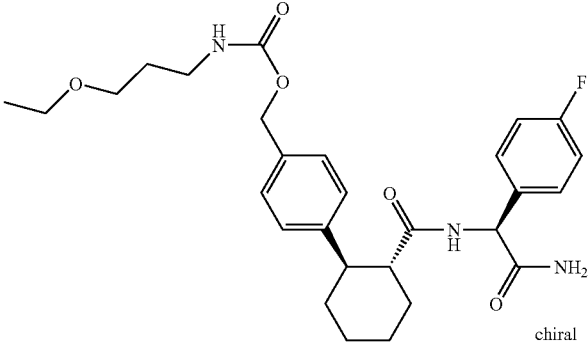 | 3.73 (C) |
| 3-5 | 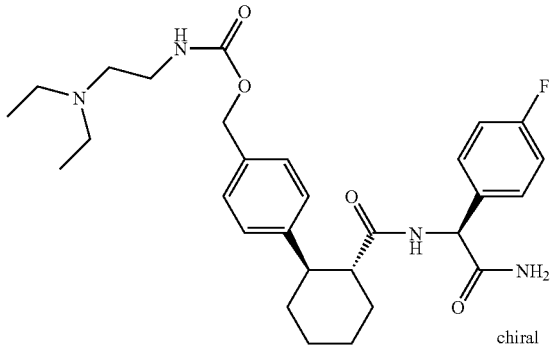 | 2.54 (C) |

TABLE 3-continued
| Example | Structure | Retention time (method) |
|---|---|---|
| 3-6 | 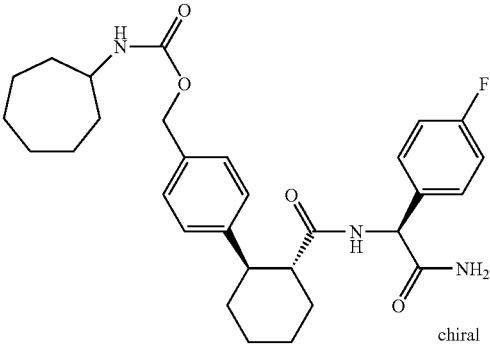 | 4.39 (C) |
| 3-7 | 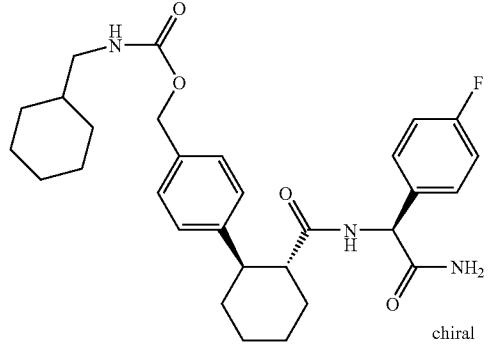 | 4.42 (C) |
| 3-8 | 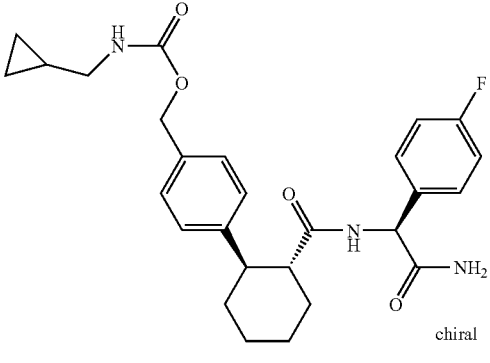 | 3.86 (C) |
| 3-9 | 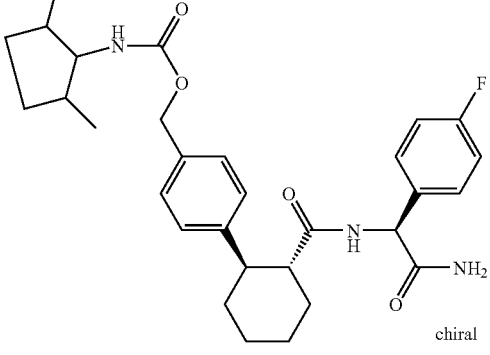 | 4.38 (C) |

TABLE 3-continued
| Example | Structure | Retention time (method) |
|---|---|---|
| 3-10 | 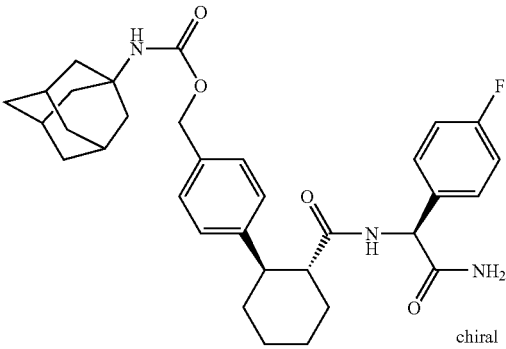 | 4.47 (C) |
| 3-11 | 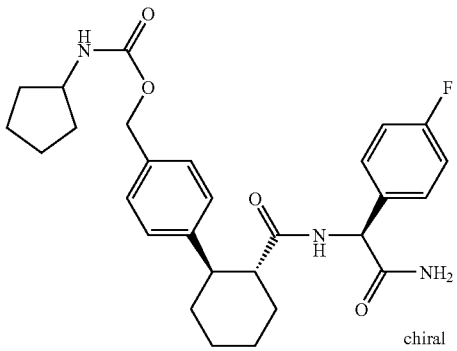 | 4.04 (C) |
| 3-12 | 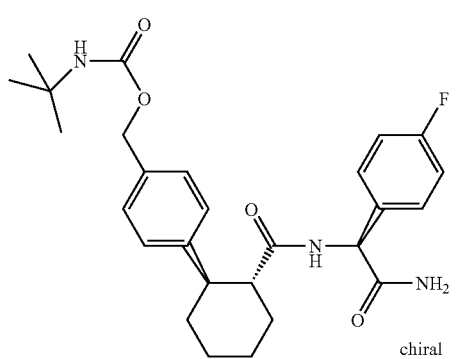 | 4.08 (C) |
| 3-13 | 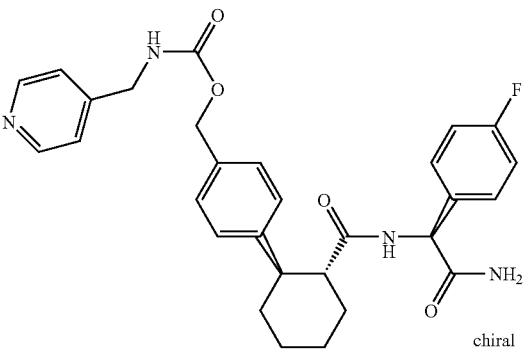 | 2.58 (C) |

TABLE 3-continued
| Example | Structure | Retention time (method) |
|---|---|---|
| 3-14 | 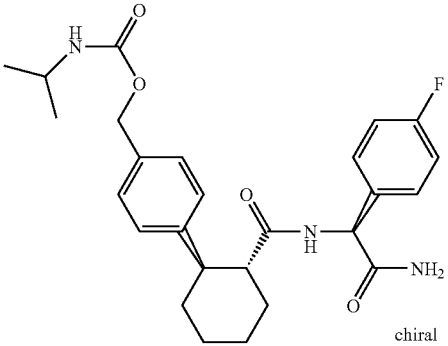 | 3.80 (C) |
| 3-15 | 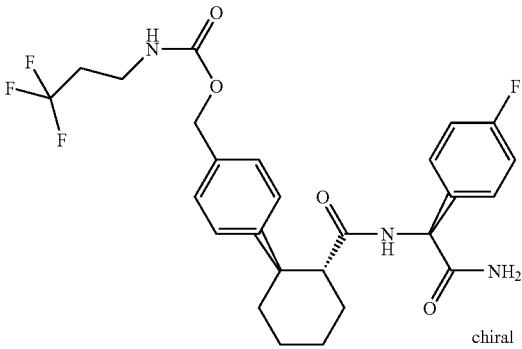 | 3.91 (C) |
| 3-16 | 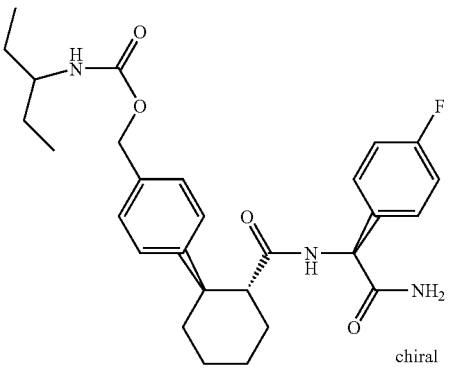 | 4.14 (C) |
| 3-17 | 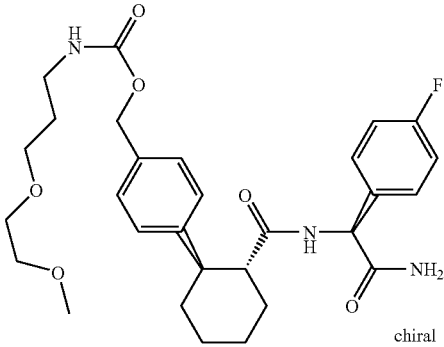 | 3.54 (C) |

TABLE 3-continued
| Example | Structure | Retention time (method) |
|---|---|---|
| 3-18 | 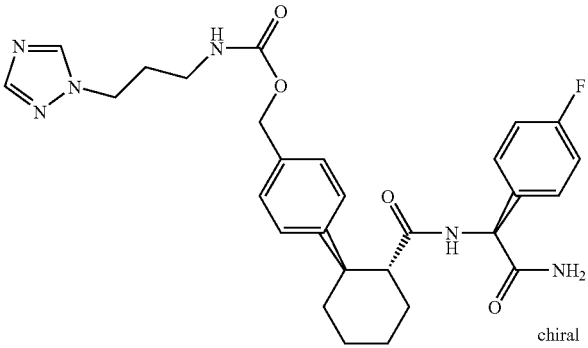 | 3.19 (C) |
| 3-19 | 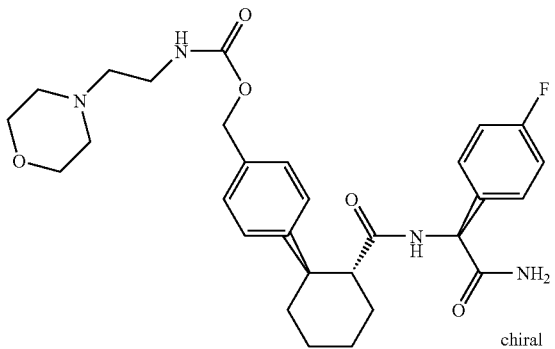 | 2.45 (C) |
| 3-20 | 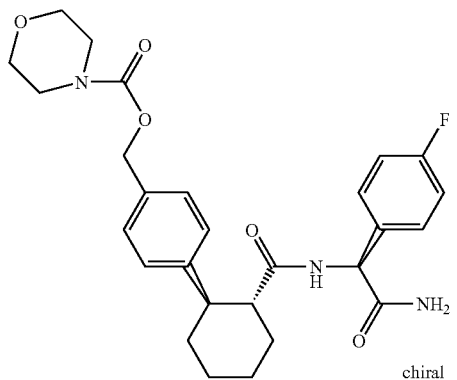 | 3.56 (C) |
| 3-21 | 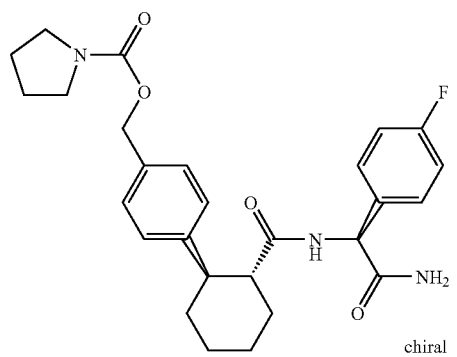 | 3.82 (C) |

TABLE 3-continued
| Example | Structure | Retention time (method) |
|---|---|---|
| 3-22 | 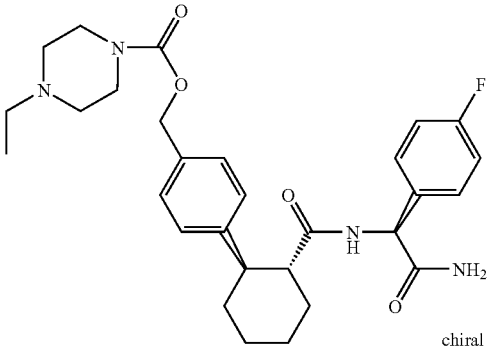 | 2.51 (C) |
| 3-23 | 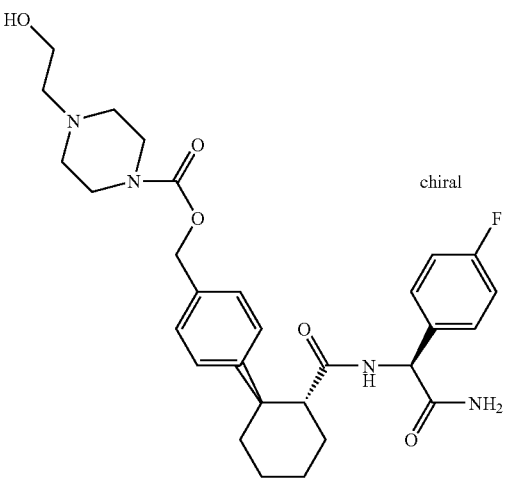 | 3.66 (A) |
| 3-24 | 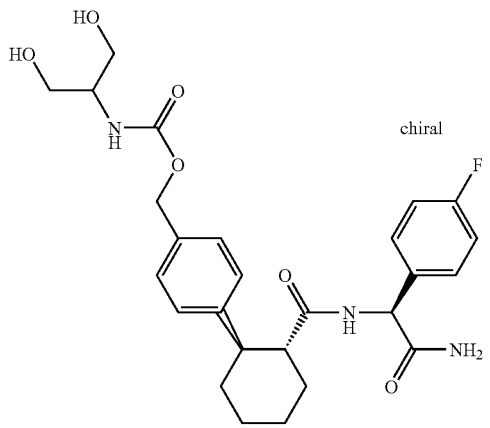 | 3.57 (A) |

TABLE 3-continued
| Example | Structure | Retention time (method) |
|---|---|---|
| 3-25 | 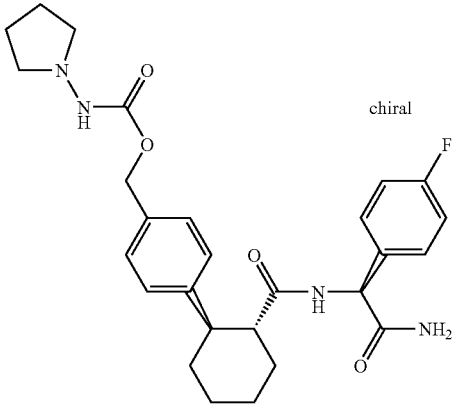 | 3.68 (A) |
| 3-26 | 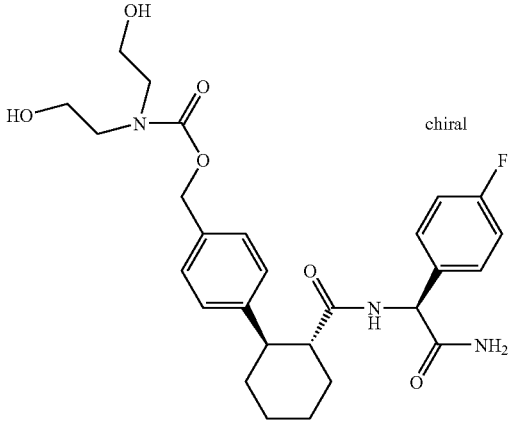 | 3.64 (A) |
| 3-27 | 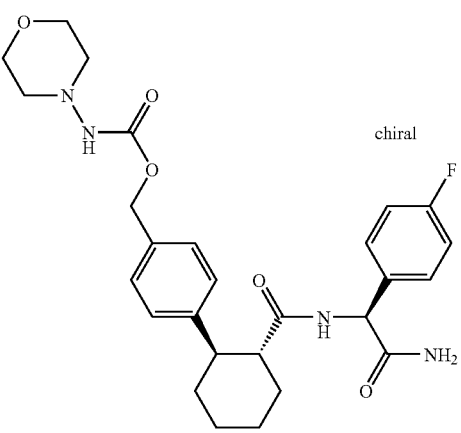 | 3.77 (A) |

TABLE 3-continued

| Example | Structure | Retention time (method) |
|---|---|---|
| 3-28 | 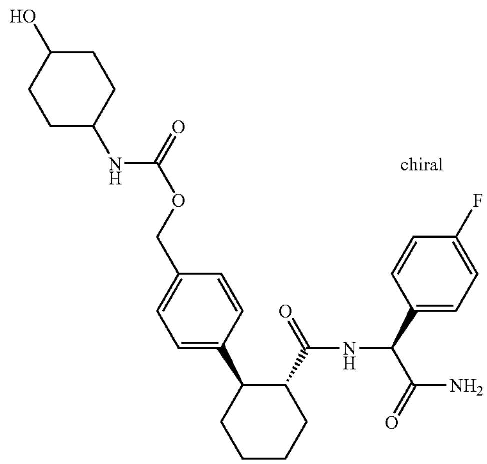 | 3.86 (A) |
| 3-29 | 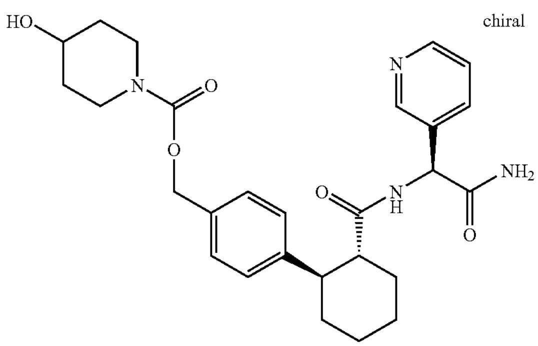 | 2.64 (C) |
| 3-30 | 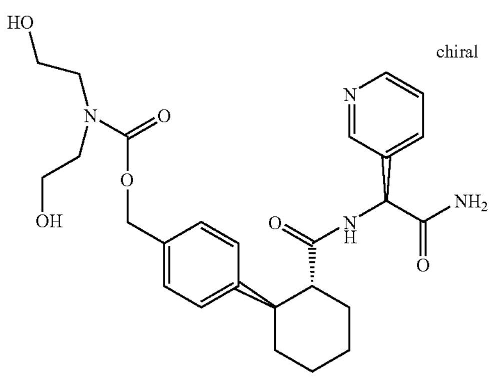 | 2.40 (C) |
| 3-31 | 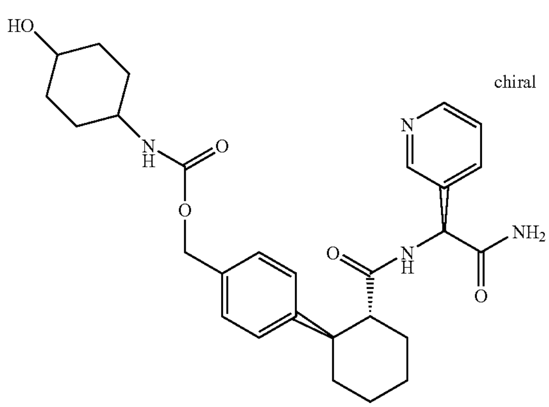 | 2.63 (C) |

TABLE 3-continued

| Example | Structure | Retention time (method) |
|---------|-----------|------------------------|
| 3-32 | 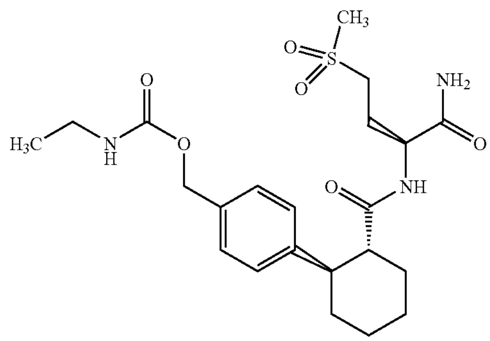 | 3.71 (E) |
| 3-33 | 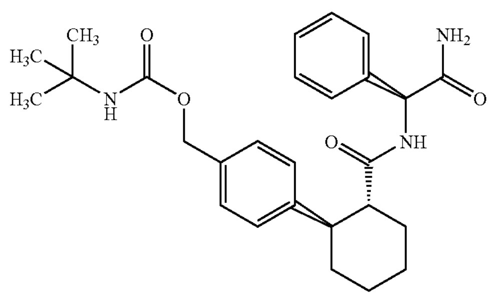 | 4.35 (E) |
| 3-34 | 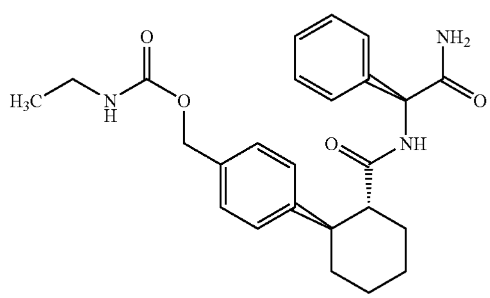 | 4.00 (E) |
| 3-35 | 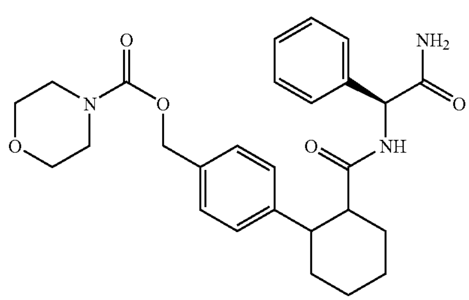 | Rf (CH2Cl2:MeOH = 20:1) 0.35 |

Example 4-1

Benzyl(4-[2-({[(1S)-2-amino-2-oxo-1-phenylethyl]amino}carbonyl)cyclohexyl]benzyl)-carbamate

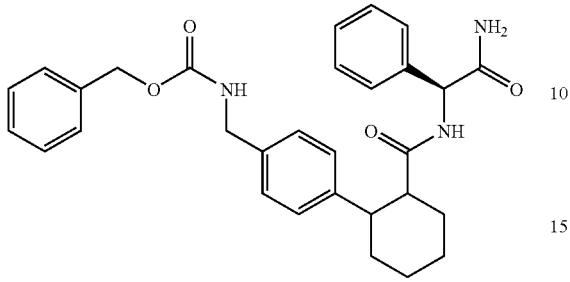

a) tert-Butyl 2-[4-({bis[(benzyloxy)carbonyl]amino}methyl)phenyl]cyclohexancarboxylate:

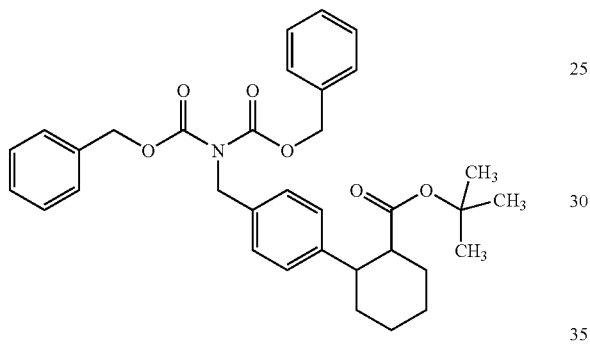

is obtained analogously to the general procedure A from racemic tert-butyl trans-2-(4-bromomethylphenyl)-cyclohexane-1-carboxylate according to Example I and bis[(benzyloxy)carbonyl]amine (U. Ragnarsson et al., Synthesis, 1988, 992) in the presence of NaH in DMF.

b) 2-[4-({(Benzyloxy)carbonylamino}methyl)phenyl]cyclohexanecarboxylic acid:

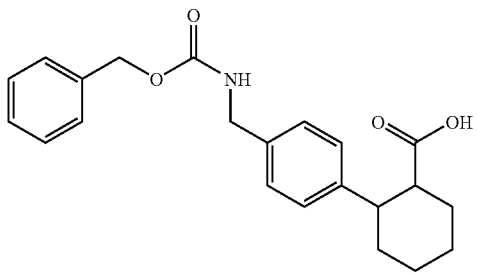

The ester from Example 4-1a (0.36 mmol) is dissolved in dichloromethane (5 ml), treated with trifluoroacetic acid (5 ml) and stirred at room temperature for 2 hours. For work-up, the mixture is, at 0° C., neutralized with 2M aqueous sodium hydroxide solution and extracted with dichloromethane, and the organic phase is dried over magnesium sulphate and concentrated. The residue is chromatographed (silica gel; cyclohexane:ethyl acetate:acetic acid 3:1:0.1), giving 91.2 mg of acid.

$R_f$ (cyclohexane:ethyl acetate:acetic acid 3:1:0.2)=0.21.

c) Benzyl 4-[2-({[(1S)-2-amino-2-oxo-1-phenylethyl]amino}carbonyl)cyclohexyl]benzyl)carbamate:

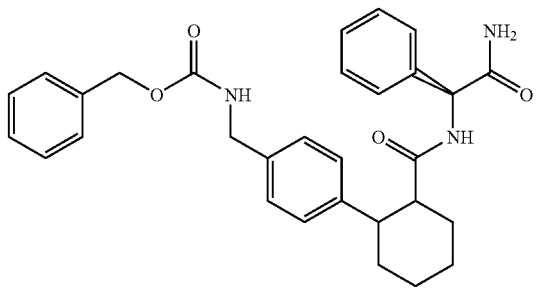

is prepared analogously to the general procedure C from the acid according to Example 4-1b and (S)-phenylglycinamide hydrochloride. A mixture of the trans diastereomers is obtained.

$R_f$ (methylene chloride/methanol 20:1)=0.32.

Example 5-1

N-{4-[2-({[(1S)-2-Amino-2-oxo-1-phenylethyl]amino}carbonyl)cyclohexyl]benzyl}-4-fluorobenzamide:

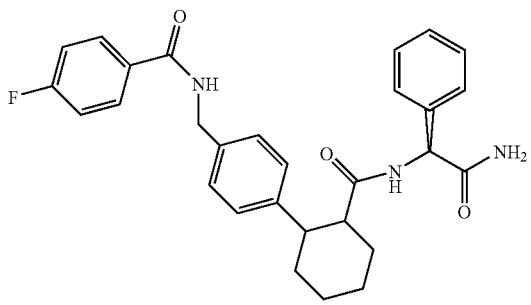

a) tert-Butyl 2-{4-[(1,3-dioxo-1,3-dihydro-2H-isoindol-2-yl)methyl]phenyl}cyclohexanecarboxylate:

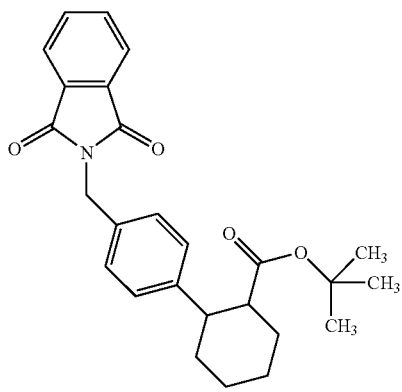

Racemic tert-butyl trans-2-(4-bromomethyl-phenyl)-cyclohexane-1-carboxylate according to Example 1 (6.3 mmol) is initially charged in DMF (30 ml) and treated with potassium phthalimide (6 mmol). After 5 min at room temperature, the mixture is heated at 50° C. for 20 hours. Following addition of water, extraction with ether and flash chromatography on silica gel (dichloromethane:cyclohexane 1:1→dichloromethane), 1.66 g of a slightly yellowish solid are obtained.

$R_f$ (methylene chloride)=0.2.

b)–c) The Hydrolysis of the Ester and the Subsequent Amide Formation are Carried Out Analogously to the General Procedures B and C d) (2S)-N-[2-(4-Aminomethyl-phenyl)-cyclohexyl-1-carbonyl]-phenylglycinamide:

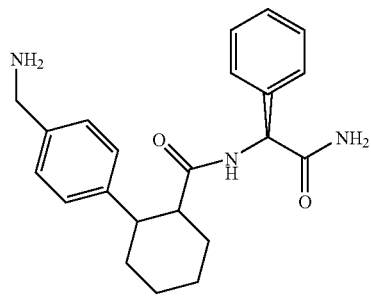

Hydrazine hydrate (7.6 mmol) is added to a suspension of the phthalimide from Example 5-1c (0.5 mmol) in ethanol (10 ml), and the mixture is stirred at room temperature for 3 days. 1 M HCl is added until a pH=2 is reached, and the mixture is then partitioned between dichloromethane and 10% strength sodium bicarbonate solution and the organic phase is dried over sodium sulphate and concentrated. Chromatography (silica gel, dichloromethane:methanol:ammonia 100:10:1) gives 105 mg (51% yield) of a mixture of diastereomers as a yellowish solid.

$R_f$ (dichloromethane:methanol:ammonia 100:10:1)=0.13 and 0.10.

MS (DCI, $NH_3$)=510 ($M+H^+$).

$^1$H-NMR (DMSO-$d_6$): A: 1.25–1.4 (4H, m); 1.7–1.85 (4H, m); 2.55–2.8 (2H, m); 3.3 (2H, br s); 3.7 (2H, s); 5.1 (1H, d); 6.85 (1H, s); 6.95 (1H, s); 7.1–7.3 (9H, m); 8.15 (1H, d); B: 1.35–1.55 (4H, m); 1.65–1.9 (4H, m); 2.2 (2H, br s); 2.6–2.7 (1H, m); 2.8 (1H, td); 3.7 (2H, s); 5.2 (1H, d); 6.85 (2H, d); 7.05–7.2 (8H, m); 7.6 (1H, s); 7.95 (1H, d).

e) N-{4-[2-({[(1S)-2-Amino-2-oxo-1-phenylethyl]amino}carbonyl)cyclohexyl]benzyl}-4-fluorobenzamide:

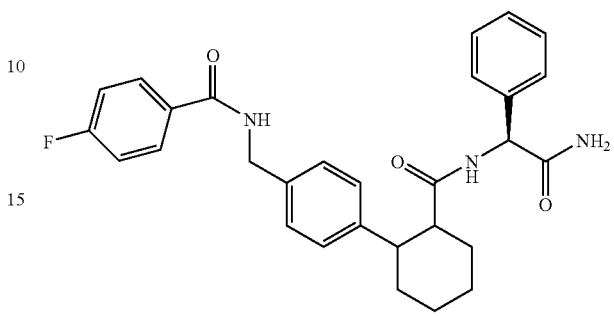

The amine from Example 5-1d (0.274 mmol) is, together with triethylamine (0.82 mmol), dissolved in dichloromethane (3 ml) and treated with 4-fluorobenzoic anhydride (0.3 mmol). The mixture is stirred at room temperature until its consistency is gel-like (about 5 min). Methanol is then added until the mixture is completely dissolved, the solution is then adsorbed on silica gel and the product is eluted using dichloromethane/methanol 10:1. This gives 101 mg of the desired product.

$R_f$ (dichloromethane:methanol 10:1)=0.24.

The compounds listed in Table 4 below are prepared in an analogous manner:

TABLE 4

| Example | Structure | $R_f$ value (CH$_2$Cl$_2$:MeOH:NH$_3$ aq) |
|---------|-----------|------------------------------------------|
| 5-2 | 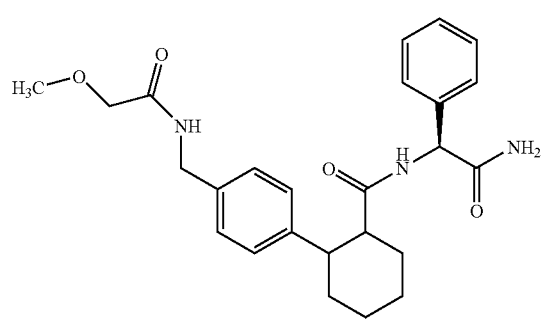 | 0.22 (10:1:0) |
| 5-3 | 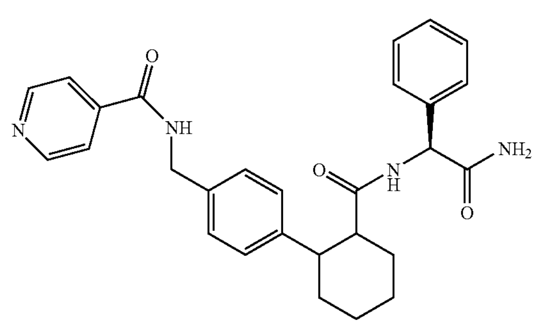 | 0.38 (10:1:0) |

| Example | Structure | R_f value (CH₂Cl₂:MeOH:NH₃ aq) |
|---------|-----------|-------------------------------|
| 5-4 | 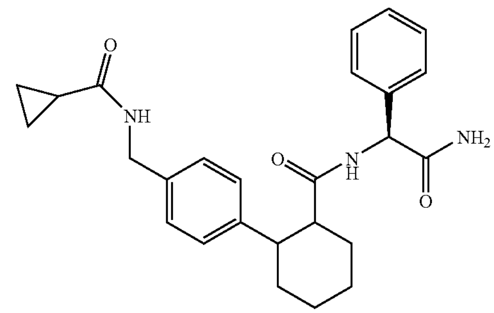 | 0.42/0.4 (10:1:0) |

Example 6-1

(1R,2R)-N-[(1R)-2-Amino-1-(4-fluorophenyl)-2-oxoethyl]-2-{4-[3-(cyclopropylamino)-3-oxopropyl]phenyl}cyclohexanecarboxamide a) Dimethyl 2-{4-[(1R,2R)-2-(tert-butoxycarbonyl)cyclohexyl]benzyl}malonate:

Dimethyl malonate (1.86 ml, 16.28 mmol) is added to a suspension of NaH (60% in mineral oil, 0.62 g, 15.57 mmol) in THF (50 ml), and the mixture is stirred at room temperature for 15 min. The resulting solution is added to a solution of tert-butyl (1R,2R)-2-(4-bromomethyl-phenyl)-cyclohexane-1-carboxylate from Example I (5 g, 14.15 mmol) in THF (50 ml), and the mixture is stirred overnight at room temperature. The mixture is then admixed with water (200 ml) and ethyl acetate (500 ml) and shaken, and the organic phase is washed with saturated ammonium chloride solution and sodium chloride solution. The organic phase is dried over sodium sulphate, filtered, concentrated under reduced pressure and chromatographed on silica gel (mobile phase: cyclohexane/ethyl acetate=6:1), giving 5 g (87%) of product as a colourless liquid.

MS (DCI): 422.4 (M+NH₄)⁺.

¹H-NMR (DMSO-d₆): 1.15 (9H, s); 1.30–1.50 (4H, m); 1.65–1.95 (4H, m); 2.35–2.65 (2H, m); 3.03 (2H, d); 3.60 (6H, s); 3.81 (1H, t); 6.95–7.15 (4H, m).

b) (1R,2R)-2-{4-[3-Methoxy-2-(methoxycarbonyl)oxopropyl]phenyl}cyclohexanecarboxylic acid:

Under ice-cooling, trifluoroacetic acid (57.2 ml) is added to a solution of the compound from Example 6-1a (5 g, 12.36 mmol) in dichloromethane (130.7 ml), and the mixture is then stirred at room temperature for 5 hours. Concentration of the mixture under reduced pressure and silica gel chromatography (mobile phase: dichloromethane/methanol=60:1 to 20:1) gives 3.2 g (74%) of product as a colourless foam.

MS (DCI): 366.1 (M+NH₄)⁺.

¹H-NMR (DMSO-d₆): 1.30–1.50 (4H, m); 1.65–1.70 (3H, m); 1.90–2.00 (1H, m); 2.45–2.55 (1H, m); 2.60–2.70 (1H, m); 3.03 (2H, d); 3.60 (6H, 2 s); 3.83 (1H, t); 7.10 (4H, q).

c) Dimethyl 2-{4-[(1R,2R)-2-({[(1S)-2-amino-1-(4-fluorophenyl)-2-oxoethyl]amino}carbonyl)cyclohexyl]benzyl}malonate:

1-Hydroxylbenzotriazole (0.38 g, 2.80 mmol) and EDC (0.56 g, 2.92 mmol) are added to a solution of the compound from Example 6-1b (0.89 g, 2.54 mmol) in DMF (20 ml), and the mixture is stirred at room temperature for 10 min. N-Methylmorpholine (1.40 ml, 12.72 mmol), (+)-(S)-4-fluorophenylglycinamide (0.52 g, 2.54 mmol) and a spatula tip of DMAP are then added, and the mixture is stirred at room temperature overnight. Following addition of water (50 ml), the mixture is stirred at room temperature for 1 hour. The title compound is then filtered off, washed with water and diethyl ether and dried. This gives 1.17 g (92%) of a colourless solid.

MS (ESI+): 499.3 (M+H+).

$^1$H-NMR (DMSO-$d_6$): 1.20–1.90 (8H, m); 2.55–2.90 (2H, m); 3.03 (2H, d); 3.60 (6H, 2 s); 3.81 (1H, t); 5.16 (1H, d); 6.80–7.20 (9H, m); 7.64 (1H, br.s); 8.08 (1H, d).

d) 3-{4-[(1R,2R)-2-({[2-Amino-1-(4-fluorophenyl)-2-oxoethyl]amino}carbonyl)cyclohexyl]phenyl}propanecarboxylic acid (mixture of epimers or R,R,R-diastereomer)

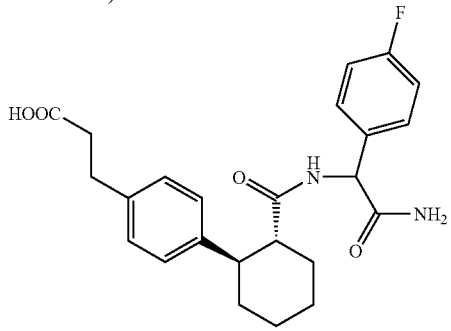

Lithium hydroxide (0.28 g, 11.73 mmol) is added to a suspension of the compound from Example 6-1c (1.17 g, 2.35 mmol) in methanol (10 ml) and water (40 ml), and the mixture is stirred at 50° C. for 1 hour. The methanol is then distilled off, and the mixture is acidified with 2 N hydrochloric acid to pH 2. The resulting residue is extracted with methylene chloride/methanol and concentrated under reduced pressure. The residue is then taken up in dioxane (100 ml) and at 120° C. refluxed overnight. Concentration under reduced pressure gives 508 mg (50.5%) of the product (mixtures of epimers) as a colourless oil. When a little methylene chloride/methanol is added to this oil, the pure (R,R,R)-diastereomer (102 mg, 13%) crystallizes from the solution as a colourless solid.

MS (mixture of epimers, ESI+): 427.3 (M+H)+.

$^1$H-NMR [R,R,R-diastereomer] (DMSO-$d_6$): 1.20–1.45 (4H, m); 1.60–1.90 (4H, m); 2.45–2.60 (obscured by the DMSO signal); 2.60–2.90 (4H, m); 5.12 (1H, d); 6.80–7.35 (10H, m); 8.18 (1H, d); 12.15 (1H, br.s).

e) (1R,2R)-N-[2-amino-1-(4-fluorophenyl)-2-oxoethyl]-2-{4-[3-(cyclopropylamino)-3-oxopropyl]phenyl}cyclohexanecarboxamide (R,R,R-diastereomer or R,R,S-diastereomer):

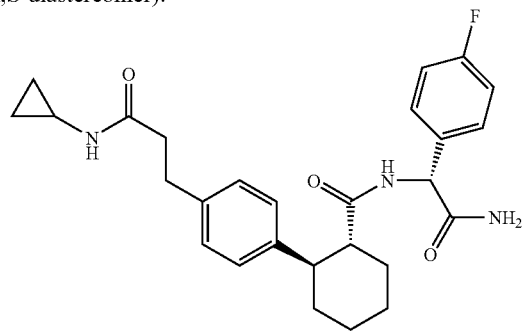

1-Hydroxybenzotriazole (8.7 mg, 0.064 mmol) and EDC (12.9 mg, 0.067 mmol) are added to a solution of the compound from Example 6-1d (R,R,R-diastereomer, 25.0 mg, 0.059 mmol) in DMF (1.5 ml), and the mixture is stirred at room temperature for 10 min. N-Methylmorpholine (0.016 ml, 0.147 mmol), cyclopropylamine (8.4 mg, 0.147 mmol) and a spatula tip of DMAP are then added and the mixture is stirred at room temperature overnight. Following concentration of the mixture under reduced pressure, the crude product is taken up in methylene chloride, washed with water and dried over sodium sulphate. The crude product is concentrated under reduced pressure and chromatographed on silica gel (mobile phase: dichloromethane/methanol=20:1 to 10:1), giving 25.0 mg (92%) of product as a colourless solid.

MS (ESI+): 466.3 (M+H+)+.

$^1$H-NMR (DMSO-$d_6$): 0.30–0.65 (4H, m); 1.20–1.40 (4H, m); 1.65–1.80 (4H, m); 2.25–2.35 (2H, m); 2.45–2.80 (5H, m); 5.16 (1H, d); 6.90–7.35 (10H, m); 7.85 (1H, d); 8.15 (1H, d).

The corresponding (R,R,S)-diastereomer can be prepared analogously by using the compound from Example 6-1d (mixture of epimers) as starting material. Here, the product is obtained as a mixture of epimers which can be separated into the pure epimers [(R,R,S)- and (R,R,R)-diastereomers] by preparative HPLC chromatography (column: Kromasil 100 C 18, 5 µm, 50×20 mm; mobile phase: acetonitrile/water; flow rate: 10 ml/min; UV detection at 254 nm).

Example 6-2

(1R,2R)-N-[2-Amino-1-(4-fluorophenyl)-2-oxoethyl]-2-(4-{3-[bis(2-methoxyethyl)amino]-3-oxopropyl}phenyl)cyclohexanecarboxamide

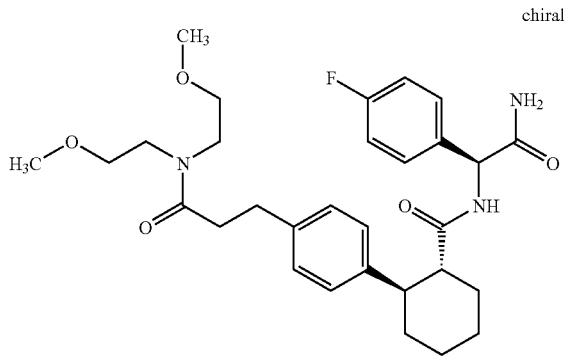

(1R,2R)-N-[2-Amino-1-(4-fluorophenyl)-2-oxoethyl]-2-(4-{3-[bis(2-methoxyethyl)-amino]-3-oxopropyl}phenyl)cyclohexanecarboxamide is prepared analogously to the reaction sequence described in Example 6-1.

Rt time (method C)=3.57.

The HPLC retention times given in the examples and tables above refer to the HPLC methods below A: Mobile phase A:=1% HClO$_4$ in water, B=acetonitrile, gradient: 0.5 min 98% A, 4.5 min 10% A, 6.5 min 10% A, 6.7 min 98% A, 7.5 min 98% A, Kromasil 100 C18, 60×2 mm, 0.75 m/min, 210 nm, 30° C.

B: Mobile phase A:=1% HClO$_4$ in water, B=acetonitrile, gradient: 0.5 min 98% A, 4.5 min 10% A, 9.0 min 10% A, 9.2 min 98% A, 10.0 min 98% A, Kromasil 100 C18, 60×2 mm, 0.75 ml/min, 210 nm, 30° C.

C: Mobile phase A:=0.1% formic acid in water, B=0.1% formic acid in acetonitrile, gradient: 0 min 90% A, 4 min 10% A, 6.1 min 90% A, symmetry C18, 50×2.1 mm, 0.5 m/min, 210 nm, 30° C.

D: Mobile phase A:=0.01 M phosphoric acid in water, B=acetonitrile, gradient: 1 min 90% A, 9 min 10% A, 13 min 10% A, 13.5 min 90% A, 15 min, 90% A, Kromasil 100 C18, 125×2 mm, 210 nm, 30° C.

E: Mobile phase A:=0.5% HClO₄ in water, B=acetonitrile, gradient: 0.5 min 98% A, 4.5 min 10% A, 6.5 min 10% A, 6.7 min 98% A, 7.5 min 98% A, Kromasil 100 C18, 60×2 mm, 0.75 ml/min, 210 nm, 30° C.

What is claimed is:

1. A compounds of the formula (I)

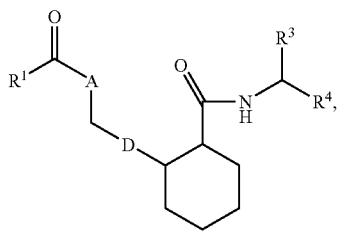

(I)

in which
D represents a radical

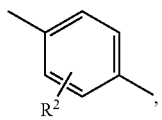, in which
$R^2$ represents hydrogen, halogen, hydroxyl, carboxyl, cyano, nitro, trifluoromethyl, trifluoromethoxy, $(C_1-C_6)$-alkyl, $(C_1-C_6)$-alkoxy or $(C_1-C_6)$-alkoxycarbonyl, A represents a group of the formula N—$R^5$,
in which
$R^5$ represents hydrogen, $(C_1-C_6)$-alkyl, $(C_3-C_7)$-cycloalkyl, where alkyl and cycloalkyl for their part may be substituted up to three times independently of one another by hydroxyl or mono- or di-$(C_1-C_6)$-alkylamino, or represents $(C_6-C_{10})$-aryl, where aryl for its part may be substituted up to three times independently of one another by halogen, hydroxyl, cyano, nitro, trifluoromethyl, trifluoromethoxy, $(C_1-C_6)$-alkyl, $(C_1-C_6)$-alkoxy, $(C_1-C_6)$-alkoxycarbonyl or mono- or di-$(C_1-C_6)$-alkylamino, $R^1$ represents hydrogen, $(C_1-C_6)$-alkyl, which for its part may be substituted by hydroxyl or $(C_1-C_4)$-alkoxy, represents $(C_3-C_7)$-cycloalkyl, or represents $(C_6-C_{10})$-aryl, where aryl for its part may be substituted independently of one another by halogen, or represents a radical of the formula —NR⁷R⁸ or —OR⁹,
in which
$R^7$ and $R^8$ independently of one another represent hydrogen, $(C_6-C_{10})$-aryl, adamantyl, $(C_1-C_8)$-alkyl, whose chain may be interrupted by one or two oxygen atoms and which may be substituted up to three times independently of one another by hydroxyl, phenyl, trifluoromethyl, $(C_3-C_8)$-cycloalkyl, $(C_1-C_6)$-alkoxy, mono- or di-$(C_1-C_6)$-alkylamino, or represent $(C_3-C_8)$-cycloalkyl, which may be substituted up to three times independently of one another by $(C_1-C_4)$-alkyl, hydroxyl or oxo, and $R^9$ represents $(C_6-C_{10})$-aryl, adamantyl, $(C_1-C_8)$-alkyl, whose chain may be interrupted by one or two oxygen atoms and which may be substituted up to three times independently of one another by hydroxyl, phenyl, trifluoromethyl, $(C_3-C_8)$-cycloalkyl, $(C_1-C_6)$-alkoxy, mono- or di-$(C_1-C_6)$-alkylamino, or represents $(C_3-C_8)$-cycloalkyl, which may be substituted up to three times independently of one another by $(C_1-C_4)$-alkyl, hydroxyl or oxo, $R^3$ represents $(C_1-C_8)$-alkyl, whose chain may be interrupted by a sulphur or oxygen atom or an S(O) or SO₂ group, or represents phenyl or benzyl where phenyl and benzyl may be substituted up to three times independently of one another by halogen, trifluoromethyl, cyano, nitro, hydroxyl, $(C_1-C_6)$-alkyl or $(C_1-C_6)$-alkoxy, and $R^4$ represents a radical of the formula —C(O)—NR¹⁰R¹¹,
in which
$R^{10}$ and $R^{11}$ independently of one another represent hydrogen or $(C_1-C_6)$-alkyl, or a salt, hydrate, hydrate of the salt, or solvate thereof.

2. A compounds according to claim 1,
in which
D represents a radical

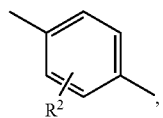, in which
$R^2$ represents hydrogen, halogen, hydroxyl, carboxyl, cyano, nitro, trifluoromethyl, trifluoromethoxy, $(C_1-C_6)$-alkyl, $(C_1-C_6)$-alkoxy or $(C_1-C_6)$-alkoxycarbonyl, A represents a group of the formula N—$R^5$,
in which
$R^5$ represents hydrogen, $(C_1-C_6)$-alkyl, $(C_3-C_7)$-cycloalkyl, where alkyl and cycloalkyl for their part may be substituted up to three times independently of one another by hydroxyl or mono- or di-$(C_1-C_6)$-alkylamino, or represents $(C_6-C_{10})$-aryl, where aryl for its part may be substituted up to three times independently of one another by halogen, hydroxyl, cyano, nitro, trifluoromethyl, trifluoromethoxy, $(C_1-C_6)$-alkyl, $(C_1-C_6)$-alkoxy, $(C_1-C_6)$-alkoxycarbonyl or mono- or di-$(C_1-C_6)$-alkylamino, $R^1$ represents hydrogen, $(C_1-C_6)$-alkyl, which for its part may be substituted by hydroxyl or $(C_1-C_4)$-alkoxy, or represents $(C_3-C_7)$-cycloalkyl or $(C_6-C_{10})$-aryl, where aryl for its part may be substituted independently of one another by halogen, or represents a radical of the formula —NR⁷R⁸ or —OR⁹,
in which
$R^7$ and $R^8$ independently of one another represent hydrogen, $(C_6-C_{10})$-aryl, adamantyl, $(C_1-C_8)$-alkyl, whose chain may be interrupted by one or two oxygen atoms and which may be substituted up to three times independently of one another by hydroxyl, phenyl, trifluoromethyl, $(C_3-C_8)$-cycloalkyl, $(C_1-C_6)$-alkoxy, mono- or di-$(C_1-C_6)$-alkylamino, or represent $(C_3-C_8)$-cycloalkyl, which may be substituted up to three times independently of one another by $(C_1-C_4)$-alkyl, hydroxyl or oxo, and $R^9$ represents $(C_6-C_{10})$-aryl, adamantyl, $(C_1-C_8)$-alkyl, whose chain may be interrupted by one or two oxygen atoms and which may be substituted up to three times independently of one another by hydroxyl, phenyl, trifluoroomethyl, $(C_3–C_8)$-cycloalkyl, $(C_1–C_6)$-alkoxy, mono- or di-$(C_1–C_6)$-alkylamino, or represents $(C_3–C_8)$-cycloalkyl, which may be substituted up to three times independently of one another by $(C_1–C_4)$-alkyl, hydroxyl or oxo, $R^3$ represents $(C_1–C_8)$-alkyl, whose chain may be interrupted by a sulphur atom or an S(O) or $SO_2$ group, or represents phenyl or benzyl where phenyl and benzyl may be substituted up to three times independently of one another by halogen, trifluoroomethyl, cyano, nitro, hydroxyl, $(C_1–C_6)$-alkyl or $(C_1–C_6)$-alkoxy, and $R^4$ represents a radical of the formula —C(O)—$NR^{10}R^{11}$, in which
$R^{10}$ and $R^{11}$ independently of one another represent hydrogen or $(C_1–C_6)$-alkyl, or a salt, hydrate, hydrate of the salt, or solvate thereof.

3. Compounds according to claim 1,
in which
D represents a radical

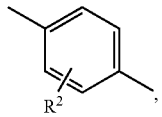

in which
$R^2$ represents hydrogen, chlorine or fluorine,
A represents a group of the formula N—$R^5$,
in which
$R^5$ represents hydrogen, $(C_1–C_6)$-alkyl, which for its part may be substituted up to two times by hydroxyl, or represents $(C_3–C_7)$-cycloalkyl or phenyl where phenyl for its part may be substituted up to two times independently of one another by halogen, cyano, trifluoroomethyl, trifluoroomethoxy, $(C_1–C_4)$-alkyl, $(C_1–C_4)$-alkoxy or di-$(C_1–C_4)$-alkylamino,
$R^1$ represents hydrogen, $(C_1–C_6)$-alkyl, which for its part may be substituted by hydroxyl or $(C_1–C_4)$-alkoxy, or represents $(C_3–C_7)$-cycloalkyl or phenyl, where phenyl for its part independently may be substituted independently of one another by halogen, or represents a radical of the formula —$NR^7R^8$ or —$OR^9$,
in which
$R^7$ and $R^8$ independently of one another represent hydrogen, phenyl, adamantyl, $(C_1–C_6)$-alkyl, whose chain may be interrupted by one or two oxygen atoms and which may be substituted up to two times independently of one another by hydroxyl, phenyl, trifluoroomethyl, $(C_3–C_6)$-cycloalkyl, $(C_1–C_4)$-alkoxy, mono- or di-$(C_1–C_4)$-alkylamino, or represents $(C_3–C_8)$-cycloalkyl, which may be substituted up to two times by hydroxyl,
and
$R^9$ represents phenyl, adamantyl, $(C_1–C_6)$-alkyl, whose chain may be interrupted by one or two oxygen atoms and which may be substituted up to two times independently of one another by hydroxyl, phenyl, trifluoroomethyl, $(C_3–C_6)$-cycloalkyl, $(C_1–C_3)$-alkoxy, mono- or di-$(C_1–C_4)$-alkylamino, or represents $(C_3–C_8)$-cycloalkyl, which may be substituted up to two times by hydroxyl,
$R^3$ represents $(C_1–C_8)$-alkyl, whose chain may be interrupted by a sulphur atom or an S(O) or $SO_2$ group, or represents phenyl or benzyl where phenyl and benzyl may be substituted up to two times independently of one another by halogen, trifluoroomethyl, cyano, $(C_1–C_3)$-alkyl, $(C_1–C_3)$-alkoxy or hydroxyl, and $R^4$ represents a radical of the formula —C(O)—$NR^{10}R^{11}$,
in which
$R^{10}$ and $R^{11}$ independently of one another represent hydrogen or $(C_1–C_6)$-alkyl, or a salt, hydrate, hydrate of the salt, or solvate thereof.

4. A compounds according to claim 1,
in which
D represents a radical of the formula

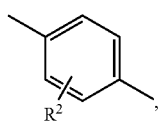

in which
$R^2$ represents hydrogen,
A represents a group of the formula N—$R^5$,
in which
$R^5$ represents hydrogen, $(C_1–C_6)$-alkyl, which for its part may be substituted up to two times by hydroxyl, or represents $(C_3–C_7)$-cycloalkyl or phenyl where phenyl for its part may be substituted up to two times independently of one another by fluorine, chlorine, cyano, trifluoroomethyl, trifluoroomethoxy, $(C_1–C_3)$-alkyl, $(C_1–C_3)$-alkoxy or di-$(C_1–C_3)$-alkylamino,
$R^1$ represents $(C_1–C_4)$-alkyl or a radical of the formula —$NR^7R^8$,
in which
$R^7$ and $R^8$ independently of one another represent hydrogen, phenyl, adamantyl, $(C_1–C_4)$-alkyl, whose chain may be interrupted by one or two oxygen atoms and which may be substituted up to two times independently of one another by hydroxyl, phenyl, trifluoroomethyl, $(C_3–C_6)$-cycloalkyl, $(C_1–C_3)$-alkoxy, mono- or di-$(C_1–C_3)$-alkylamino, or represent $(C_3–C_8)$-cycloalkyl, which may be substituted up two times by hydroxyl,
$R^3$ represents $(C_1–C_8)$-alkyl, whose chain may be interrupted by a sulphur atom or an S(O) or $SO_2$ group, or represents phenyl or benzyl where phenyl and benzyl may be substituted up to two times independently of one another by halogen, trifluoroomethyl, cyano, $(C_1–C_3)$-alkyl, $(C_1–C_3)$-alkoxy or hydroxyl, and $R^4$ represents a radical of the formula —C(O)—$NR^{10}R^{11}$,
in which
$R^{10}$ and $R^{11}$ independently of one another represent hydrogen, methyl or ethyl, or a salt, hydrate, hydrate of the salt, or solvate thereof.

5. A compounds according to claim 1,
in which

D represents a radical

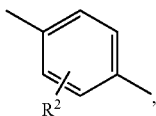

in which
R² represents hydrogen,

A represents a group of the formula N—R⁵,
in which
R⁵ represents $(C_3-C_7)$-cycloalkyl, or phenyl, which for its part may be substituted by fluorine, R¹ represents methyl or a radical of the formula —NR⁷R⁸,
in which
R⁷ and R⁸ independently of one another represent $(C_1-C_4)$-alkyl, which may be mono- or disubstituted by hydroxyl, R³ represents phenyl, which is optionally substituted in the para-position by fluorine,
and R⁴ represents a radical of the formula —C(O)—NR¹⁰R¹¹,
in which
R¹⁰ and R¹¹ represent hydrogen, or a salt, hydrate, hydrate of the salt, or solvate thereof.

6. A compound according to claim 1, characterized by one of the following stereochemical configurations according to formulae (Ia) to (Id):

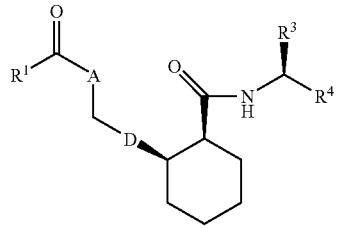
(Ia)

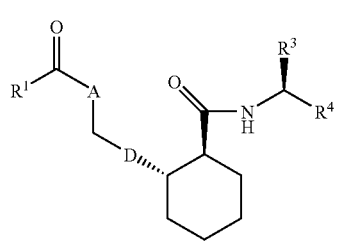
(Ib)

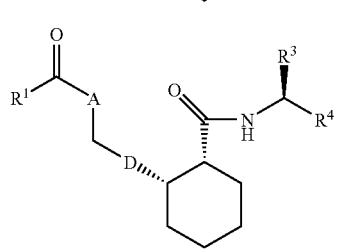
(Ic)

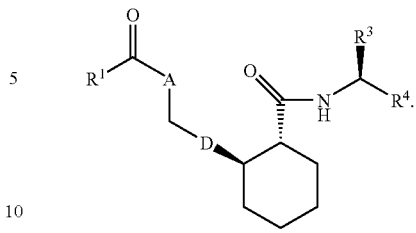
(Id)

7. A compound according to claim 1, characterized by the following stereochemical configuration according to formula (Id):

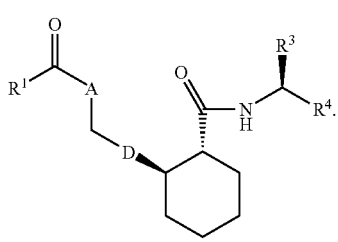
(Id)

8. A compound according to claim 1 having the following structures:

(1R,2R)-N-[(1S)-2-amino-1-(4-fluorophenyl)-2-oxoethyl]-2-(4-{[{[ethyl(2-hydroxyethyl)amino]carbonyl}(4-fluorophenyl)amino]methyl}phenyl)cyclohexanecarboxamide

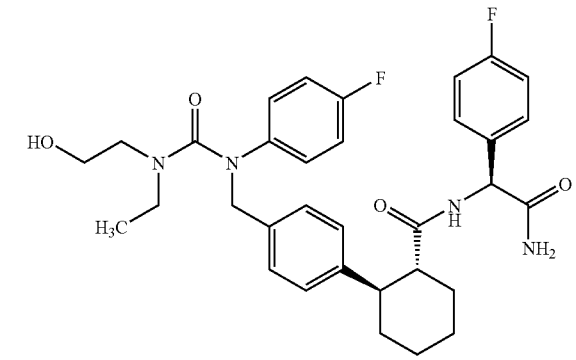

(1R,2R)-N-[(1S)-2-amino-2-oxo-1-phenylethyl]-2-(4-{[[(dimethylamino)carbonyl]-(phenyl)amino]methyl}phenyl)cyclohexanecarboxamide

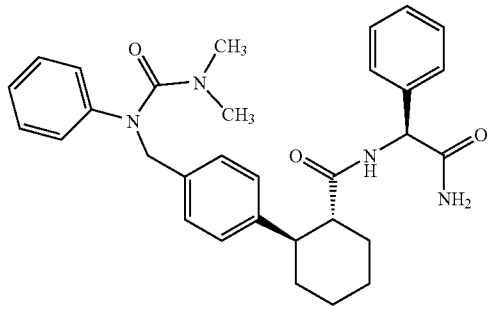

(1R,2R)-N-[(1S)-2-amino-2-oxo-1-phenylethyl]-2-[4-({cyclopropyl[(dimethylamino)carbonyl]amino}methyl)phenyl]cyclohexanecarboxamide

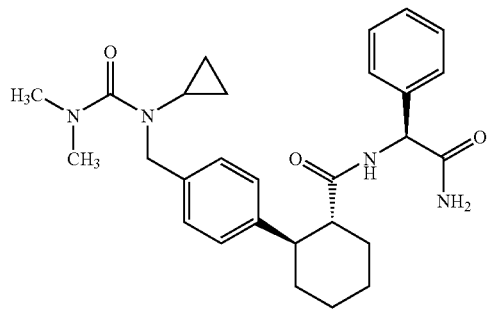

(S)-N-{{(1R,2R)-2-(4-{[{[2-hydroxylethylamino]carbonyl}(phenyl)amino]methyl}phenyl)cyclohex-1-yl}carbonyl}-phenylglycinamide

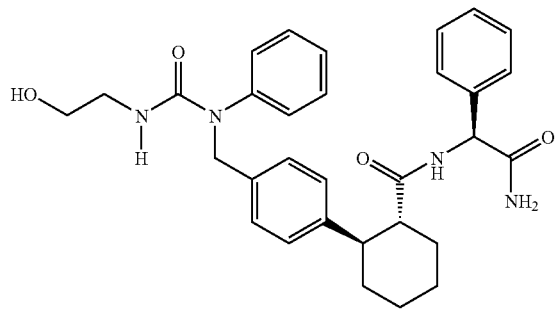

(1R,2R)-N-[(1S)-2-amino-1-phenyl-2-oxoethyl]-2-(4-{[{[ethyl(2-hydroxyethyl)amino]carbonyl}(phenyl)amino]methyl}phenyl)cyclohexanecarboxamide

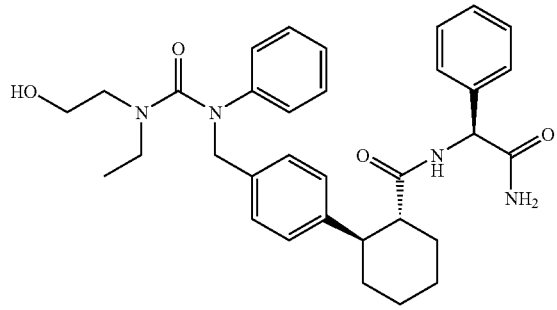

or a salt, hydrate, hydrate of the salt, or solvate thereof.

9. A process for preparing compounds of the formula (I), characterized in that (A) a compound of the formula (II)

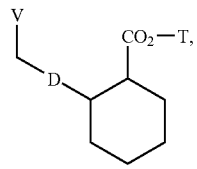
(II)

in which
D is as defined in claim 1,

T represents $(C_1–C_4)$-alkyl, and

V represents a suitable leaving group is initially converted by reaction with a compound of the formula (III)

 (III), in which

B represents

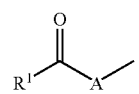

or optionally, if $R^1$ reprsents $OR^9$, represents

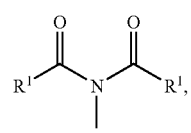

and $R^1$ and A are as defined in claim 1, into the compound of the formula (IV)

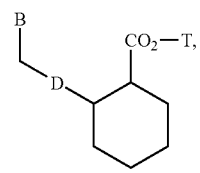 (IV)

in which B and T are as defined above and D is as defined in claim 1, this compound is in a next step converted with acid or base into the corresponding carboxylic acid of the formula (V)

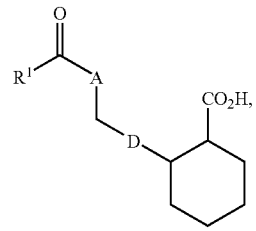 (V)

in which $R^1$, A and D are as defined in claim 1, and this compound is finally reacted in inert solvent according to known methods with a compound of the formula (VI) or a salt thereof

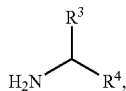 (VI)

in which $R^3$ and $R^4$ are as defined in claim 1, or (B) if A represents $NR^5$, a compound of the formula (VII)

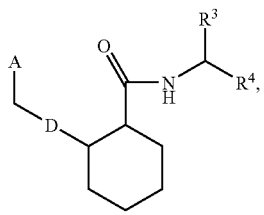 (VII)

in which

D, $R^3$ and $R^4$ are as defined in claim 1, and

A represents a group of the formula $N-R^5$, where $R^5$ is as defined in claim 1, is reacted either with a compound of the formula (VIII)

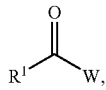 (VIII)

in which $R^1$ is as defined in claim 1 and W represents a suitable leaving group or with a phosgene equivalent and then with a compound of the formula (IX)

 $R^7R^8NH$ (IX), in which $R^7$ and $R^8$ are as defined in claim 1 or with an isocyanate of the formula (X)

 $R^7NCO$ (X), in which $R^7$ is as defined in claim 1.

10. A process for preparing a compound of the formula (I), characterized in that (A) a compound of the formula (V)

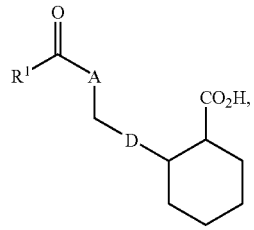 (V)

in which $R^1$, A and D are as defined in claim 1, is reacted in inert solvent according to known methods with a compound of the formula (VI) or salt thereof

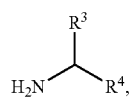 (VI)

in which $R^3$ and $R^4$ are as defined in claim 1, or (B) if A represents $NR^5$, a compound of the formula (VII)

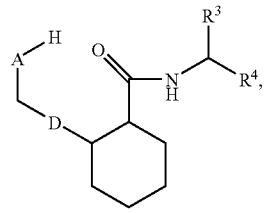 (VII)

in which

D, $R^3$ and $R^4$ are as defined in claim 1, and

A represents a group of the formula $N-R^5$, where $R^5$ is as defined in claim 1, is reacted either with a compound of the formula (VIII)

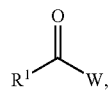 (VIII)

in which $R^1$ is as defined in claim 1 and W represents a suitable leaving group or with a phosgene equivalent and then with a compound of the formula (IX)

 $R^7R^8NH$ (IX), in which $R^7$ and $R^8$ are as defined in claim 1, or with an isocyanate of the formula (X)

  (X), in which

R⁷ is as defined in claim 1.

11. A compounds of the formula (V)

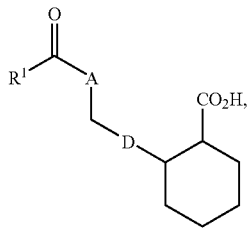  (V)

in which

R¹, A and D are as defined in claim 1, or a salt, hydrate, hydrate of the salt, or solvate thereof.

12. A compounds of the formula (VII)

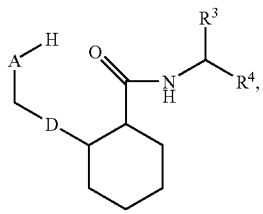  (VII)

in which

R³, R⁴, A and D are as defined in claim 1, or a salt, hydrate, hydrate of the salt, or solvate thereof.

13. A pharmaceutical composition comprising at least one compound of the formula (I) as defined in claim 1, and at least one further pharmaceutically active compound.

14. A pharmaceutical composition comprising at least one compound of the formula (I) as defined in claim 1, and at least one further pharmaceutically acceptable auxiliary.

15. A methods for the treatment of peripheral and cardiovascular disorders caused by ischaemia, comprising administering to a mammal an effective amount of a compound of claim 1.

16. The method of claim 15, wherein said disorder is selected from coronary heart disease, stable and unstable angina pectoris, peripheral and arterial occlusive diseases, thrombotic vascular occlusions, myocardial infarction and reperfusion damage.

* * * * *